(12) United States Patent
Miyawaki et al.

(10) Patent No.: US 6,569,178 B1
(45) Date of Patent: May 27, 2003

(54) ULTRASONIC COAGULATING/CUTTING APPARATUS

(75) Inventors: Makoto Miyawaki, Tanashi (JP); Mitsumasa Okada, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/518,085

(22) Filed: Mar. 3, 2000

(30) Foreign Application Priority Data

Mar. 9, 1999 (JP) .......................................... 11-061492
Mar. 11, 1999 (JP) .......................................... 11-064772

(51) Int. Cl.⁷ .............................................. A61B 17/32
(52) U.S. Cl. ..................... 606/169; 606/205; 604/22
(58) Field of Search .............................. 606/169, 170, 606/205, 51, 52, 171, 180; 604/22

(56) References Cited

U.S. PATENT DOCUMENTS

| 2,631,585 A | * | 3/1953 | Siebrandt | |
| 3,585,985 A | * | 6/1971 | Gould | 606/171 |
| 4,919,152 A | * | 4/1990 | Ger | 606/142 |
| 5,322,055 A | | 6/1994 | Davison et al. | |
| 5,626,608 A | * | 5/1997 | Cuny et al. | 606/205 |
| 5,944,737 A | * | 8/1999 | Tsonton et al. | 606/169 |
| 5,980,510 A | * | 11/1999 | Tsonton et al. | 606/169 |
| 6,024,750 A | * | 2/2000 | Mastri et al. | 606/169 |
| 6,066,151 A | * | 5/2000 | Miyawaki et al. | 606/169 |

FOREIGN PATENT DOCUMENTS

| EP | 0 830 845 | * | 3/1998 | ................. 606/169 |
| JP | 6-7366 | | 1/1994 | |
| JP | 8-505801 | | 6/1996 | |
| JP | 8-275951 | | 10/1996 | |
| JP | 9-98979 | | 4/1997 | |
| JP | 10-155802 | | 6/1998 | |

* cited by examiner

*Primary Examiner*—Eric F. Winakur
*Assistant Examiner*—David J. McCrosky
(74) *Attorney, Agent, or Firm*—Frishauf, Holtz, Goodman & Chick, P.C.

(57) ABSTRACT

An ultrasonic coagulating/cutting apparatus is provided which includes a switching member for switching the force to hold an organism tissue between a jaw and a probe during operation for opening or closing the jaw.

25 Claims, 30 Drawing Sheets

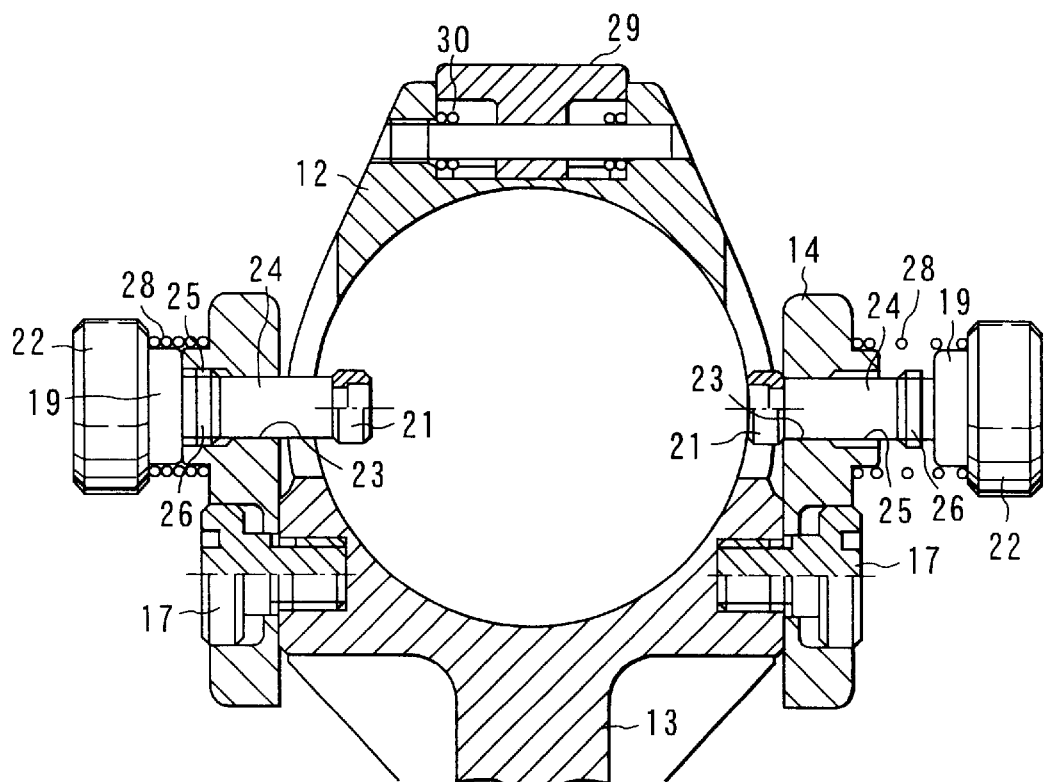
FIG. 5
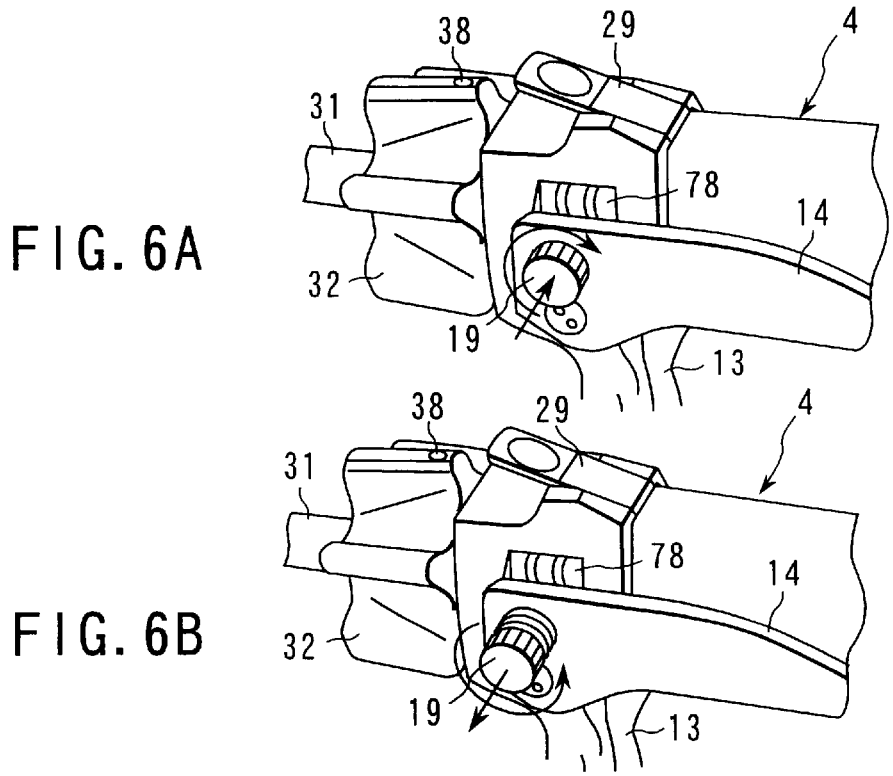
FIG. 6A
FIG. 6B

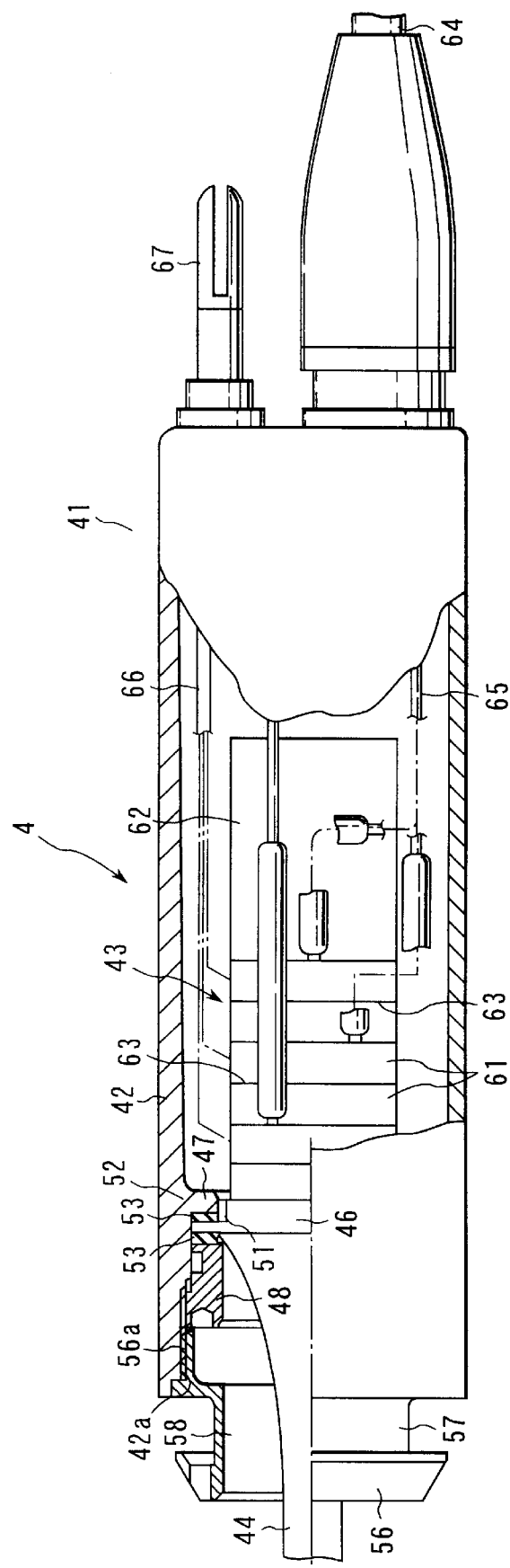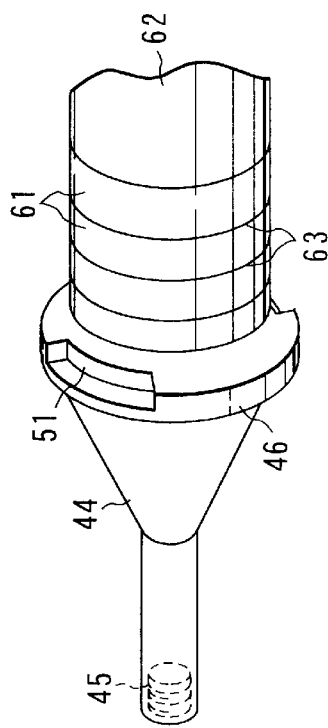
FIG. 7A
FIG. 7B

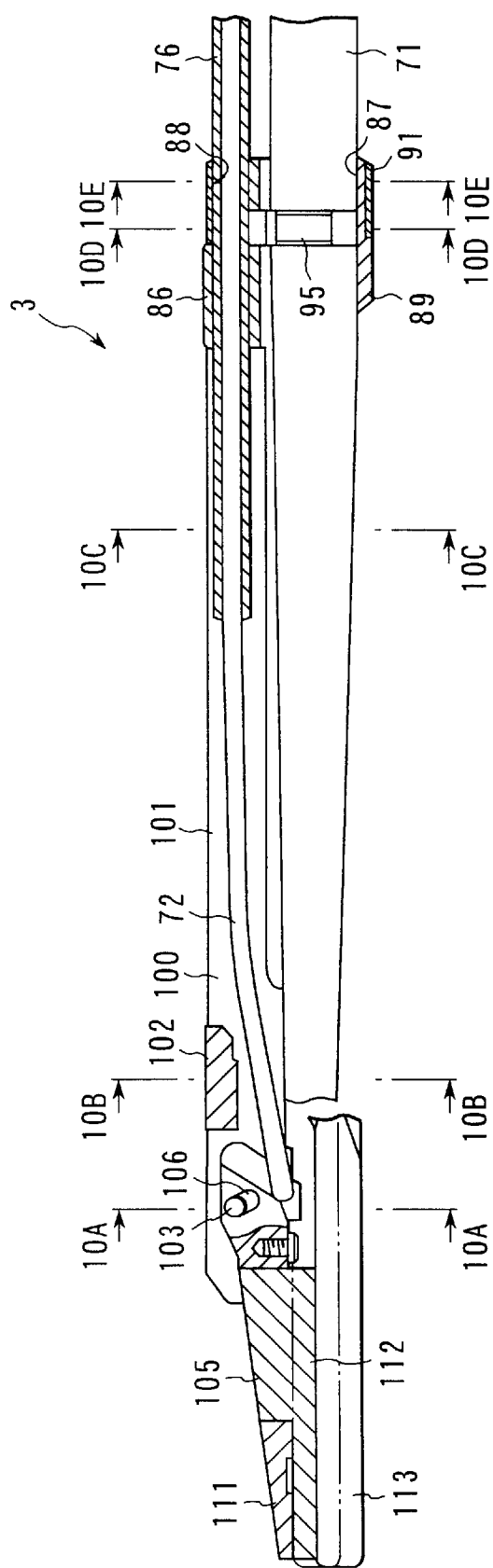
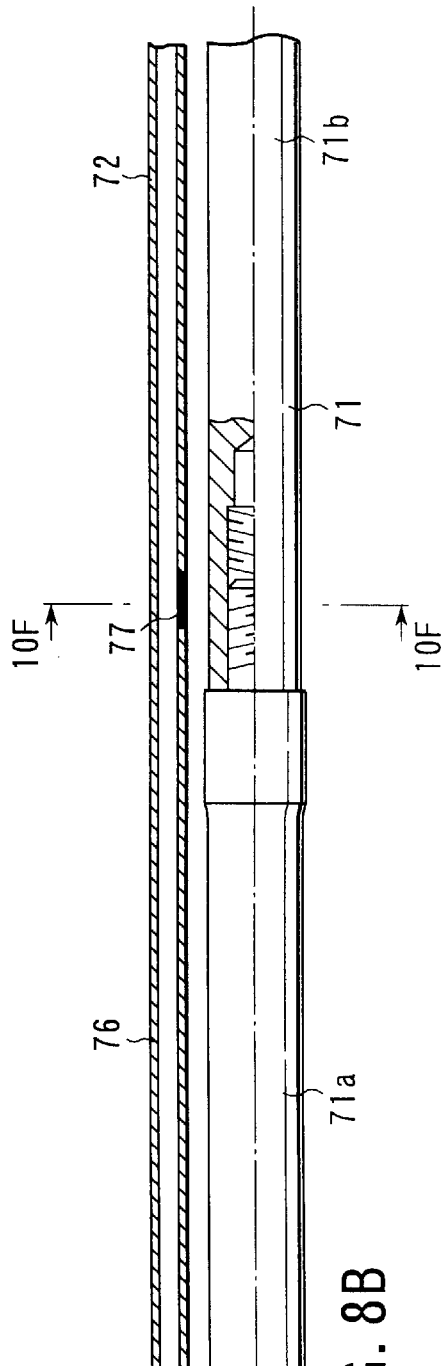
FIG. 8A
FIG. 8B

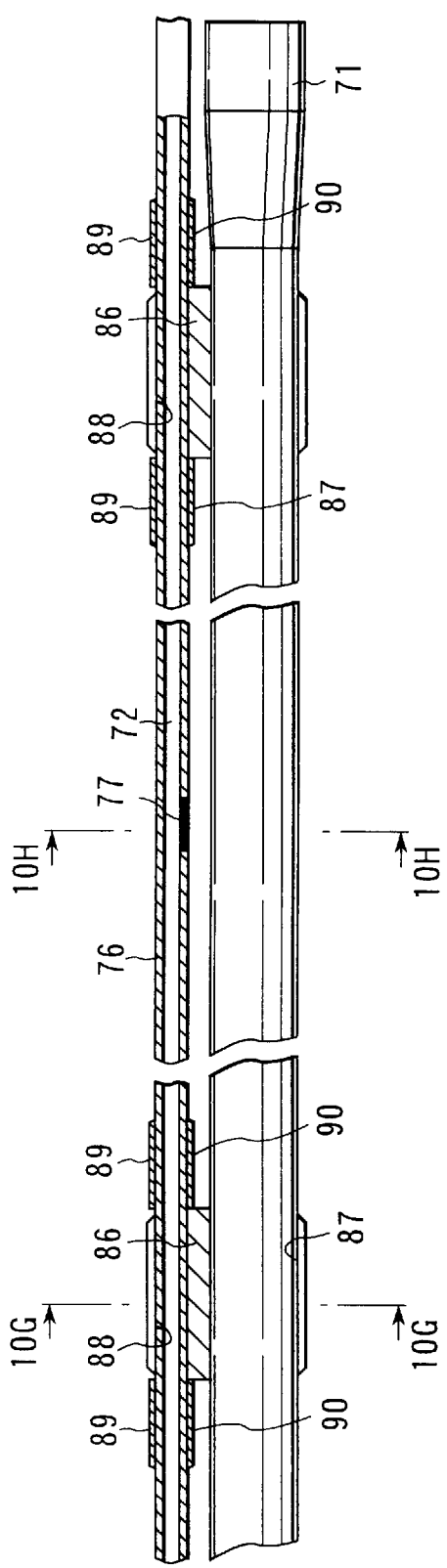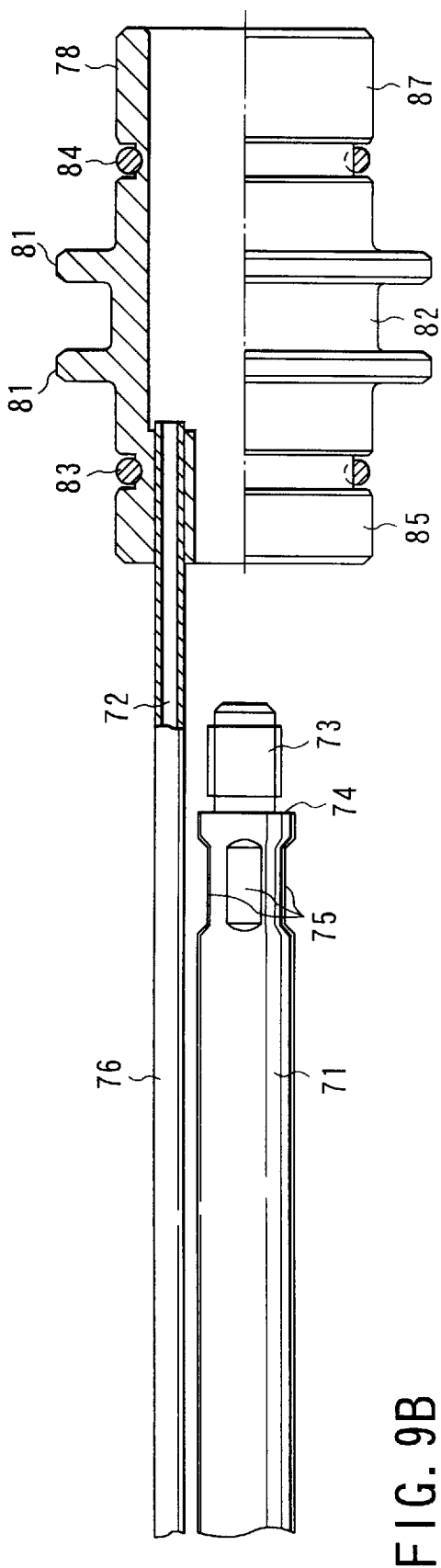
FIG. 9A
FIG. 9B

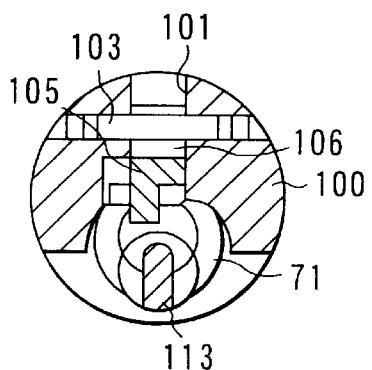
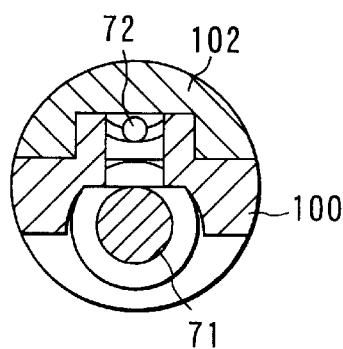
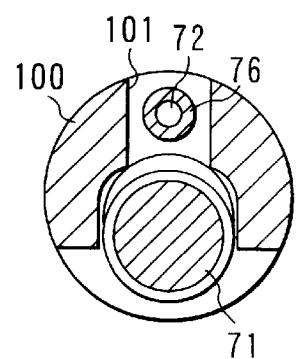
FIG. 10A  FIG. 10B  FIG. 10C
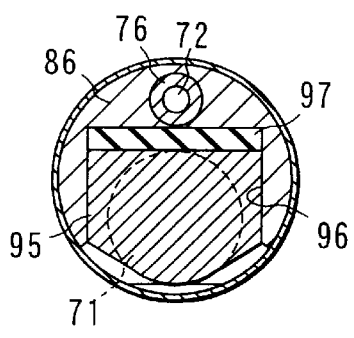
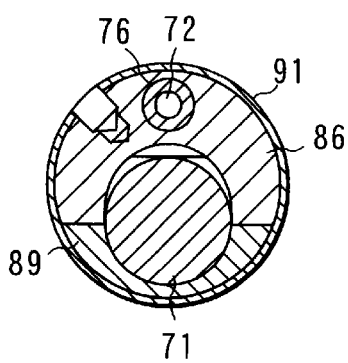
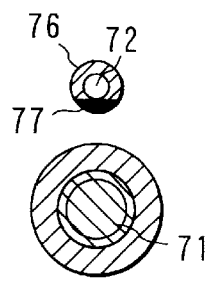
FIG. 10D  FIG. 10E  FIG. 10F
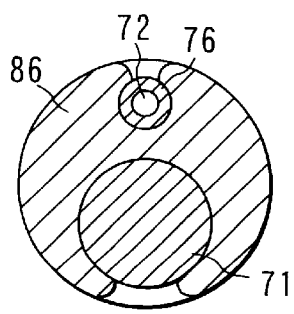
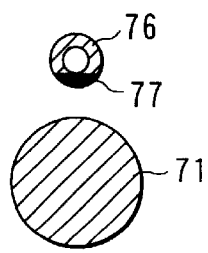
FIG. 10G  FIG. 10H

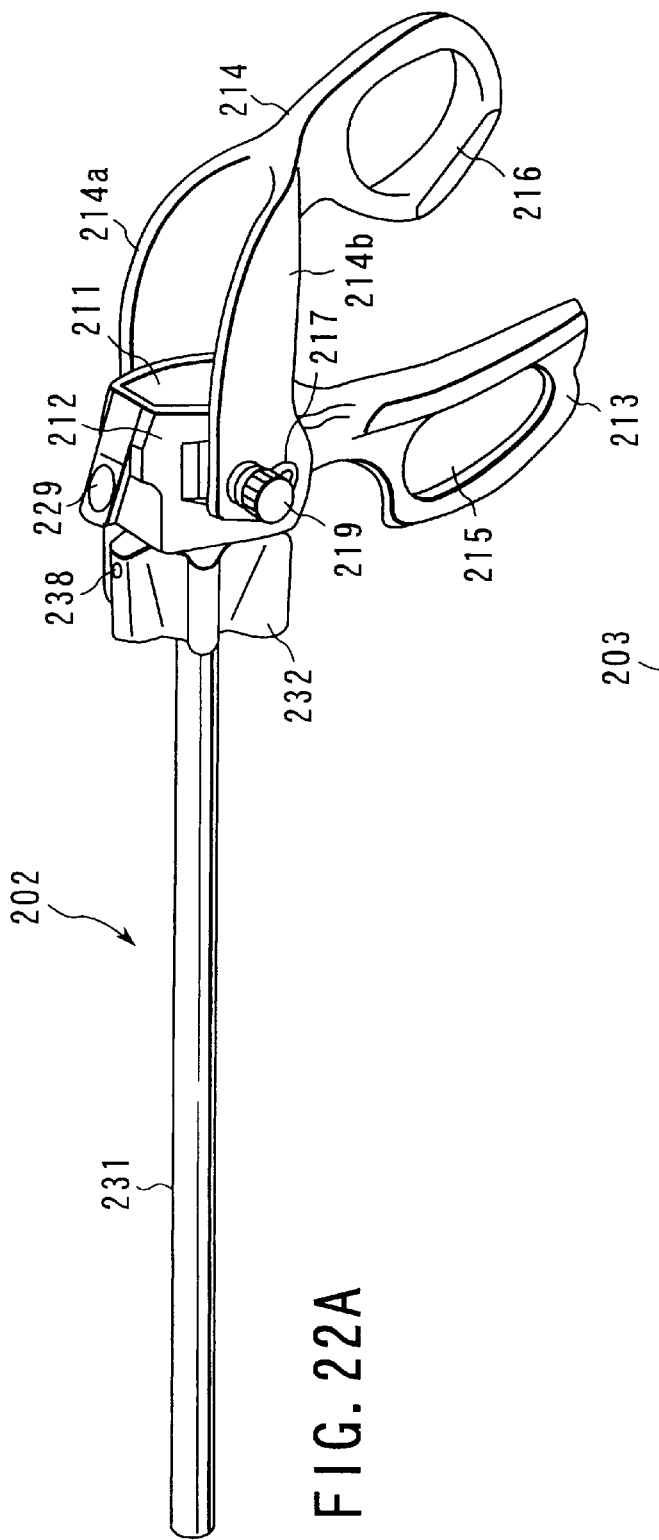
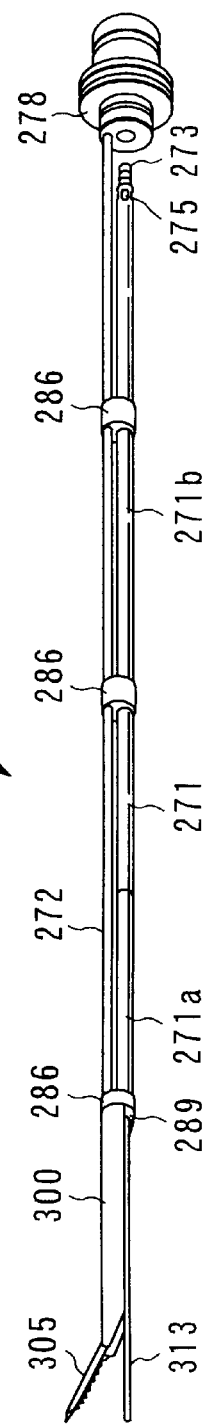
FIG. 22A
FIG. 22B

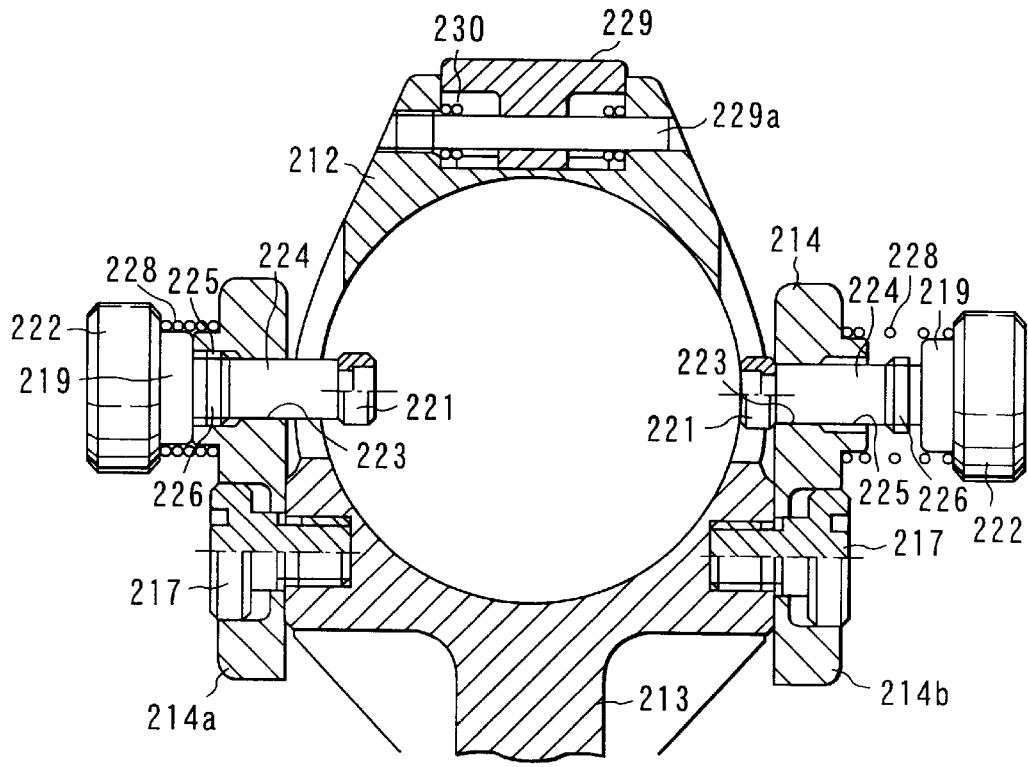
FIG. 25
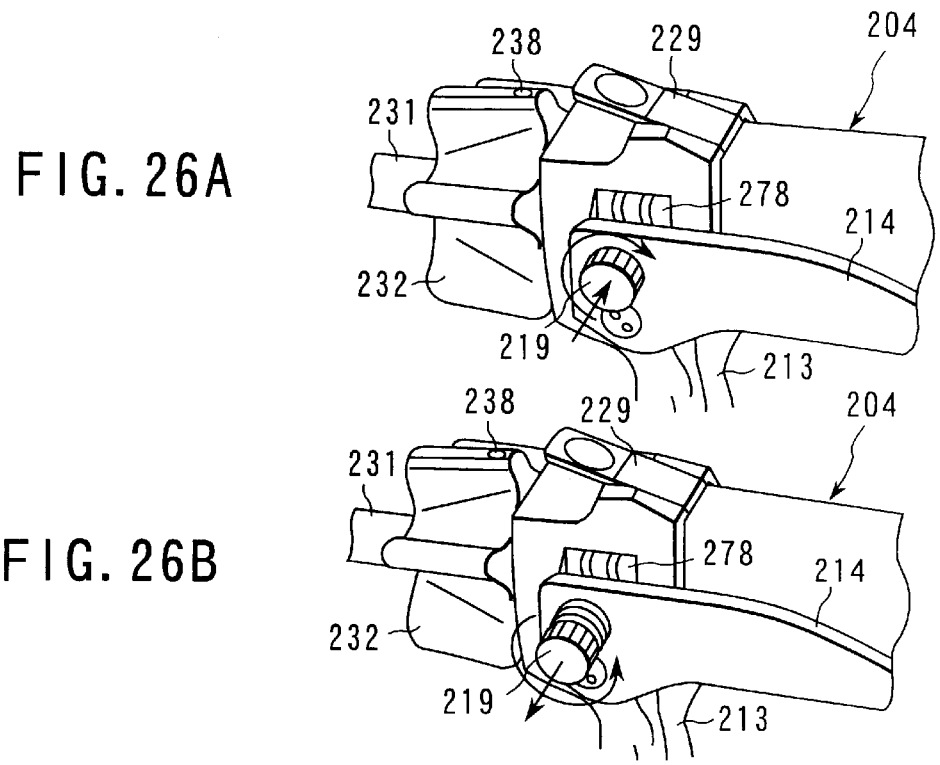
FIG. 26A
FIG. 26B

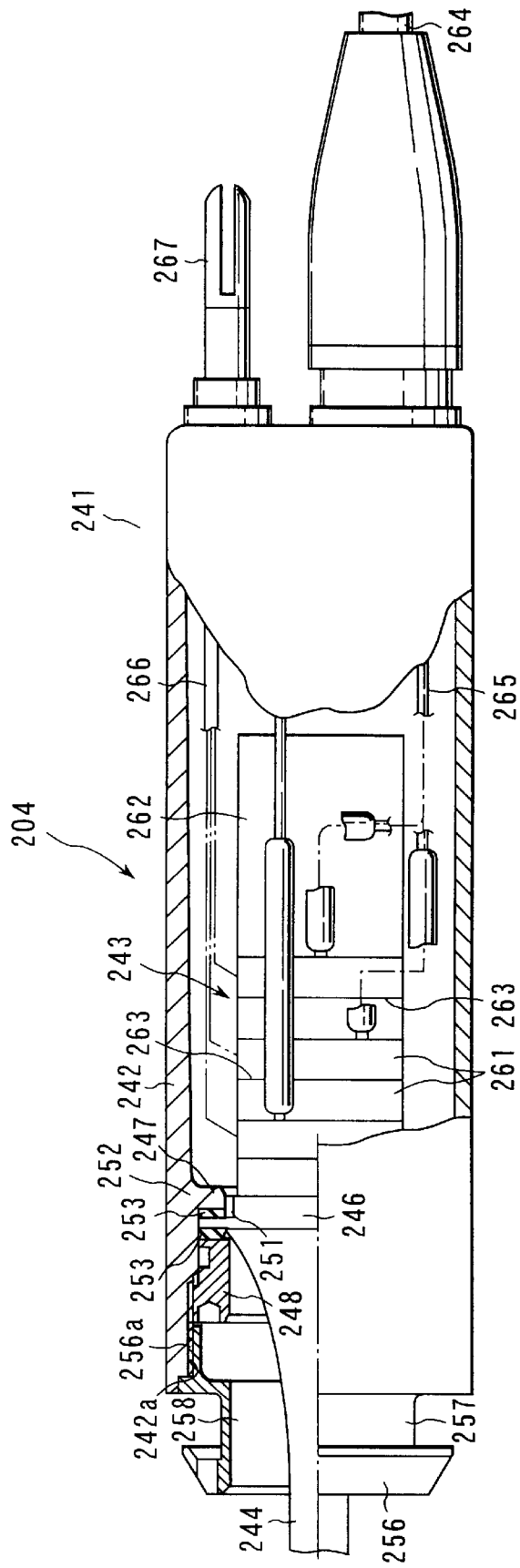
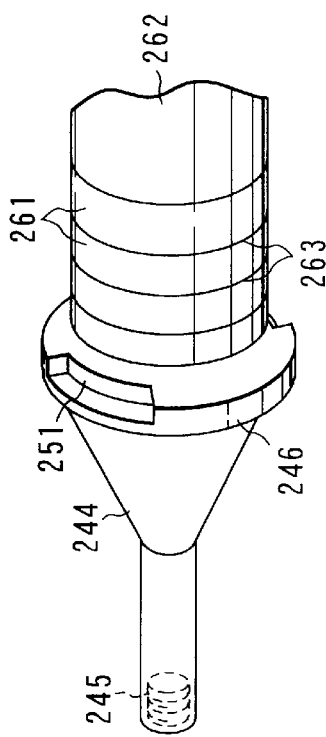
FIG. 27A
FIG. 27B

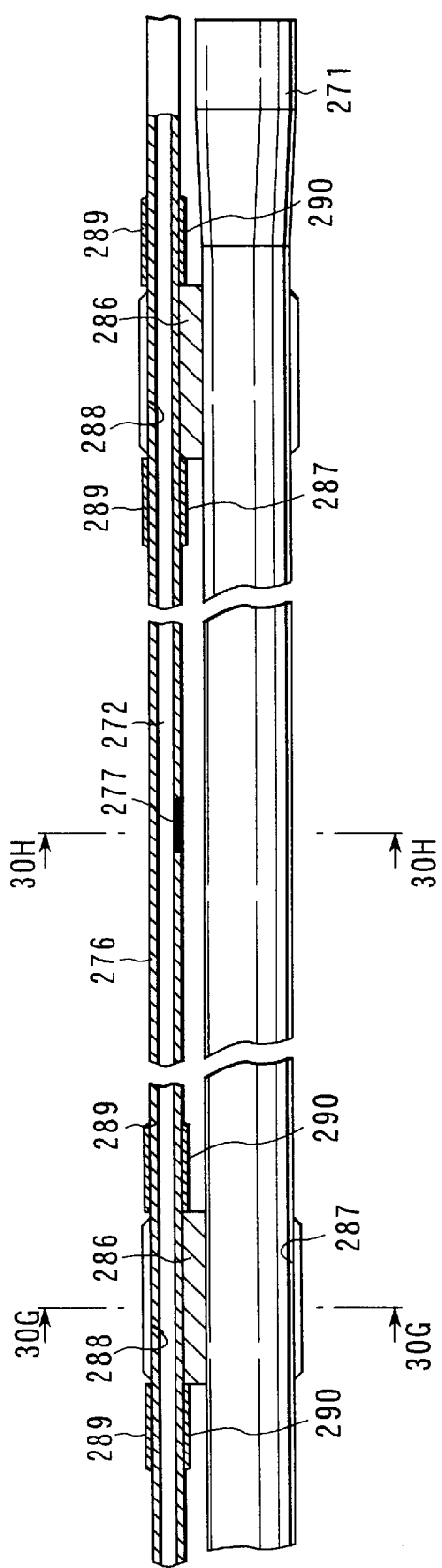
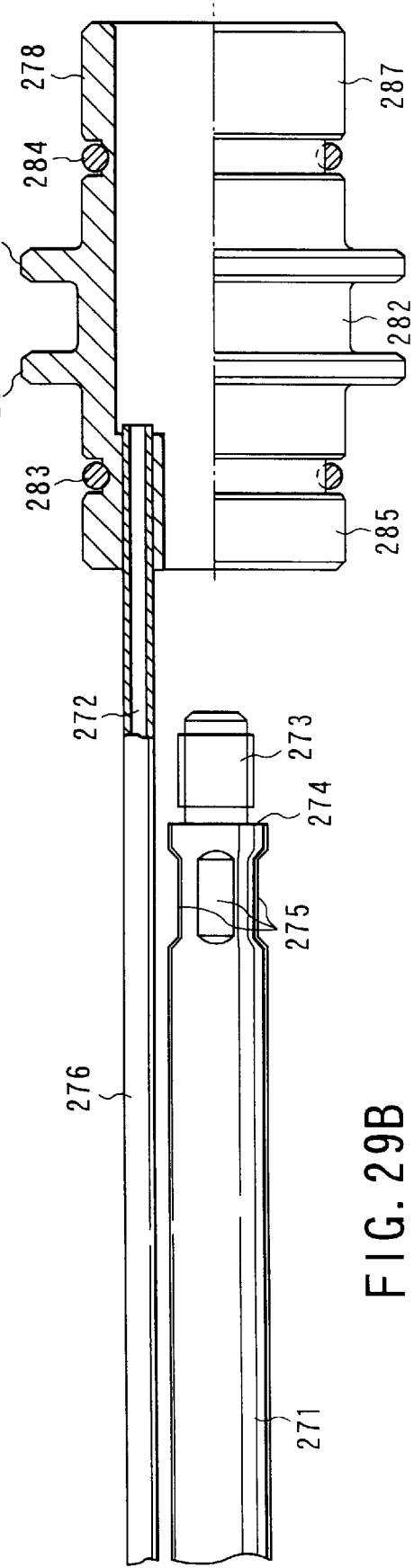
FIG. 29A
FIG. 29B

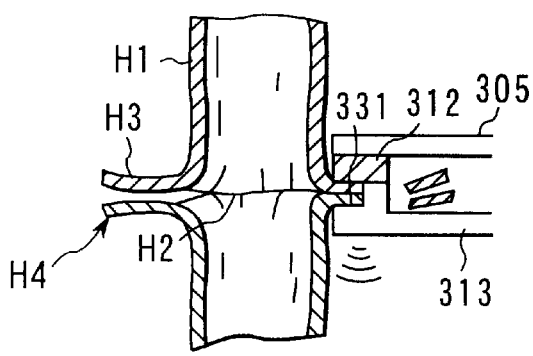 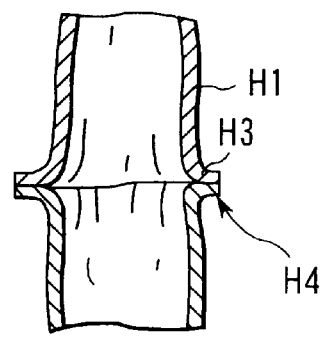
FIG. 33A  FIG. 33B
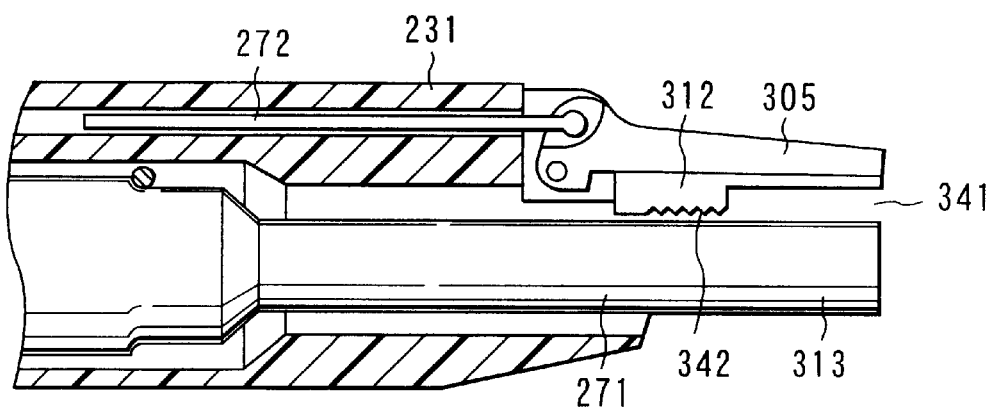
FIG. 34
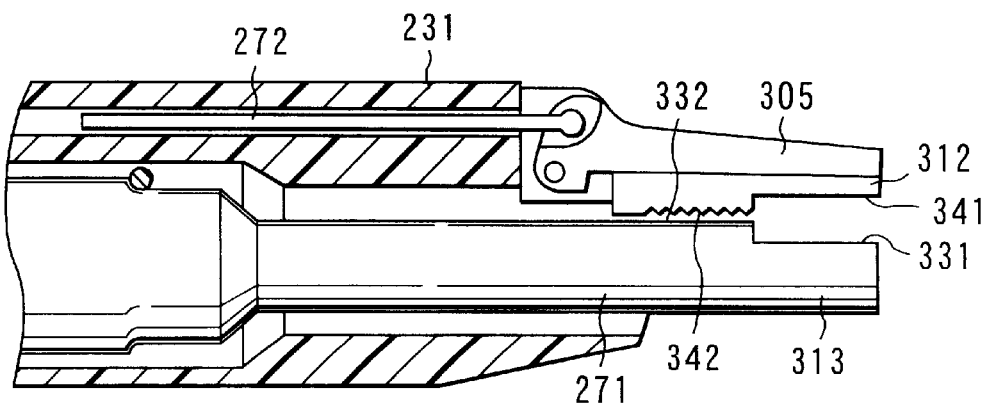
FIG. 35

ULTRASONIC COAGULATING/CUTTING APPARATUS

CROSS-REFERENCE TO RELATED APPLICATIONS

This application is based upon and claims the benefit of priority from the prior Japanese Patent Applications No. 11-61492, filed Mar. 9, 1999; and No. 11-64772, filed Mar. 11, 1999, the entire contents of which are incorporated herein by reference.

BACKGROUND OF THE INVENTION

The present invention relates to an ultrasonic coagulating/cutting apparatus for carrying out treatment such as incision, excision, or coagulation of an organism tissue by utilizing ultrasonic waves while grasping the organism tissue in- and outside the body.

An apparatus described in U.S. Pat. No. 5,322,055 is generally known as an example of an ultrasonic coagulating/cutting apparatus. This ultrasonic coagulating/cutting apparatus is provided with an ultrasonic vibrator for generating ultrasonic vibration, a vibration transmitting member connected to the ultrasonic vibrator, a blade (probe) formed on the distal end portion of the vibration transmitting member, a jaw supported opposite to the blade for open-close motion, and a handle section for opening and closing the jaw.

In use, the jaw is opened or closed with respect to the blade through handle operation on the handle section. As the jaw is closed or rocked toward the blade, an organism tissue is held between the jaw and the blade.

Further, the ultrasonic vibrator is actuated with the organism tissue grasped. Ultrasonic vibration from the ultrasonic vibrator is transmitted to the blade by means of the vibration transmitting member, and the organism tissue is coagulated with the frictional heat of the ultrasonic vibration generated in the region of contact with the organism tissue as the organism tissue is subjected to treatment such as incision. As this is done, coagulating action and cutting action simultaneously work on the grasped region of the organism tissue, and the grasped part of the organism tissue region is cut without entailing bleeding.

Described in U.S. Pat. No. 5,322,055, moreover, is an arrangement such that the blade is provided with a knife-shaped cutting portion and a coagulating face having a profile substantially in the shape of a circular arc, and a state in which the cutting portion of the blade is opposed to the jaw and a state in which the coagulating face is opposed can be switched to and from each other. In the case where the cutting portion of the blade is opposed to the jaw, the cutting action for the grasped region of the organism tissue can be enhanced. In the case where the coagulating face of the blade is opposed to the jaw, moreover, the coagulating action for the grasped region of the organism tissue can be enhanced.

In the apparatus described in U.S. Pat. No. 5,322,055, however, the blade is provided with the cutting portion and the coagulating face, so that the construction of the blade is inevitably complicated. Further, the set state of the blade with respect to the jaw is changed to switch the mode between the state in which the cutting portion of the blade is opposed to the jaw so that the cutting action for the organism tissue is enhanced and the state in which the coagulating face of the blade is opposed to the jaw so that the coagulating action for the organism tissue is enhanced. Thus, blade changing operation for ultrasonic treatment is troublesome.

Described in Jpn. Pat. Appln. KOKAI Publication No. 8-275951, moreover, is an apparatus of a similar arrangement such that a jaw is activated by handle operation to hold an organism tissue between itself and a blade, and ultrasonic vibration is applied to the jaw to subject a grasped region of the organism tissue to treatment such as incision, excision, or coagulation.

Also described in this publication, furthermore, is an arrangement such that the jaw is provided with a coagulating face with a wide area of contact with the organism tissue and a cutting portion with a narrow area of contact with the organism tissue, and a state in which the cutting portion of the jaw is opposed to the blade and a state in which the coagulating face is opposed can be switched to and from each other. In this case, the cutting action for the grasped region of the organism tissue is enhanced when the cutting portion of the jaw is opposed to the jaw, and the coagulating action for the grasped region of the organism tissue is enhanced when the coagulating face of the jaw is opposed.

In the apparatus described in Jpn. Pat. Appln. KOKAI Publication No. 8-275951, however, the jaw is provided with the coagulating face and the cutting portion, so that the construction of the jaw is inevitably complicated. Further, the set state of the jaw is changed to switch the mode between the state in which the cutting action for the organism tissue is enhanced and the state in which the coagulating action for the organism tissue is enhanced. Thus, jaw changing operation for ultrasonic treatment is troublesome.

If the handle section is moved to its fully-closed position as the organism tissue is subjected to ultrasonic incision, in the apparatus of the conventional arrangement described above, moreover, the jaw is moved to its fully-closed position, whereby the grasped region of the organism tissue can be cut. As this is done, in the apparatus of the conventional arrangement, a constant grip force is generated when the handle section is moved to its fully-closed position so that the organism tissue is held between the blade and the jaw. Thus, it is hard to obtain appropriate coagulating/cutting performance according to the kind and thickness of the organism tissue.

In subjecting the organism tissue to treatment such as hemostasis, furthermore, the grasped region of the organism tissue can be subjected only to treatment such as coagulation without being cut if the jaw is held in a halfway position reached before it is moved to its fully-closed position with respect to the blade, that is, a halfway position reached before the handle section is moved to is fully-closed position, for a suitable period of time. The operations to hold the handle section in the halfway position reached before it is moved to the fully-closed position for the suitable period of time and to coagulate the organism tissue are carried out depending on an operator's feeling of operation.

However, the operating force for the handle section is subject to variations between individual operators, and continual operation with stable handle operating force requires experience and skill, so that variation in the finish of treatment is substantial. If the handle section is held with a small operating force for a relatively long time, for example, the range of coagulation for the organism tissue is wide. If the treatment for coagulation is finished with a great operating force for the handle section in a relatively short time, the range of coagulation for the organism tissue is narrow.

In subjecting the organism tissue to coagulative incision, moreover, there is a possibility of the organism tissue being mechanically cut before it is coagulated with the frictional heat of ultrasonic vibration in an extreme case if the handle is operated extraordinarily strongly or if the organism tissue is nipped with a great force, for example.

BRIEF SUMMARY OF THE INVENTION

The present invention has been contrived in consideration of these circumstances, and its object is to provide an ultrasonic coagulating/cutting apparatus of simple construction, capable of obtaining appropriate coagulating/cutting performance according to the kind and thickness of an organism tissue, and designed so that operation for the coagulation or coagulative incision of the organism tissue requires no special experience or skill, and which also enables a stable handling operation to be carried out with little possibility of entailing variation in the finish of treatment.

Another object of the present invention is to provide an ultrasonic coagulating/cutting apparatus of simple construction, capable of efficiently coagulating and excising an organism tissue at the same time.

In order to achieve the above objects, the present invention is provided with a switching member for switching the force to hold an organism tissue between a jaw and a probe during operation for opening or closing the jaw.

According to the present invention, moreover, the force to hold the organism tissue between the jaw and the probe during the operation for opening or closing the jaw is switched and adjusted by means of the switching member. Thus, appropriate coagulating/cutting performance can be obtained according to the kind and thickness of the organism tissue.

Further, the present invention in another aspect is provided with a position switching member accessible to external operation and capable of switching the moved position of the jaw being closed between a cutting position for cutting the organism tissue held between the jaw and the probe and a coagulating position where the jaw is stopped at a halfway position short of the cutting position.

According to the present invention, moreover, the moved position of the jaw being closed is switched by means of the position switching member between the cutting position for cutting the organism tissue held between the jaw and the probe and the coagulating position where the jaw is stopped at the halfway position short of the cutting position. Thus, appropriate coagulating/cutting performance can be obtained according to the kind and thickness of the organism tissue, the operation for the coagulation or coagulative incision of the organism tissue requires no special experiences or skill, and moreover, stable handle operation can be carried out with little possibility of entailing variation in the finish of treatment.

Further, the present invention in another aspect is provided with a non-contact portion located at least at a part of that surface of one member, the jaw or the probe, which faces the other member and capable of coagulating a to-be-treated region held between the probe and the jaw when the jaw is closed or rocked toward the probe.

According to the present invention, moreover, the to-be-treated region held between the probe and the jaw is excised (or incised) by means of contact portions of the jaw and the probe and the to-be-treated region held between the probe and the jaw is coagulated by means of the respective non-contact portions of the jaw and the probe when the jaw is closed or rocked toward the probe, whereby the coagulation of the organism tissue and the excision of the organism tissue can be carried out efficiently at the same time.

Further, the present invention in another aspect is provided with a projection located on the extreme end portion of the probe and serving to nip the organism tissue in conjunction with the jaw opposite thereto.

According to the present invention, moreover, the to-be-treated region held between the probe and the jaw is excised (or incised) by means of projections on the respective contact portions of the jaw and the probe and the to-be-treated region held between the probe and the jaw is coagulated by means of non-contact portions of the jaw and the probe other than the projections when the jaw is closed or rocked toward the probe, whereby the coagulation of the organism tissue and the excision of the organism tissue can be carried out efficiently at the same time.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 5 is a cross-sectional view of the handle unit of the ultrasonic coagulating/cutting apparatus of the first embodiment;

FIG. 6A is a perspective view for illustrating operation for attaching and detaching the handle unit of the first embodiment;

FIG. 6B is a perspective view showing the handle unit of the first embodiment with its fixing screw member removed;

FIG. 7A is a side view showing the principal part of the vibrator unit of the first embodiment in section;

FIG. 7B is a perspective view of its ultrasonic vibrator;

FIG. 8A is a profile of a distal-end-side portion of the probe unit of the first embodiment;

FIG. 8B is a profile of an intermediate portion of the probe unit of the first embodiment;

FIG. 9A is a profile showing the way spacers of the probe unit of the first embodiment are attached;

FIG. 9B is a side view showing the principal part of a rear-end-side portion of the probe unit of the first embodiment in section;

FIG. 10A is a sectional view taken along line 10A—10A of FIG. 8A;

FIG. 10B is a sectional view taken along line 10B—10B of FIG. 8A;

FIG. 10C is a sectional view taken along line 10C—10C of FIG. 8A;

FIG. 10D is a sectional view taken along line 10D—10D of FIG. 8A;

FIG. 10E is a sectional view taken along line 10E—10E of FIG. 8A;

FIG. 10F is a sectional view taken along line 10F—10F of FIG. 8B;

FIG. 10G is a sectional view taken along line 10G—10G of FIG. 9A;

FIG. 10H is a sectional view taken along line 10H—10H of FIG. 9A;

FIG. 22A is a perspective view of a handle unit of the ultrasonic coagulating/cutting apparatus of the sixth embodiment;

FIG. 22B is a perspective view of a probe unit;

FIG. 25 is a cross-sectional view of the handle unit of the ultrasonic coagulating/cutting apparatus of the sixth embodiment;

FIG. 26A is a perspective view for illustrating operation for attaching and detaching the handle unit of the sixth embodiment;

FIG. 26B is a perspective view showing the handle unit of the sixth embodiment with its fixing screw member removed;

FIG. 27A is a profile of the vibrator unit of the sixth embodiment;

FIG. 27B is a perspective view of its ultrasonic vibrator;

FIG. 29A is a profile showing the way spacers of the probe unit of the sixth embodiment are attached;

FIG. 29B is a side view showing the principal part of a rear-end-side portion of the probe unit of the sixth embodiment in section;

FIG. 33A is a view for illustrating operation for vascular inosculation using the ultrasonic coagulating/cutting apparatus of the sixth embodiment;

FIG. 33B is a profile showing an inosculated portion of a blood vessel having undergone the operation for vascular inosculation;

FIG. 34 is a profile of a distal treatment portion showing an arrangement of the principal part of an ultrasonic coagulating/cutting apparatus of a seventh embodiment of the present invention;

FIG. 35 is a profile of a distal treatment portion showing an arrangement of the principal part of an ultrasonic coagulating/cutting apparatus of an eighth embodiment of the present invention;

DETAILED DESCRIPTION OF THE INVENTION

Figure 1:
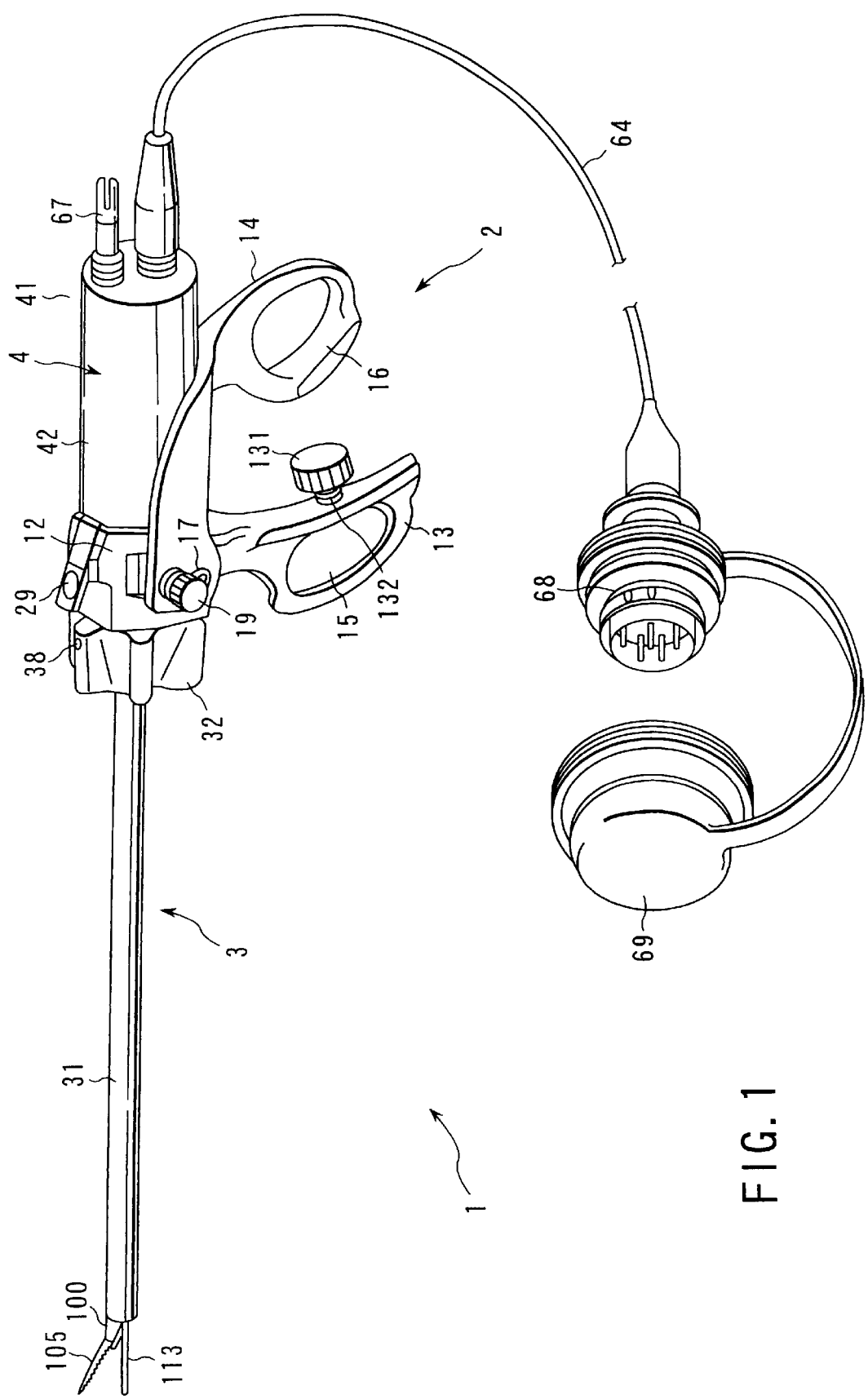
FIG. 1 is a perspective view showing an assembled state of an ultrasonic coagulating/cutting apparatus according to a first embodiment of the present invention.

A first embodiment of the present invention will now be described with reference to FIGS. 1 to 14B. FIG. 1 is a perspective view showing an outline of an ultrasonic coagulating/cutting apparatus 1 of the present embodiment. The ultrasonic coagulating/cutting apparatus 1 comprises a handle unit (operating member) 2 shown in FIG. 2A, a probe unit 3 shown in FIG. 2B, and a vibrator unit 4 shown in FIG. 3. These units 2, 3 and 4 of the ultrasonic coagulating/cutting apparatus 1 are assembled in the state shown in FIG. 1.

Figure 2A:
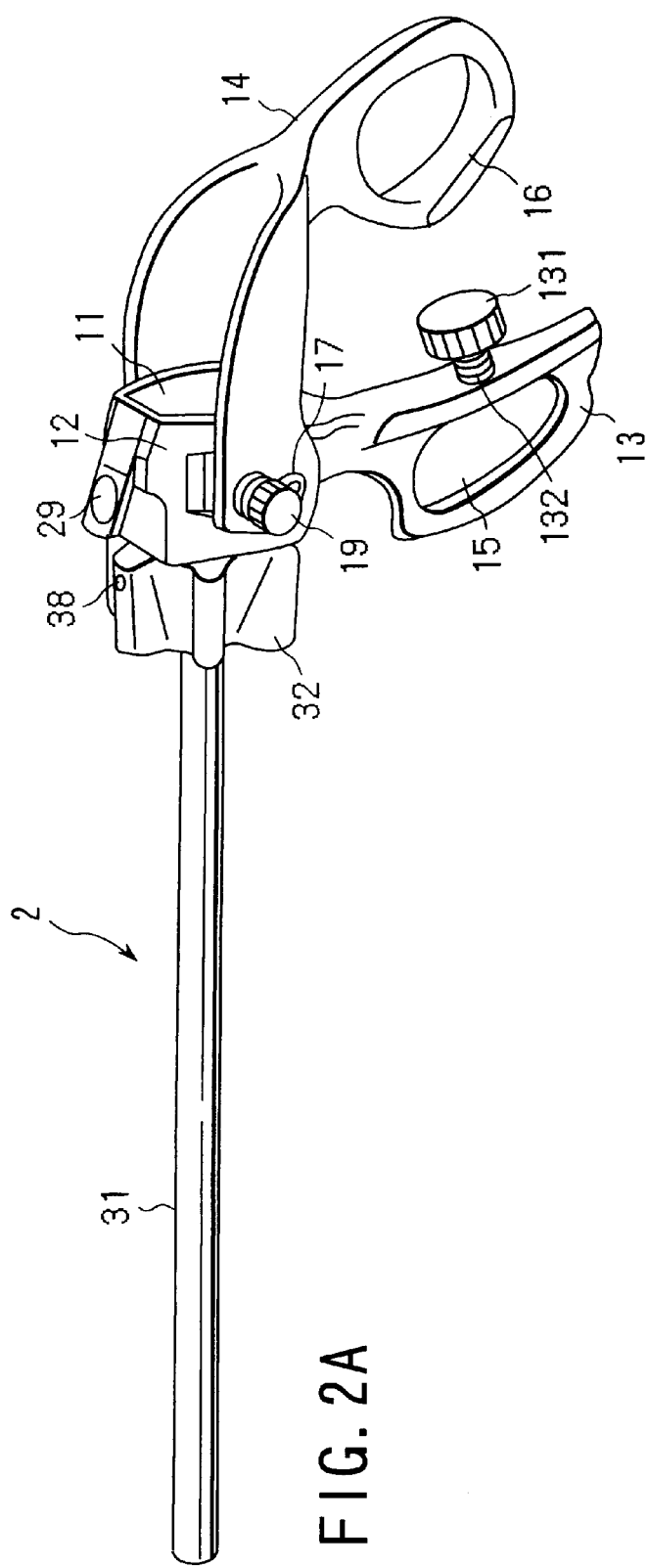
FIG. 2A is a perspective view of a handle unit of the ultrasonic coagulating/cutting apparatus of the first embodiment.
Figure 2B:
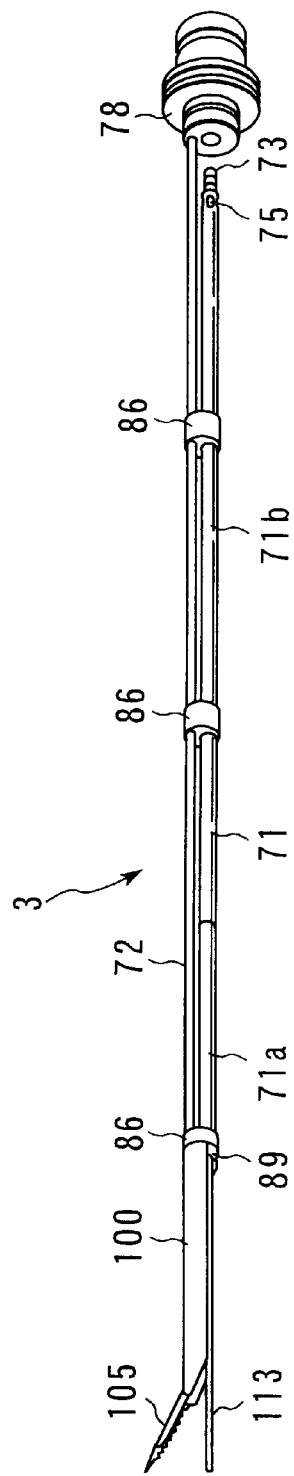
FIG. 2B is a perspective view of a probe unit.

As shown in FIG. 2A, the handle unit 2 is provided with a front handle 13, fixed to an operating section body 12 having a vibrator connecting portion 11, and a rockable rear handle 14. An operating end portion of the front handle 13 is provided with a finger hole 15 into which a plurality of fingers other than the thumb can be inserted selectively, while an operating end portion of the rear handle 14 is provided with a finger hole 16 to which the thumb of the same hand is to be anchored. The rear handle 14 is pivotally mounted for rotation on a pivot 17 that is screwed to the operating section body 12.

As shown in FIGS. 2 and 5, a fixing screw member 19, which doubles as a retaining pin, is provided penetrating the other end of the rear handle 14. As shown in FIG. 5, the inner end of the fixing screw member 19 is provided with an engaging portion 21 that is caused to engage the probe unit 3, while an operating knob portion 22 is formed on the other end of the fixing screw member 19.

A loose fitting portion 24 is formed on the intermediate portion of the fixing screw member 19. The loose fitting portion 24 of the fixing screw member 19 is loosely passed through a through hole 23 that is formed in the other end portion of the rear handle 14. Further, the intermediate portion of the fixing screw member 19 is formed with an external thread portion 26, which is situated on the outer end side of the loose fitting portion 24 and mates with an internal thread portion 25 that is formed in the through hole 23. The fixing screw member 19 can freely move forward and backward within a range such that its loose fitting portion 24 is situated in the through hole 23. Accordingly, the engaging portion 21 can be evacuated from a position where it engages a rotor, which will be mentioned later. Further, the engaging portion 21 can be fixed in the position of engagement with the rotor by advancing the fixing screw member 19 to the engagement position of the engaging portion 21 so that the external thread portion 26 is screwed into the internal thread portion 25.

The fixing screw member 19 is wound with a spring member, e.g., a coil spring 28, which is situated between the operating knob portion 22 and the rear handle 14. If the external thread portion 26 is disengaged from the internal thread portion 25, as shown in FIG. 6B, the fixing screw member 19 is automatically evacuated by the agency of the elastic restoring force of the coil spring 28, as shown in FIG.

5. Thus, insertion/attachment and disassembly/removal operations for the probe unit 3 cannot be hindered.

Further, a stopper piece 29 for fixing the probe unit 3 to be attached to the operating section body 12 in its attachment position is pivotally mounted on the top portion of the body 12. The stopper piece 29 may be formed of a metal for improved durability or an electrical insulating material to secure electrical insulating properties. The stopper piece 29 is urged by means of a spring 30 to rock in a direction such that it engages the probe unit 3, and normally, is rocked in the direction shown in FIG. 4A to be on standby.

Figures 4A, 4B:
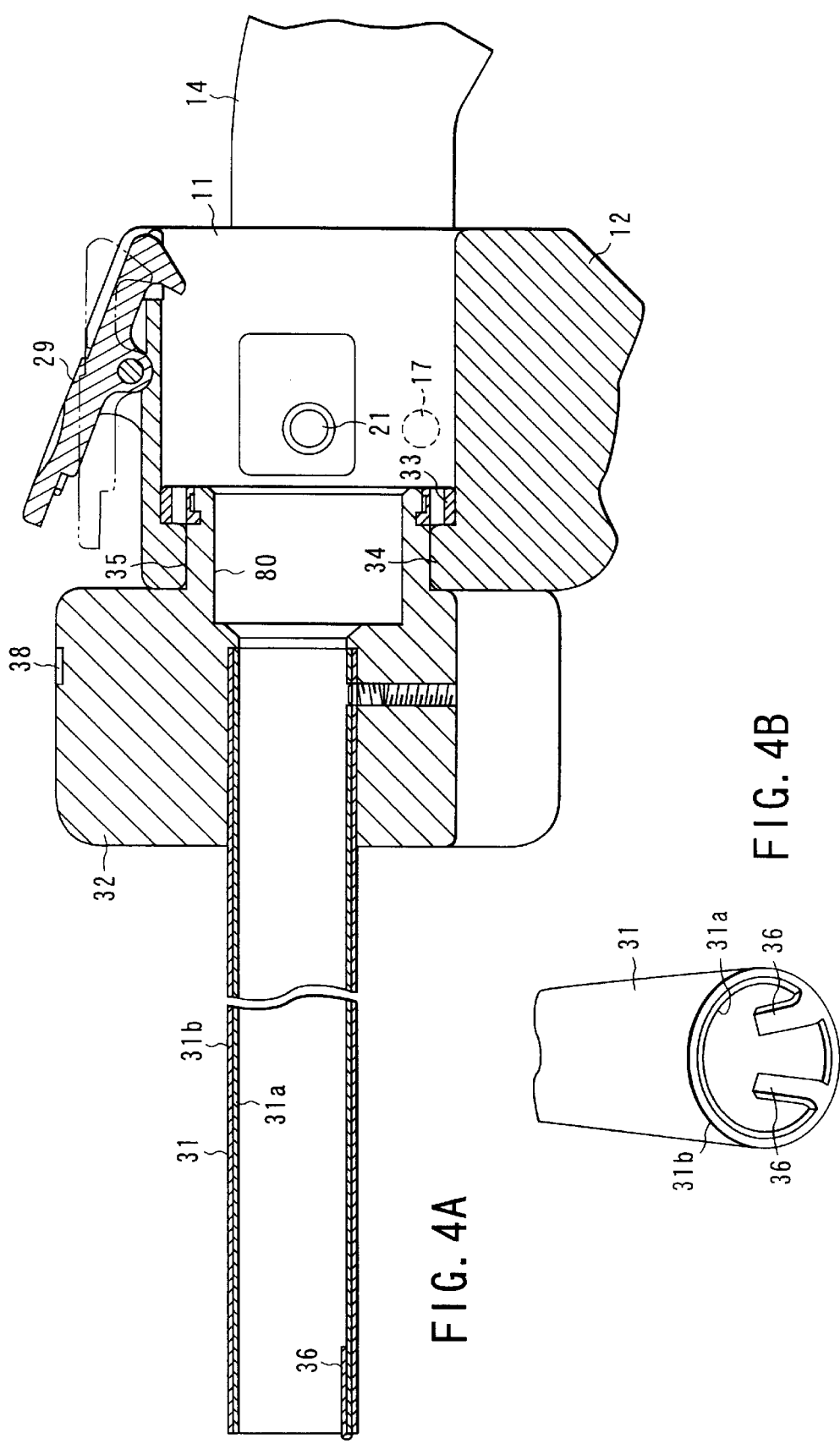
FIG. 4A is a profile of the handle unit of the ultrasonic coagulating/cutting apparatus of the first embodiment.
FIG. 4B is a perspective view showing retaining pieces at the distal end portion of an insertable sheath section.

As shown in FIG. 4A, an insertable sheath section 31 is coupled to the front end of the operating section body 12 by means of the member of a rotary knob 32 and a fixing nut 33. The insertable sheath section 31 and the rotary knob 32 are coaxially mounted on the operating section body 12 for rotation. More specifically, the rotary knob 32 is rotatably supported by means of bearing means 35, which is constructed in a manner such that a collar 34 formed on the operating section body 12 is held between the rotary knob 32 and the fixing nut 33. The insertable sheath section 31 is continually braked in some measure by means of the frictional force of its sliding-contact portion, and cannot rotate easily. If the front handle 13 and the rear handle 14 are gripped tight, however, frictional force between them increases, so that the section 31 is braked. Thus, braking means is incorporated to prevent the rotation of the insertable sheath section 31 securely.

As shown in FIG. 4A, the insertable sheath section 31 has a dual-pipe structure including a core 31a, formed of a stiff metallic pipe, and a skin 31b of an electrical insulating resin covering the core 31a. As shown in FIG. 4B, a distal end portion in the insertable sheath section 31 is provided with a pair of retaining pieces 36 capable of engaging the probe unit 3 that is passed through the same.

The retaining pieces 36 are formed by partially extending the member of the core 31a and bending it inward. Corresponding to this retaining position, an index 38 indicative of the retaining position is provided on the top surface portion of the rotary knob 32. If the probe unit 3 is inserted into the operating section body 12 with the index 38 upward, a part of a jaw retaining member (mentioned later) on the distal end of the probe unit 3 engages the retaining pieces 36, and at the same time, the stopper piece 29 fixes that portion of the vibrator unit 4 which corresponds to a hand piece 41 in its attachment position.

The vibrator unit 4 is constructed in the manner shown in FIG. 7A. More specifically, an ultrasonic vibrator 43 is located in a cylindrical cover 42 of the hand piece 41. A horn 44 is coupled to the front end of the ultrasonic vibrator 43. As shown in FIG. 7B, the distal end of the horn 44 is formed having an internal thread portion 45 into which the rear end of the probe unit 3 is screwed.

The ultrasonic vibrator 43 is held in the cover 42 with its horn 44 supported on the front end portion of the cover 42. More specifically, the horn 44 is held in a manner such that its outer collar 46 is fitted tight in the inner periphery of the cover 42 and is held and fixed between an inner collar 47 formed on the inner periphery of the cover 42 and a fixing ring 48 that is screwed into the cover 42.

As shown in FIG. 7B, an engaging socket portion 51, a notched recess, is formed in a part of the outer collar 46 of the horn 44. The inner collar 47 of the cover 42 is formed with an engaging portion 52, a projection, which is fitted in the engaging socket portion 51 for engagement. Further, cushion members 53 of an elastic material are axially interposed between the outer collar 46 of the horn 44, the inner collar 47 of the cover 42, and the fixing ring 48. The outer collar 46 of the horn 44 is held and clamped by means of the cushion members 53.

As shown in FIG. 7A, moreover, the front end portion of the cover 42 is formed having a tapped hole 42a. A ring-shaped stopper receiving member 56 is formed with an external thread portion 56a that mates with the tapped hole 42a. As the external thread portion 56a of the stopper receiving member 56 is screwed into the tapped hole 42a of the cover 42, the stopper receiving member 56 is fixedly attached to the front end portion of the cover 42.

An annular circumferential groove 57 is formed on the outer peripheral surface portion of the stopper receiving member 56. The stopper piece 29 on the side of the handle unit 2 can be fitted in and retained by the stopper receiving member 56. The rear end portion of a rotor 78 of the probe unit 3 can be fitted in a bore 58 of the stopper receiving member 56.

The ultrasonic vibrator 43 is composed of a Langevin ultrasonic vibrator shown in FIG. 7B. The Langevin ultrasonic vibrator includes a plurality of piezoelectric devices 61 that are stacked in layers. A laminate of these piezoelectric devices 61 is located between the horn 44 and a backside member 62, and is tightened by means of a bolt (not shown) that penetrates its central portion. Further, electrodes 63 are interposed between the piezoelectric devices 61, individually. A driving voltage is applied to the piezoelectric devices 61 through the electrodes 63.

A lead wire 65 from a hand piece cord 64 is connected to the electrodes 63. Another lead wire 66 is further connected to the ground-side electrodes 63. The lead wire 66 is connected to a high-frequency connecting pin 67. The connecting pin 67 can be connected with a high-frequency supply cord (not shown) that connects with a high-frequency power source. The ground-side electrodes 63 electrically connect with electrically conductive bolts of the ultrasonic vibrator 43 and the horn 44 that is also electrically conductive.

A vibration transmitting member and a probe (mentioned later) of the probe unit 3 that are connected to the distal end of the horn 44 are also electrically conductive members, and these members help electrical conduction to a distal treatment portion.

Figure 3:
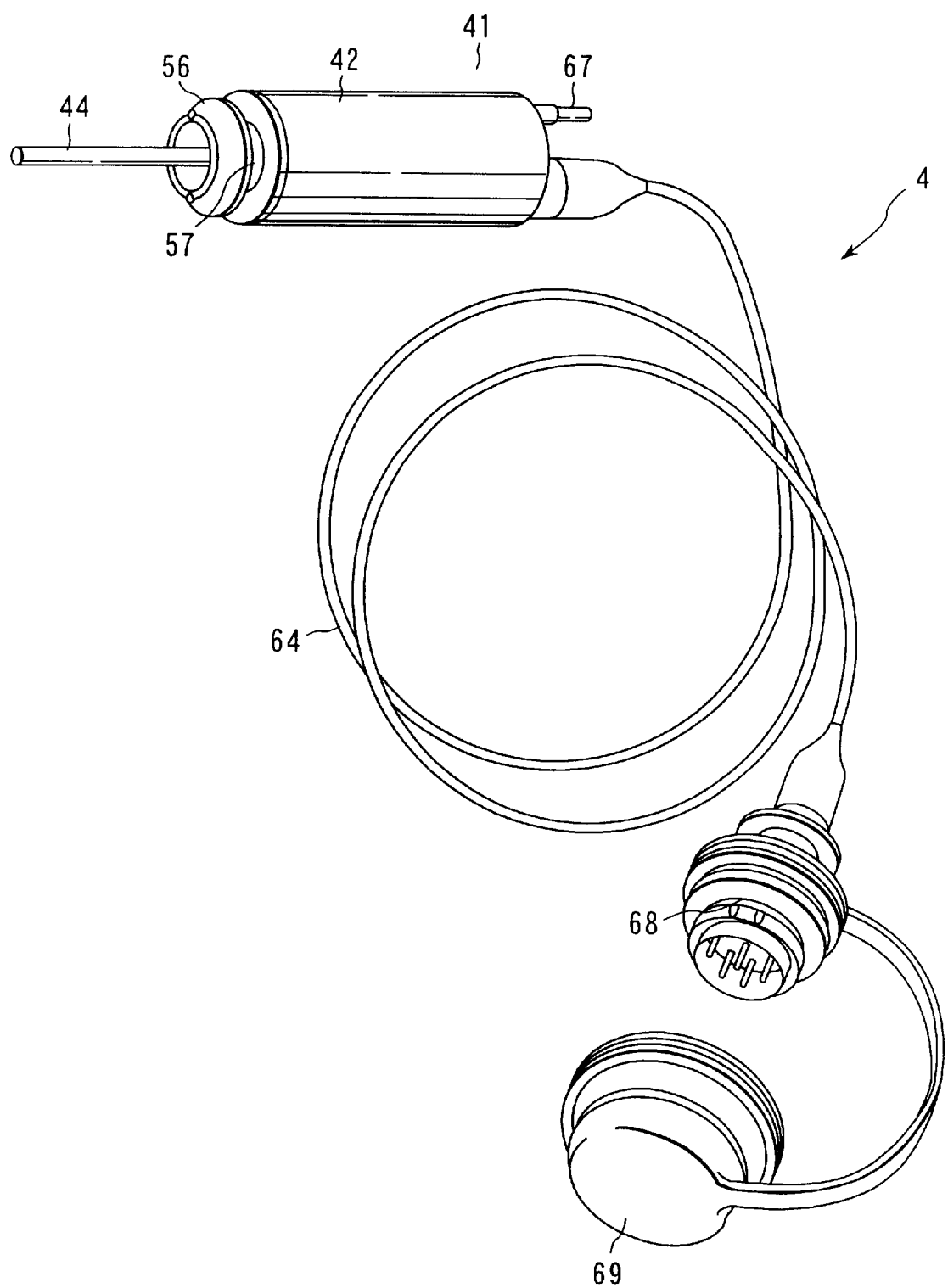
FIG. 3 is a perspective view of a vibrator unit of the ultrasonic coagulating/cutting apparatus of the first embodiment.

As shown in FIG. 3, the hand piece cord 64 is elongated and flexible. A hand piece plug 68 is provided on the extended distal end of the hand piece cord 64. A detachable waterproof cap 69 is attached to the hand piece plug 68. In cleaning the vibrator unit 4, a region near a terminal portion of the hand piece plug 68 is covered by means of the waterproof cap 69.

The probe unit 3 is formed in the manner shown in FIGS. 8A to 10H. More specifically, the probe unit 3 includes a vibration transmitting member 71 for transmitting ultrasonic vibration and an operation drive shaft 72 that is located substantially parallel to the same. The vibration transmitting member 71, which has a high acoustic effect, is formed of a titanium or aluminum material that is highly adaptive to living organisms.

The vibration transmitting member 71 is formed of two bodies, a distal-end-side portion 71a and a rear-end-side portion 71b, which are fixedly coupled to each other by screwing and adhesive bonding. As shown in FIG. 9B, an external thread portion 73 is formed on the rear end portion of the vibration transmitting member 71. The external thread portion 73 can be screwed into an internal thread portion 45 that is formed on the distal end of the horn 44. The external thread portion 73 can be firmly coupled by being screwed into a position such that a stepped end face 74 at the rear end of the vibration transmitting member 71 abuts against the distal end face of the horn 44.

Spanner catch faces 75 are formed on the peripheral surface of the rear end portion of the vibration transmitting member 71. An opening portion of a spanner (mentioned later) can be engagedly anchored to the spanner catch faces 75.

The operation drive shaft 72 is a wire-shaped member formed of stainless steel (SUS) or some other material that is relatively stiff and has spring elasticity. Further, a thin-walled metallic pipe 76 is fitted on the operation drive shaft 72. The pipe 76 is fitted ranging from the proximal end of the operation drive shaft 72 to a middle portion short of the distal end. The pipe 76 is bonded to the peripheral surface of the operation drive shaft 72. As shown in FIGS. 8B and 10F, a small notch 77 is formed in a suitable portion of the pipe 76. The pipe 76 and the shaft 72 are bonded with an adhesive agent that is introduced through the opening of the notch 77.

As shown in FIG. 9B, the rotor 78 is fixedly attached to the rear end of the operation drive shaft 72. The rotor 78 is formed in the shape of a cylindrical rotating body having a central axis in alignment with the central axis of the vibration transmitting member 71.

Two collars 81 are provided on the outer periphery of the rotor 78, and an annular groove 82 for engagement is formed between these two collars 81. The engaging portion 21 of the fixing screw member 19, which is attached to the rear handle 14, a movable handle of the handle unit 2, is fitted in the annular groove 82 for engagement.

O-rings 83 and 84 are fitted individually on front and rear peripheral surface portions of the annular groove 82 for engagement. When the units 2, 3 and 4 are assembled, a front-end-side peripheral portion 85 of the rotor 78 is fitted into a fitting hole portion 80 of the handle unit 2, and a rear-end-side peripheral portion 87 of the rotor 78 is fitted into the bore 58 of the stopper receiving member 56 in the bore of the operating section body 12.

Further, the stopper piece 29 can engage the circumferential groove 57 of the stopper receiving member 56 on the side of the vibrator unit 4. Thereupon, the vibrator unit 4 is allowed to rotate integrally with the probe unit 3. Further, by handle operation by means of the handle unit 2, the operation drive shaft 72 of the probe unit 3 can be moved integrally with the rotor 78 in the longitudinal direction with respect to the vibrator unit 4 and the vibration transmitting member 71, stationary members.

As shown in FIG. 9A, the vibration transmitting member 71 and the operation drive shaft 72 are coupled to each other by means of a plurality of spacers 86. Each attached spacer 86 is situated corresponding to a node of vibration of the vibration transmitting member 71.

The spacer 86 is provided with a fitting groove 87 in which an intermediate portion of the vibration transmitting member 71 is slidably fitted and a support hole (fitting groove) 88 that penetrates the operation drive shaft 72 having the pipe 76 thereon. These spacers 86 serve to keep the vibration transmitting member 71 and the operation drive shaft 72 parallel to each other with a given space between them.

Further, the pipe 76 that is fitted on the operation drive shaft 72 is provided with retaining rings 89 that are put on the pipe 76 so as to be situated individually before and behind their corresponding spacers 86, among all other spacers 86 except the foremost one, in order to prevent the spacers 86 from moving back and forth. Each retaining ring 89 is fixed to the outer periphery of the pipe 76 by adhesive bonding. The retaining ring 89 is formed having a slit 90 into which the adhesive agent is to be poured.

The foremost spacer 86 is located in the position of a node of ultrasonic vibration that is nearest to the far end of a probe 113, which will be mentioned later. The foremost spacer 86 is put on the outer periphery of the pipe 76 on the operation drive shaft 72 so as to be movable in the axial direction of the pipe. The foremost spacer 86 may be fixed by being bonded to the outer periphery of the pipe 76.

As shown in FIG. 10E, moreover, the spacer 86 is provided with a support member 89. A retaining ring 91 is fitted on the spacer 86 and the support member 89 to couple the two, and is integrally fixed by adhesive bonding. More specifically, that portion of the vibration transmitting member 71 which corresponds to a flange 95 (mentioned later) is held between the spacer 86 and the support member 89 from above and below. In this state, the retaining ring 91 is fitted on and fastened to the spacer 86 and the support member 89, and the spacer 86 and the retaining ring 91 are bonded together. The support member 89 is a member that is included in the spacer 86, and these two members may alternatively be fixed by adhesive bonding.

As shown in FIG. 10D, the vibration transmitting member 71 is formed having the rotation restraining flange 95 in a position corresponding to the foremost spacer 86. The profile of the rotation restraining flange 95 is a substantially rectangular irregular shape. The inner surface portion of the foremost spacer 86 is formed with an inlaying groove 96 that has the same shape as the rotation restraining flange 95. The rotation restraining flange 95 is engagedly fitted into the inlaying groove 96 of the foremost spacer 86, whereby the spacer 86 can be restrained from rocking around the axis of the vibration transmitting member 71.

Further, a cushion member 97 of a vibration absorbing material, e.g., rubber, is fitted in the inlaying groove 96 of the spacer 86 on the side of the operation drive shaft 72. The cushion member 97 is located between the rotation restraining flange 95 and the spacer 86.

The foremost spacer 86 doubles as a support portion for a jaw retaining member 100 that extends forward from its position. The spacer 86 and the jaw retaining member 100 are formed integrally with each other. Thus, the jaw retaining member 100 is restrained from moving in the axial direction of the vibration transmitting member 71 and from rocking around the axis of the member 71.

Further, the so-called stationary blade 113 having an elongated profile is formed on the distal end portion of the vibration transmitting member 71 by directly using the vibration transmitting member 71. The peripheral surface portion of the distal end of this probe 113 is rounded.

Figure 11:
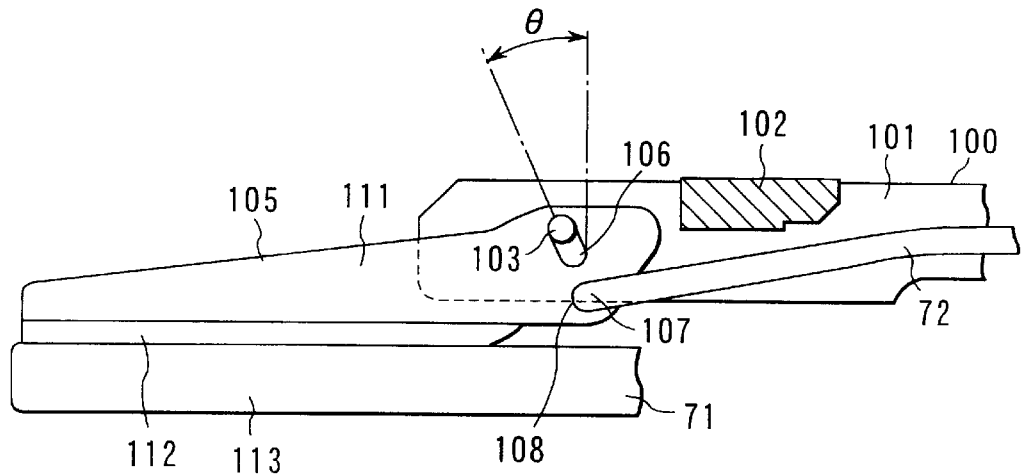
FIG. 11 is a view illustrating a distal treatment portion of the probe unit of the first embodiment.
Figure 12A:
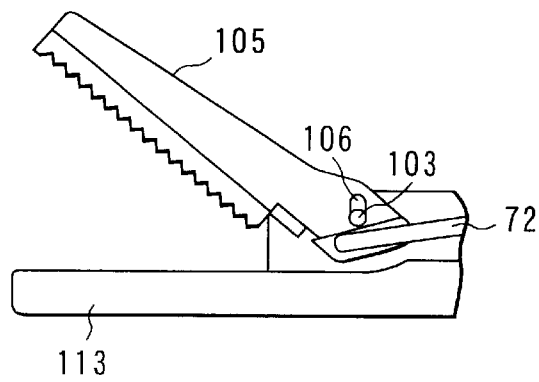
FIG. 12A is a profile of a principal part showing the distal treatment portion of the probe unit of the first embodiment open in its maximum opening position.
Figure 12B:
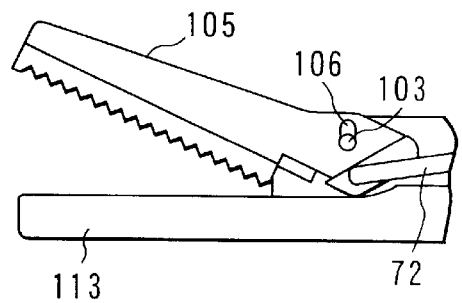
FIG. 12B is a profile of the principal part showing the distal treatment portion of the probe unit of the first embodiment open in its medium opening position.
Figure 12C:
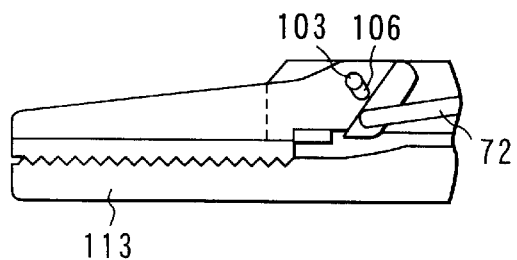
FIG. 12C is a profile of the principal part showing the distal treatment portion of the probe unit of the first embodiment closed.

As shown in FIG. 11, moreover, the front end of the jaw retaining member 100 extends to a position short of the distal end of the vibration transmitting member 71. A jaw 105 (mentioned later) can be coupled to the distal end portion of the jaw retaining member 100.

Further, the jaw retaining member 100 is formed having a slit 101 that extends from its proximal end portion to the distal end, as shown in FIG. 10C. A reinforcing bridge 102 for coupling the left- and right-hand portions of the slit 101 is provided at the distal end portion of the jaw retaining member 100 (see FIG. 10B).

At the distal end portion of the jaw retaining member 100, a pivot 103 is located bridging the left- and right-hand side portions of the slit 101 on the distal end side of the reinforcing bridge 102. The jaw 105, which constitutes a so-called movable blade that faces the stationary probe 113, is pivotally mounted on the pivot 103. As shown in FIG. 11, the jaw 105 is composed of a base 111 and a contact member 112, which are integrally with each other.

At the distal end portion of the jaw retaining member 100, moreover, a bearing connecting hole 106 of the jaw 105, which is formed of an oblique slot, as shown in FIG. 8A, is formed in each of left- and right- hand side portions of the slit 101. The pivot 103 is fitted in the connecting hole 106.

As shown in FIG. 11, furthermore, the distal end of the operation drive shaft 72 is coupled to that part of the proximal end portion of the jaw 105 which is situated under the connecting hole 106. The distal end portion of the operation drive shaft 72 is bent substantially at right angles, and its bent portion 107 is fitted into and rockably coupled to a hole 108 in the jaw 105 from the side face of the jaw 105.

The length (width) of the bent portion 107 is a little shorter than the with of the slit 101 shown in FIG. 10A, and the bent portion 107 is provided so that it is always situated in the slit 101. If the bent portion 107 is broken at the base, therefore, it can be held in the hole 108 of the jaw 105, and its fragments never drop into the body cavity or the like.

The jaw 105 can be rocked opposite the probe 113 by pushing or pulling the operation drive shaft 72. Thus, the jaw 105 and the probe 113 constitute an open-close ultrasonic treatment unit that can grasp an organism tissue. FIG. 8A shows a state in which the jaw 105 is closed by pulling the operation drive shaft 72. In this state, the contact member 112 of the jaw 105 is entirely in contact with the top surface of the probe 113.

The connecting hole 106 of the jaw 105 is in the form of a slot. The width of the connecting hole 106 is adjusted to a size such that pivot 103 fitted in the connecting hole 106 is movable. As shown in FIG. 11, moreover, the longitudinal direction (L1) of the connecting hole 106 is inclined at an angle θ to a line L2 that is normal to the grip face of the probe 113. If the longitudinal direction L1 of the connecting hole 106 is inclined in this manner, the engagement of the jaw 105 with the probe 113 is improved. Thus, the pivot 103 is relatively movable in the connecting hole 106 of the jaw 105, so that the process of operation during which the jaw 105 uniformly engages the probe 113 to grasp the organism tissue lengthens, and closing impact for seizure becomes generally uniform.

In the case of this embodiment, the angle θ of inclination of the connecting hole 106 is adjusted to a value greater than 0° and smaller than 90°. Preferably, the angle θ should be at 45° or less. If the angle θ is adjusted to 12°±10°, in particular, the grip force is substantially uniform on the distal end side of the jaw 105 and on the hand side.

The relation between the pivot 103 and the connecting hole 106 for supporting the jaw 105 may be changed so that the pivot 103 and the connecting hole 106 are provided or formed on the sides of the jaw 105 and the jaw retaining member 100, respectively. The same effects as aforesaid can be obtained also in this case.

Figure 13:
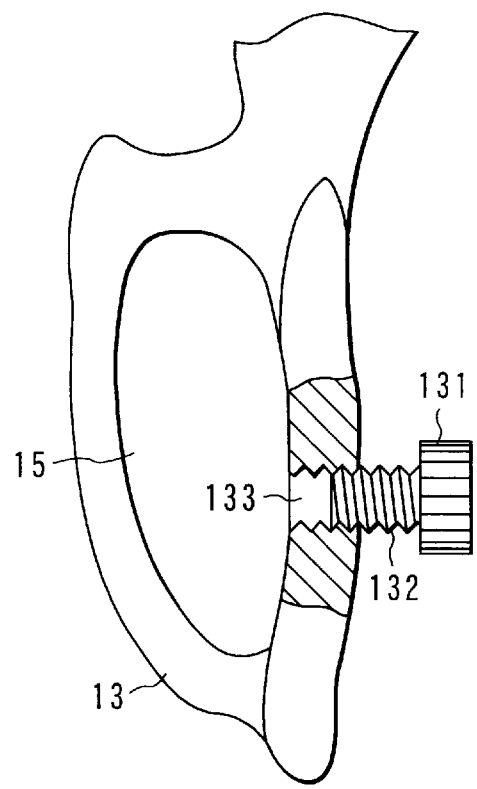
FIG. 13 is a side view, partially in section, showing the way a stopper of a front handle of the first embodiment is attached.

As shown in FIG. 13, moreover, the front handle 13 of the ultrasonic coagulating/cutting apparatus 1 of the present embodiment is formed having a tapped hole 133 for stopper attachment on the side opposite to the rear handle 14. An external thread portion 132 that protrudes from a stopper (switching member) 131 for grip force adjustment is screwed in the tapped hole 133. The rocking end position of the rear handle 14 can be regulated by butting the rear handle 14 against the stopper 131. The projection of the stopper 131 from the front handle 13 toward the rear handle 14 can be adjusted by changing the depth of threaded engagement of the external thread portion 132 with the tapped hole 133. By adjusting the projection of the stopper 131, moreover, the grip force for the organism tissue held between the jaw 105 and the probe 113 can be adjusted freely.

The following is a description of the operation of the arrangement described above. In operating the ultrasonic coagulating/cutting apparatus 1 of the present embodiment, the jaw 105 of the distal treatment portion can be opened or closed by grasping the handles 13 and 14 of the handle unit 2 with one hand and rocking the rear handle 14.

In doing this, the operation drive shaft 72 is pulled to the hand side as the rear handle 14 is rocked in the clockwise direction of FIG. 1 around the pivot 17. Thus, the jaw 105 rocks in the closing direction with respect to the stationary-side probe 113, whereupon the organism tissue can be held between them.

As the rear handle 14 is rocked in the counterclockwise direction of FIG. 1 around the pivot 17, moreover, the operation drive shaft 72 is pushed to the distal end side. Accordingly, the jaw 105 rocks in the direction to move away from the stationary-side probe 113 (or to open). With the jaw 105 kept closed, for example, the jaw 105 and the probe 113 are inserted between organism tissues that adhere closely one another, and thereafter, an operation to separate an internal organ or the like can be carried out by opening the jaw 105.

In conducting ultrasonic treatment, moreover, the apparatus is guided into the abdomen by utilizing a trocar or the like, and the organism tissue of an affected part is held between the probe 113 and the jaw 105 of the distal treatment portion. When ultrasonic vibration is applied to the probe 113, the grasped organism tissue portion is coagulated and cut.

In the case where the aforesaid ultrasonic coagulating/cutting process is carried out by means of the ultrasonic coagulating/cutting apparatus 1 of the present embodiment, furthermore, the depth of threaded engagement of the external thread portion 132 of the stopper 131 with the tapped hole 133 of the front handle 13 is previously changed to adjust the projection of the stopper 131, whereby the grip force for the organism tissue held between the jaw 105 and the probe 113 can be adjusted freely.

If the projection of the stopper 131 is substantial (or if the depth of threaded engagement of the external thread portion 132 of the stopper 131 is small), the distance covered by the rear handle 14 that rocks from its fully-open position to its fully-closed position where it abuts against the stopper 131, as the jaw 105 is closed by means of the handle unit 2, is short. Accordingly, the grip force for the organism tissue held between the jaw 105 and the probe 113 as the jaw 105 is closed in a manner such that the operation drive shaft 72 is pulled to the hand side as the rear handle 14 is rocked in the clockwise direction of FIG. 1 around the pivot 17 is relatively small.

Figure 14A:
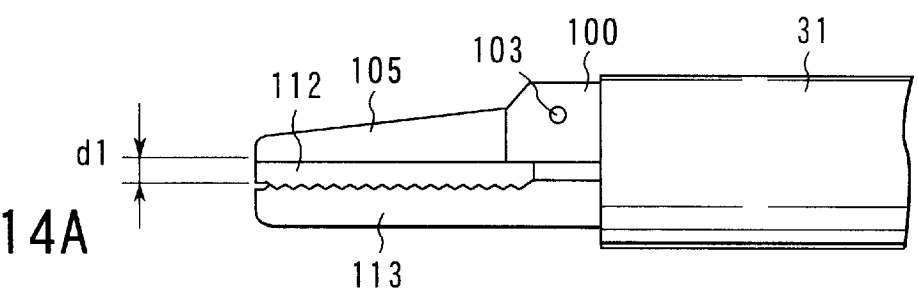
FIG. 14A is a side view of the distal treatment portion showing a probe of the first embodiment bent to a low degree.

In this case, the movement of the probe 113 from the position where the jaw 105 and the probe 113 start to touch each other to the fully-closed position where the rear handle 14 abuts against the stopper 131, that is, a deflection d1 of the probe 113, decreases during the rocking motion of the rear handle 14, as shown in FIG. 14A. In this state, the cutting time during which the organism tissue held between the jaw 105 and the probe 113 is cut in the ultrasonic coagulating/cutting process becomes longer, so that the range of coagulation of the organism tissue is widened.

Figure 14B:
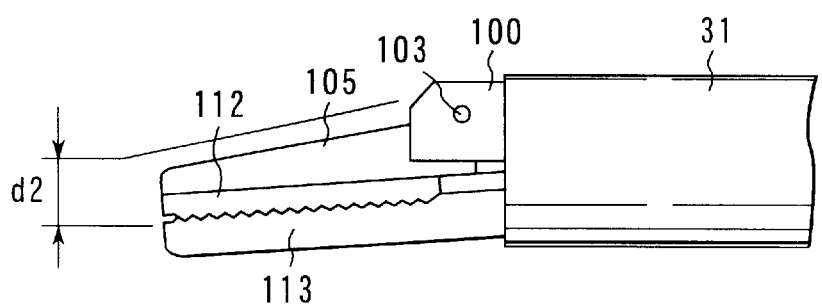
FIG. 14B is a side view of the distal treatment portion showing the probe bent to a high degree.

If the projection of the stopper 131 is small (or if the depth of threaded engagement of the external thread portion 132 of the stopper 131 is substantial), the distance covered by the rear handle 14 that rocks from its fully-open position to its fully-closed position where it abuts against the stopper 131, as the jaw 105 is closed by means of the handle unit 2, is long. Accordingly, the grip force for the organism tissue held between the jaw 105 and the probe 113 as the jaw 105 is closed in a manner such that the operation drive shaft 72 is pulled to the hand side as the rear handle 14 is then rocked is relatively great. In this case, a deflection d2 of the probe 113 increases during the rocking motion of the rear handle 14, as shown in FIG. 14B. In this state, the cutting time during which the organism tissue held between the jaw 105 and the probe 113 is cut in the ultrasonic coagulating/cutting process becomes shorter, so that the range of coagulation of the organism tissue is narrowed.

Accordingly, the present embodiment has the following effects. More specifically, the force to hold the organism tissue between the jaw 105 and the probe 113 as the rear handle 14 of the handle unit 2 is rocked to close the jaw 105 can be adjusted by changing the depth of threaded engagement of the external thread portion 132 of the stopper 131 with the tapped hole 133 of the front handle 13, thereby freely adjusting the projection of the stopper 131. Therefore, an operator can obtain appropriate coagulating/cutting performance by freely adjusting the projection of the stopper 131 of the front handle 13 according to the kind and thickness of the organism tissue. Thus, the operation for the coagulation or coagulative incision of the organism tissue requires no special experience or skill, and besides, stable handle operation can be carried out with little possibility of entailing variation in the finish of treatment.

According to the present embodiment, moreover, the external thread portion 132 of the stopper 131 is screwed into the tapped hole 133 for attachment that is formed in the front handle 13, so that the construction of an adjusting mechanism for adjusting the grip force for the organism tissue can be simplified.

FIGS. 15A to 17B show an ultrasonic coagulating/cutting apparatus 141 of a second embodiment of the present invention. The ultrasonic coagulating/cutting apparatus 141 of the present embodiment is obtained by modifying the arrangement of the handle unit 2 of the ultrasonic coagulating/cutting apparatus 1 of the first embodiment (see FIGS. 1 to 14B) in the following manner. For other parts, the ultrasonic coagulating/cutting apparatus 141 is constructed in the same manner as the ultrasonic coagulating/cutting apparatus 1 of the first embodiment. Like numerals are used to designate like portions that are shared with the ultrasonic coagulating/cutting apparatus 1 of the first embodiment, and a description of those portions is omitted.

A handle unit 142 of the ultrasonic coagulating/cutting apparatus 141 of the present embodiment is provided with a stationary handle 143 and a movable operating handle 144. An operating end portion of the stationary handle 143 is provided with a finger hole 145 into which a plurality of fingers other than the thumb can be inserted selectively, while an operating end portion of the movable operating handle 144 is provided with a finger hole 146 to which the thumb of the same hand is to be anchored.

Figures 15A, 15B:
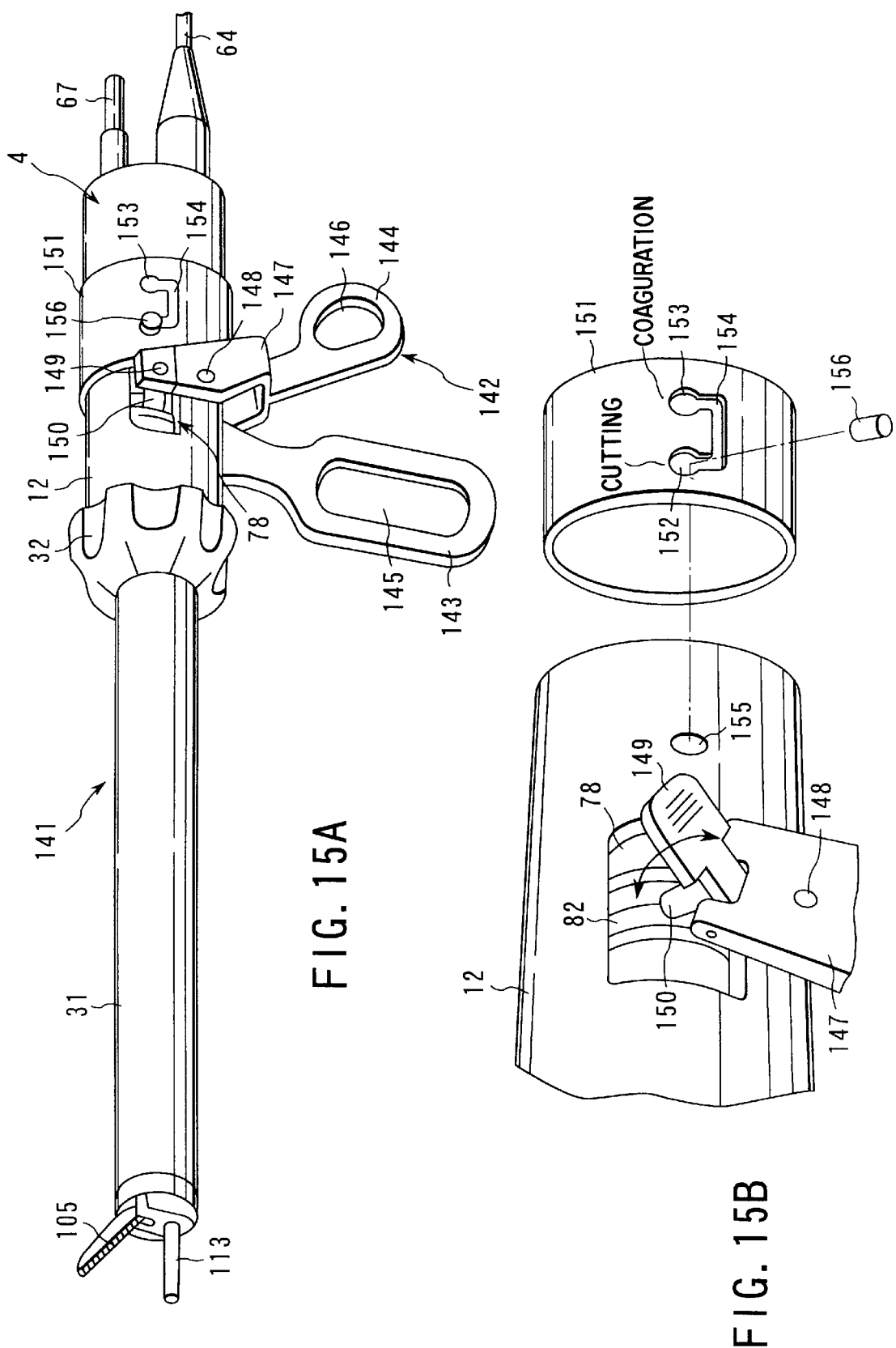
FIG. 15A is a general perspective view of an ultrasonic coagulating/cutting apparatus showing a second embodiment of the present invention.
FIG. 15B is an exploded perspective view showing the way a grip force adjusting ring is attached.

As shown in FIG. 15B, moreover, a substantially U-shaped connecting arm 147 is provided on the upper end portion of the movable operating handle 144. A substantially vertically central part of the connecting arm 147 is rockably mounted on an operating section body 12 by means of a handle pivot 148.

Further, a retainer 149 shown in FIG. 15B is provided on the upper end portion of the connecting arm 147 of the movable operating handle 144 so as to be rockable toward a central axis that is accessible through a window portion of the operating section body 12. A retaining claw 150 protrudes from the retainer 149. The retaining claw 150 is removably anchored to an annular groove 82 for engagement of a rotor 78 in the operating section body 12.

By swinging the movable operating handle 144 toward the stationary handle 143, an operation drive shaft 72 of a probe unit 3 can be moved integrally with the rotor 78 in the longitudinal direction with respect to a vibrator unit 4 and a vibration transmitting member 71, stationary members, and a jaw 105 can be rocked with respect to a probe 113.

According to the present embodiment, moreover, a stopper ring 151 for use as moved position switching means for the jaw 105 for switching the moved position of the jaw 105 during operation to close the jaw 105 is mounted on the outer peripheral surface of the operating section body 12 for rocking motion and axial movement. The stopper ring 151 is mounted on the path of transfer of the retainer 149 at the upper end portion of the movable operating handle 144 on the outer peripheral surface of the operating section body 12 so as to be able to engage the movable operating handle 144.

As shown in FIG. 15B, the stopper ring 151 is formed having retaining holes 152 and 153 in two positions, front and rear, in the axial direction. For example, "CUTTING" and "COAGULATION" are marked in positions near the front retaining hole 152 and the rear retaining hole 153, respectively. Further, these retaining holes 152 and 153 are coupled to each other by means of a substantially U-shaped guide groove 154.

Furthermore, a pin fixing hole 155 is formed behind the window portion in the outer peripheral surface of the operating section body 12. A retaining pin 156 of the stopper ring 151 is fixed to the pin fixing hole 155. The retaining pin 156 is fitted in the guide groove 152 of the stopper ring 151. The retaining pin 156 can be caused alternatively to engage one of the retaining holes 152 and 153 by moving the stopper ring 151 along the outer peripheral surface of the operating section body 12 in a manner such that the retaining pin 156 is moved along the guide groove 152 of the stopper ring 151.

Figure 16A:
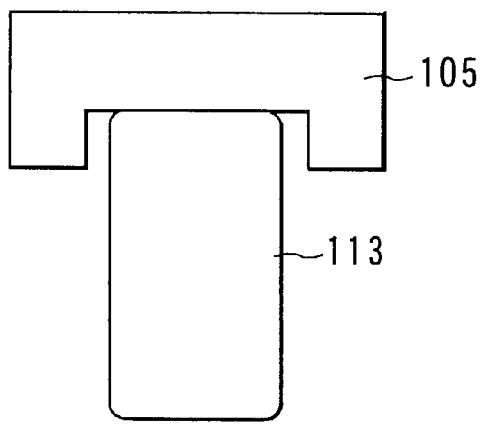
FIG. 16A is a profile of a principal part for illustrating a moved state of a jaw for the incision of an organism tissue by means of the ultrasonic coagulating/cutting apparatus of the second embodiment.

When the retaining pin 156 is in engagement with the front retaining hole 152, the front end of the stopper ring 151 is located in an end position in the path of transfer of the retainer 149 at the upper end portion of the movable operating handle 144. In this state, the jaw 105 is rocked to an end position where it engages the probe 113 as shown in FIG. 16A when the retainer 149 at the upper end portion of the movable operating handle 144 engages the stopper ring 151 as the movable operating handle 144 is rocked toward the stationary handle 143.

Figure 16B:
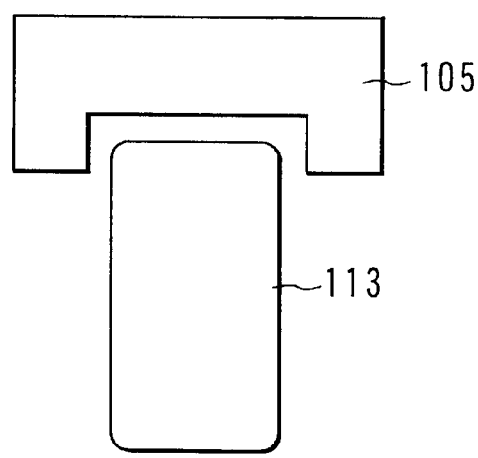
FIG. 16B is a profile of the principal part for illustrating a moved state of the jaw for the coagulation of the organism tissue.

When the retaining pin 156 is in engagement with the rear retaining hole 153, moreover, the front end of the stopper ring 151 is located ahead of the end position in the path of transfer of the retainer 149 at the upper end portion of the movable operating handle 144. In this state, the jaw 105 is kept stopped from rocking in a halfway position short of the position where it engages the probe 113 as shown in FIG. 16B when the retainer 149 at the upper end portion of the movable operating handle 144 engages the stopper ring 151 as the movable operating handle 144 is rocked toward the stationary handle 143.

Thus, by freely selecting and setting set positions for the stopper ring 151, that is, positions where the retaining pin 156 and the two retaining holes 152 and 153 are in engagement, the operating position can be easily switched between a cutting position for cutting the organism tissue and a coagulating position such that the jaw 105 is stopped at the halfway position short of the cutting position.

Figure 17A:
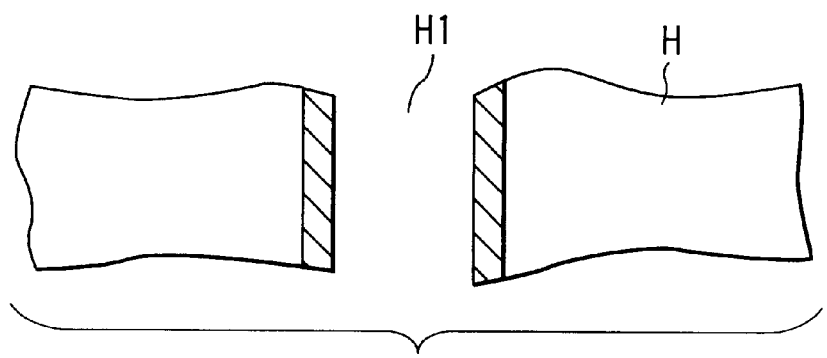
FIG. 17A is a profile of a principal part for illustrating the state of the organism tissue cut by means of the ultrasonic coagulating/cutting apparatus of the second embodiment.

The following is a description of the operation of the arrangement described above. In operating the ultrasonic coagulating/cutting apparatus 141 of the present embodiment, the stopper ring 151 is set alternatively to the organism tissue cutting position or the organism tissue coagulating position in advance. If the stopper ring 151 is set in the organism tissue cutting position, the front end of the stopper ring 151 is expected to be located in the end position in the path of transfer of the retainer 149 at the upper end portion of the movable operating handle 144. If the movable operating handle 144 is rocked toward the stationary handle 143 in this state, therefore, the jaw 105 is rocked to the end position where it engages the probe 113 as shown in FIG. 16A when the retainer 149 at the upper end portion of the movable operating handle 144 engages the stopper ring 151. Thus, in this case, an organism tissue H held between the probe 113 and the jaw 105 can be securely cut to form a cut portion H1 in the ultrasonic treatment, as shown in FIG. 17A.

Figure 17B:
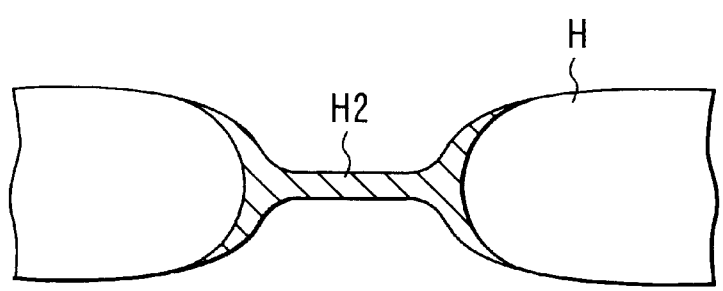
FIG. 17B is a profile of the principal part for illustrating the coagulated state of the organism tissue.

If the stopper ring 151 is set in the organism tissue coagulating position, moreover, the front end of the stopper ring 151 is expected to be located ahead of the end position in the path of transfer of the retainer 149 at the upper end portion of the movable operating handle 144. If the movable operating handle 144 is rocked toward the stationary handle 143 in this state, therefore, the jaw 105 is kept stopped from rocking in the halfway position short of the position where it engages the probe 113 as shown in FIG. 16B when the retainer 149 at the upper end portion of the movable operating handle 144 engages the stopper ring 151. Thus, in this case, a coagulated portion H2 can be formed without cutting the organism tissue H that is held between the probe 113 and the jaw 105 in the ultrasonic treatment, as shown in FIG. 17B.

Accordingly, the above-described arrangement provides the following effects. More specifically, in the ultrasonic coagulating/cutting apparatus 141 of the present embodiment, the stopper ring 151 is provided on the outer peripheral surface of the operating section body 12, and the operating position is easily switched between the cutting position for cutting the organism tissue and the coagulating position where the jaw 105 is stopped at the halfway position short of the cutting position by freely selecting and setting the set positions for the stopper ring 151, that is, the positions where the retaining pin 156 and the two retaining holes 152 and 153 are in engagement. If the stopper ring 151 is set in the cutting position, therefore, the ultrasonic treatment is conducted with the movable operating handle 144 rocked toward the stationary handle 143, whereby the organism tissue H held between the probe 113 and the jaw 105 can be securely cut to form the cut portion H1, as shown in FIG. 17A.

In the case where the stopper ring 151 is set in the coagulating position, the distal probe 113 and the jaw 105 are kept in a position such that they are not in contact with each other when the ultrasonic treatment is carried out with the movable operating handle 144 closed or rocked toward the stationary handle 143, so that the organism tissue H can be securely coagulated without being cut. Accordingly, there is no need of fine adjustment of the grip force for the operation in which the movable operating handle 144 is closed or rocked toward the stationary handle 143, which is required by the conventional ultrasonic coagulating/cutting apparatus, so that the operability can be improved. Further, the grip force for the operation in which the movable operating handle 144 is closed or rocked toward the stationary handle 143 can never become so great that unexpected cutting occurs.

The set positions for the stopper ring 151 of the present embodiment, that is, the positions where the retaining pin 156 and the two retaining holes 152 and 153 are in engagement, may be set individually in a position (see FIG. 14A) where the grip force for the organism tissue held between the jaw 105 and the probe 113 is relatively small and a position (see FIG. 14B) where the grip force for the organism tissue held between the jaw 105 and the probe 113 is relatively great, as in the case of the first embodiment. The same effects of the first embodiment can be obtained in this case.

Further, the projection of the stopper 131 in the ultrasonic coagulating/cutting apparatus 1 of the first embodiment may be switched between the set positions for the stopper ring 151 of the present embodiment, that is, the cutting position for cutting the organism tissue and the coagulating position where the jaw 105 is stopped at the halfway position short of the cutting position.

Figure 18:
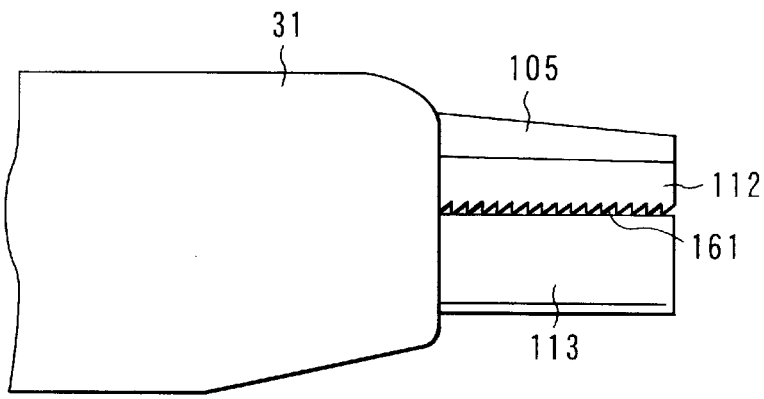
FIG. 18 is a side view showing an arrangement of the principal part of an ultrasonic coagulating/cutting apparatus of a third embodiment of the present invention.

FIG. 18 shows a third embodiment of the present invention. The present embodiment is obtained by modifying the arrangement of the jaw 105 of the ultrasonic coagulating/cutting apparatus 1 of the first embodiment (see FIGS. 1 to 14B) in the following manner.

More specifically, a contact member 112 of a jaw 105 of the present embodiment is formed having a large number of skid-proof serrated teeth 161 for the organism tissue on its surface that is opposed to a probe 113. A slope is formed on the distal end side of an angular tooth portion of each serrated tooth, and a substantially vertical surface is formed on the rear end side, so that the organism tissue held between the jaw 105 and the probe 113 cannot easily slip toward the distal end.

According to the present embodiment, therefore, the serrated teeth 161 of the jaw 105 bite into the organism tissue when the organism tissue is held between the jaw 105 and the probe 113, so that the organism tissue is prevented from easily slipping off toward the distal end of the jaw 105. Thus, the organism tissue held between the jaw 105 and the probe 113 can be securely prevented from slipping off from between the jaw 105 and the probe 113 when ultrasonic waves are outputted.

Figure 19:
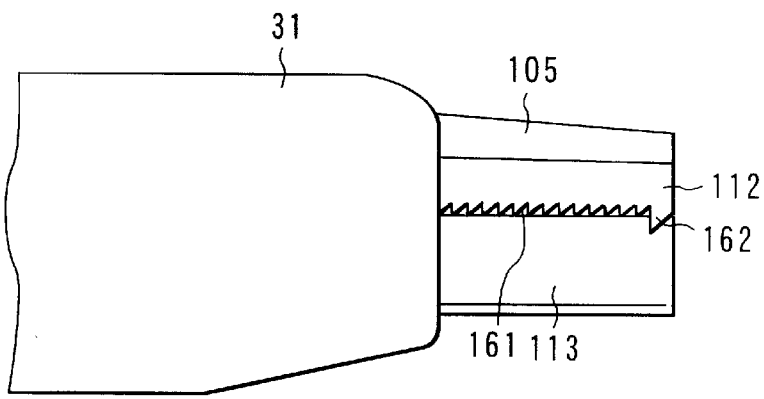
FIG. 19 is a side view showing an arrangement of the principal part of an ultrasonic coagulating/cutting apparatus of a fourth embodiment of the present invention.

FIG. 19 shows a fourth embodiment of the present invention. The present embodiment is obtained by further modifying the arrangement of the jaw 105 of the ultrasonic coagulating/cutting apparatus 1 of the third embodiment (see FIG. 18) in the following manner.

More specifically, a contact member 112 of a jaw 105 of the present embodiment has a large-sized fang-shaped claw 162 that protrudes therefrom at the extreme end portion ahead of serrated teeth 161, which are arranged on its surface opposite to a probe 113, and projects higher than the teeth 161.

According to the present embodiment, therefore, the claw 162 at the extreme end portion, along with the serrated teeth 161 of the jaw 105, bites into the organism tissue when the organism tissue is held between the jaw 105 and the probe 113, so that the organism tissue is further prevented from easily slipping off toward the distal end of the jaw 105. Thus, the organism tissue held between the jaw 105 and the probe 113 can be securely prevented from slipping off from between the jaw 105 and the probe 113 when ultrasonic waves are outputted.

Figure 20:
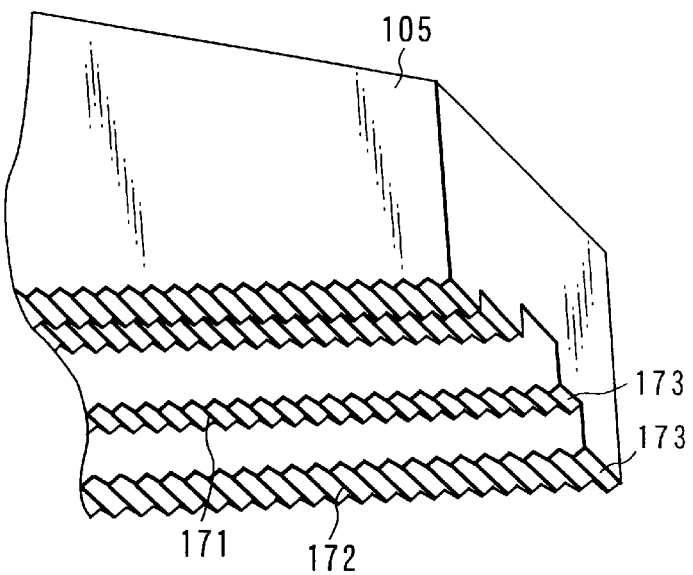
FIG. 20 is a perspective view showing an arrangement of the principal part of an ultrasonic coagulating/cutting apparatus of a fifth embodiment of the present invention.

FIG. 20 shows a fifth embodiment of the present invention. The present embodiment is obtained by modifying the arrangement of the jaw 105 of the ultrasonic coagulating/cutting apparatus 1 of the first embodiment (see FIGS. 1 to 14B) in the following manner.

More specifically, a contact member 112 of a jaw 105 of the present embodiment is provided with grip portions 171 and 172, a double recess or two steps formed in the surface opposite to a probe 113, each of the grip portions 171 and 172 having serrated teeth 173 thereon. The grip portions 171 and 172 are provided on other parts than the region in direct contact with the probe 113.

According to the present embodiment, therefore, the organism tissue can be securely grasped by means of the doubly recessed grip portions 171 and 172 of the jaw 105 when the organism tissue is held between the jaw 105 and the probe 113. Accordingly, slippage of the organism tissue can be prevented more securely than in the conventional case where the organism tissue is grasped by means of one surface, so that the organism tissue can be securely coagulated and cut.

Figure 21:
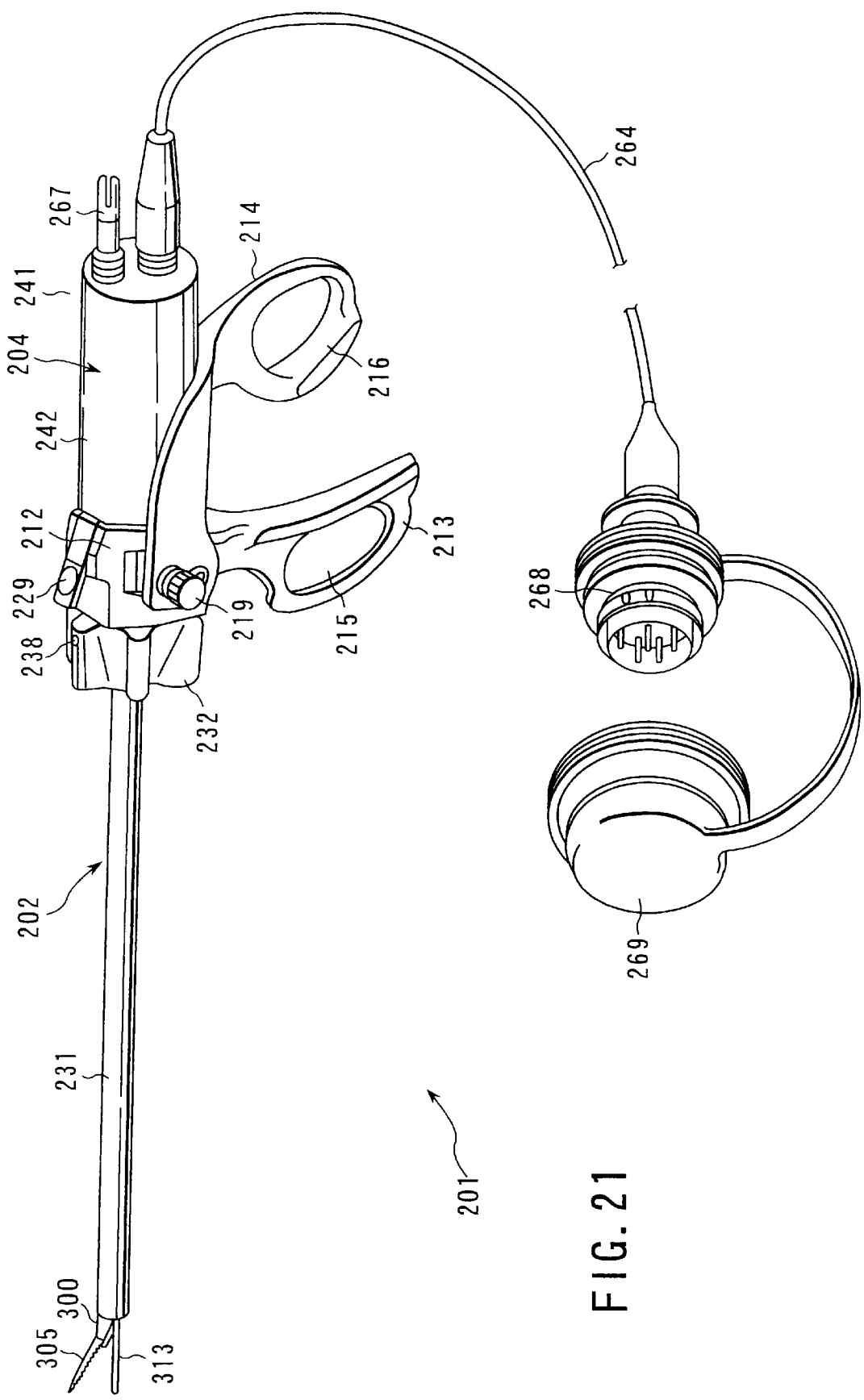
FIG. 21 is a perspective view showing an assembled state of an ultrasonic coagulating/cutting apparatus according to a sixth embodiment of the present invention.

FIGS. 21 to 33B show a sixth embodiment of the present invention. FIG. 21 is a perspective view showing an outline of an ultrasonic coagulating/cutting apparatus 201 of the present embodiment. The ultrasonic coagulating/cutting apparatus 201 comprises a handle unit 202 shown in FIG. 22A, a probe unit 203 shown in FIG. 22B, and a vibrator unit 204 shown in FIG. 23. These units 202, 203 and 204 of the ultrasonic coagulating/cutting apparatus 201 are assembled in the state shown in FIG. 21.

As shown in FIG. 22A, the handle unit 202 is provided with a front handle 213, fixed to an operating section body 212 having a vibrator connecting portion 211, and a rockable rear handle 214. An operating end portion of the front handle 213 is provided with a finger hole 215 into which a plurality of fingers other than the thumb can be inserted selectively, while an operating end portion of the rear handle 214 is provided with a finger hole 216 to which the thumb of the same hand is to be anchored.

Further, bifurcated connecting arm portions 214a and 214b are provided on the distal end side of the rear handle 214. As shown in FIG. 25, these connecting arm portions 214a and 214b are arranged on either side of the operating section body 212. The connecting arm portions 214a and 124b of the rear handle 214 are pivotally mounted for rotation on a pivot 217 that is screwed to the operating section body 212.

As shown in FIG. 22A, the connecting arm portions 214a and 214b of the rear handle 214 are formed individually having through holes 223 for fixing screw members 219 that double as retaining pins. The fixing screw members 219 penetrate the through holes 223, individually.

As shown in FIG. 25, the inner end of each fixing screw member 219 is provided with an engaging portion 221 that is caused to engage the probe unit 203. Further, an operating knob portion 222 is formed on the outer end of the fixing screw member 219. Furthermore, a shaft-shaped loose fitting portion 224 is formed on the intermediate portion of the fixing screw member 219. The loose fitting portion 224 is adjusted so that its axial length is greater than the length of each through hole 223. The respective loose fitting portions 224 of the fixing screw members 219 are loosely passed through the through holes 223 of the connecting arm portions 214a and 214b, individually. Thus, each engaging portion 221 can be evacuated from a position where it engages a rotor 278 (mentioned later) of the probe unit 203.

Further, the outer end portion of the loose fitting portion 224 of each fixing screw member 219 is formed with an external thread portion 226 that has a diameter larger than that of the loose fitting portion 224. Furthermore, the outer end portion of each through hole 223 is formed with an internal thread portion 225 that mates with the external thread portion 226 of the of the fixing screw member 219. As in the case of the left-hand fixing screw member 219 of FIG. 25, the engaging portion 221 can be move to and fixed in the position of engagement with the rotor 278 by advancing the fixing screw member 219 inward along the through hole 223 so that the external thread portion 226 is screwed into the internal thread portion 225.

Further, each fixing screw member 219 is wound with a spring member, e.g., a coil spring 228, which is situated between the operating knob portion 222 and the rear handle 214. If the external thread portion 226 is disengaged from the internal thread portion 225, as shown in FIG. 26B, the fixing screw member 219 is automatically evacuated by the agency of the elastic restoring force of the coil spring 228, as shown in FIG. 25. Thus, insertion/attachment and disassembly/removal operations for the probe unit 203 cannot be hindered.

Figures 24A, 24B:
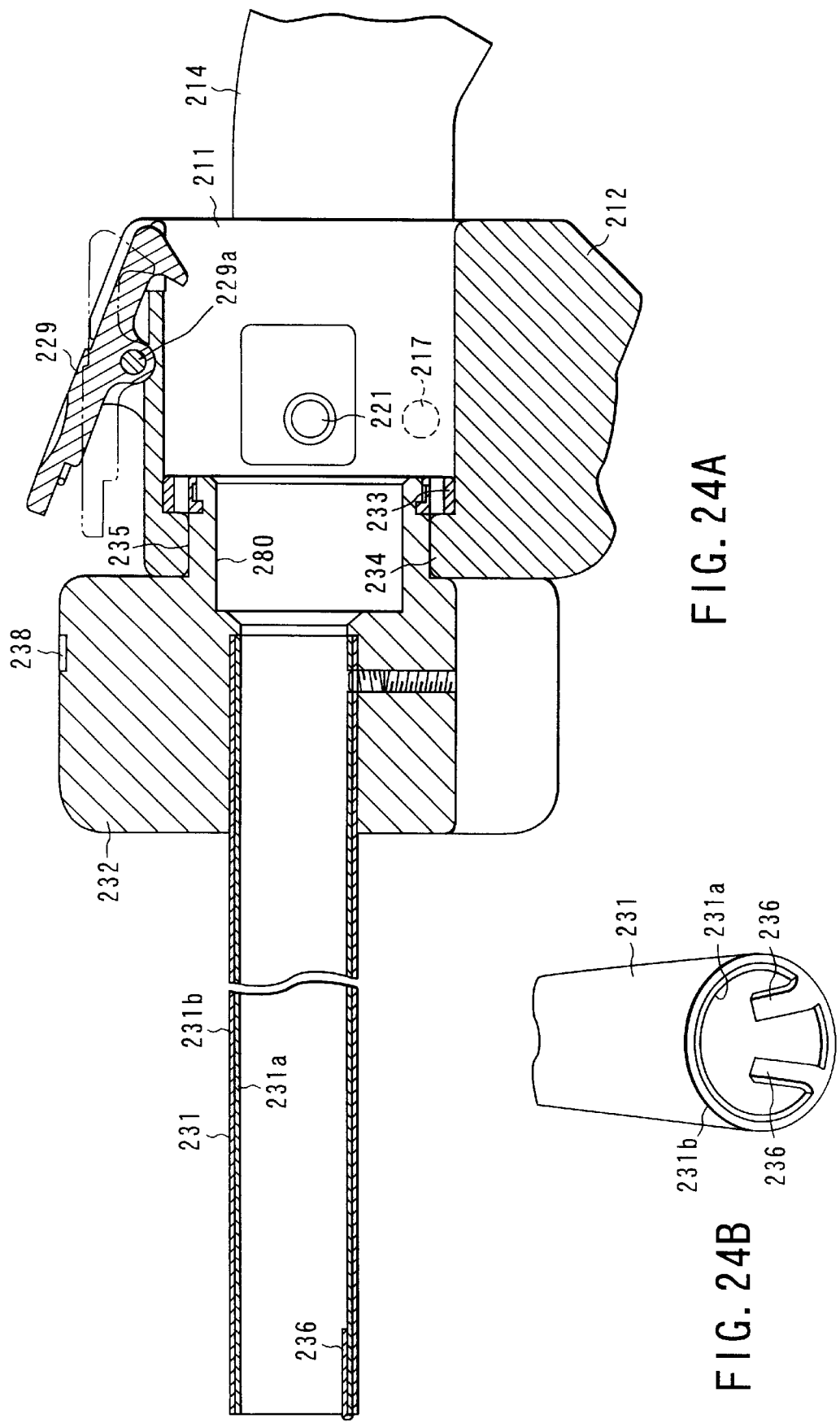
FIG. 24A is a profile of the handle unit of the ultrasonic coagulating/cutting apparatus of the sixth embodiment.
FIG. 24B is a perspective view showing retaining pieces at the distal end portion of an insertable sheath section.

Further, a stopper piece 229 for fixing the probe unit 203 to be attached to the operating section body 212 in its attachment position is pivotally mounted on the top portion of the body 212 by means of a shaft 229a, as shown in FIG. 24A. The stopper piece 229 may be formed of a metal for improved durability or an electrical insulating material to secure electrical insulating properties. The stopper piece 229 is urged by means of a spring 230 to rock in a direction such that it engages the probe unit 203, as shown in FIG. 25, and normally, is rocked in the direction indicated by full line in FIG. 24A to be on standby.

As shown in FIG. 24A, an insertable sheath section 231 is coupled to the front end of the operating section body 212 by means of a rotary knob 232 and a fixing nut 233. The insertable sheath section 231 and the rotary knob 232 are coaxially mounted on the operating section body 212 for rotation. More specifically, the rotary knob 232 is rotatably supported by means of bearing means 235, which is constructed in a manner such that a collar 234 formed on the operating section body 212 is held between the rotary knob 232 and the fixing nut 233. The insertable sheath section 231 is continually braked in some measure by means of the frictional force of its sliding-contact portion, and cannot rotate easily. If the front handle 213 and the rear handle 214 are gripped tight, however, frictional force between them increases, so that the section 231 is braked. Thus, braking means is incorporated to prevent the rotation of the insertable sheath section 231 securely.

As shown in FIG. 24A, the insertable sheath section 231 has a dual-pipe structure including a core 231a, formed of a stiff metallic pipe, and a skin 231b of an electrical insulating resin covering the core. As shown in FIG. 24B, a distal end portion in the insertable sheath section 231 is provided with a pair of retaining pieces 236 capable of engaging the probe unit 203 that is passed through the same. The retaining pieces 236 are formed by partially extending the core 231a and bending it inward. Corresponding to this retaining position, an index 238 indicative of the retaining position is provided on the top surface portion of the rotary knob 232.

If the probe unit 203 is inserted into the operating section body 212 with the index 238 upward, a part of a jaw retaining member (mentioned later) on the distal end of the probe unit 203 engages the retaining pieces 236, and at the same time, the stopper piece 229 fixes that portion of the vibrator unit 204 which corresponds to a hand piece 241 in its attachment position.

The vibrator unit 204 is constructed in the manner shown in FIG. 27A. More specifically, an ultrasonic vibrator 243 is located in a cylindrical cover 242 of the hand piece 241. A horn 244 is coupled to the front end of the ultrasonic vibrator 243.

As shown in FIG. 27B, moreover, the distal end of the horn 244 is formed having an internal thread portion 245 into which the rear end of the probe unit 203 is screwed. The ultrasonic vibrator 243 is held in the cover 242 with its horn 244 supported on the front end portion of the cover 242. An outer collar 246 for fixation is formed on the horn 244.

Further, an inner collar 247 protrudes from the inner peripheral surface of the distal end portion of the cover 242. Furthermore, a tapped hole portion 242a is formed in the inner peripheral surface of the distal end portion of the cover 242, on the distal end side of the inner collar 247. After the outer collar 246 of the horn 244 is fitted tight in the inner peripheral surface of the cover 242, a fixing ring 248 of the ultrasonic vibrator 243 can be screwed into the tapped hole portion 242a of the cover 242. Thus, the ultrasonic vibrator 243 is held in the cover 242 with the outer collar 246 of its horn 244 sandwiched and fixed between the inner collar 247 of the cover 247 and the fixing ring 248.

As shown in FIG. 27B, an engaging socket portion 251, a notched recess, is formed in a part of the outer collar 246 of the horn 244. The inner collar 247 of the cover 242 is formed with an engaging portion 252, a projection, which is fitted in the engaging socket portion 251 for engagement.

Further, cushion members 253 of an elastic material are axially interposed between the outer collar 246 of the horn 244, the inner collar 247 of the cover 242, and the fixing ring 248. The outer collar 246 of the horn 244 is held and clamped by means of the cushion members 253.

As shown in FIG. 27A, furthermore, a ring-shaped stopper receiving member 256 fixedly attached to the front end portion of the cover 242 by screwing. An annular circumferential groove 257 is formed on the outer peripheral surface portion of the stopper receiving member 256. The stopper piece 229 on the side of the handle unit 202 can be fitted in and retained by the stopper receiving member 256. The rear end portion of a rotor 278 of the probe unit 203 can be fitted in a bore 258 of the stopper receiving member 256.

The ultrasonic vibrator 243 is composed of a Langevin ultrasonic vibrator shown in FIG. 27B. The Langevin ultrasonic vibrator includes a plurality of piezoelectric devices 261 that are stacked in layers. A laminate of these piezoelectric devices 261 is located between the horn 244 and a backside member 262, and is tightened by means of a bolt (not shown) that penetrates its central portion. Further, electrodes 263 are interposed between the piezoelectric devices 261, individually. A driving voltage is applied to the piezoelectric devices 261 through the electrodes 263.

A lead wire 265 from a hand piece cord 264 is connected to the electrodes 263. Another lead wire 266 is further connected to the ground-side electrodes 263. The lead wire 266 is connected to a high-frequency connecting pin 267. The connecting pin 267 can be connected with a high-frequency supply cord (not shown) that connects with a high-frequency power source. The ground-side electrodes 263 electrically connect with electrically conductive bolts of the ultrasonic vibrator 243 and the horn 244 that is also electrically conductive.

A vibration transmitting member and a probe (mentioned later) of the probe unit 203 that are connected to the distal end of the horn 244 are also electrically conductive members, and these members help electrical conduction to a distal treatment portion.

Figure 23:
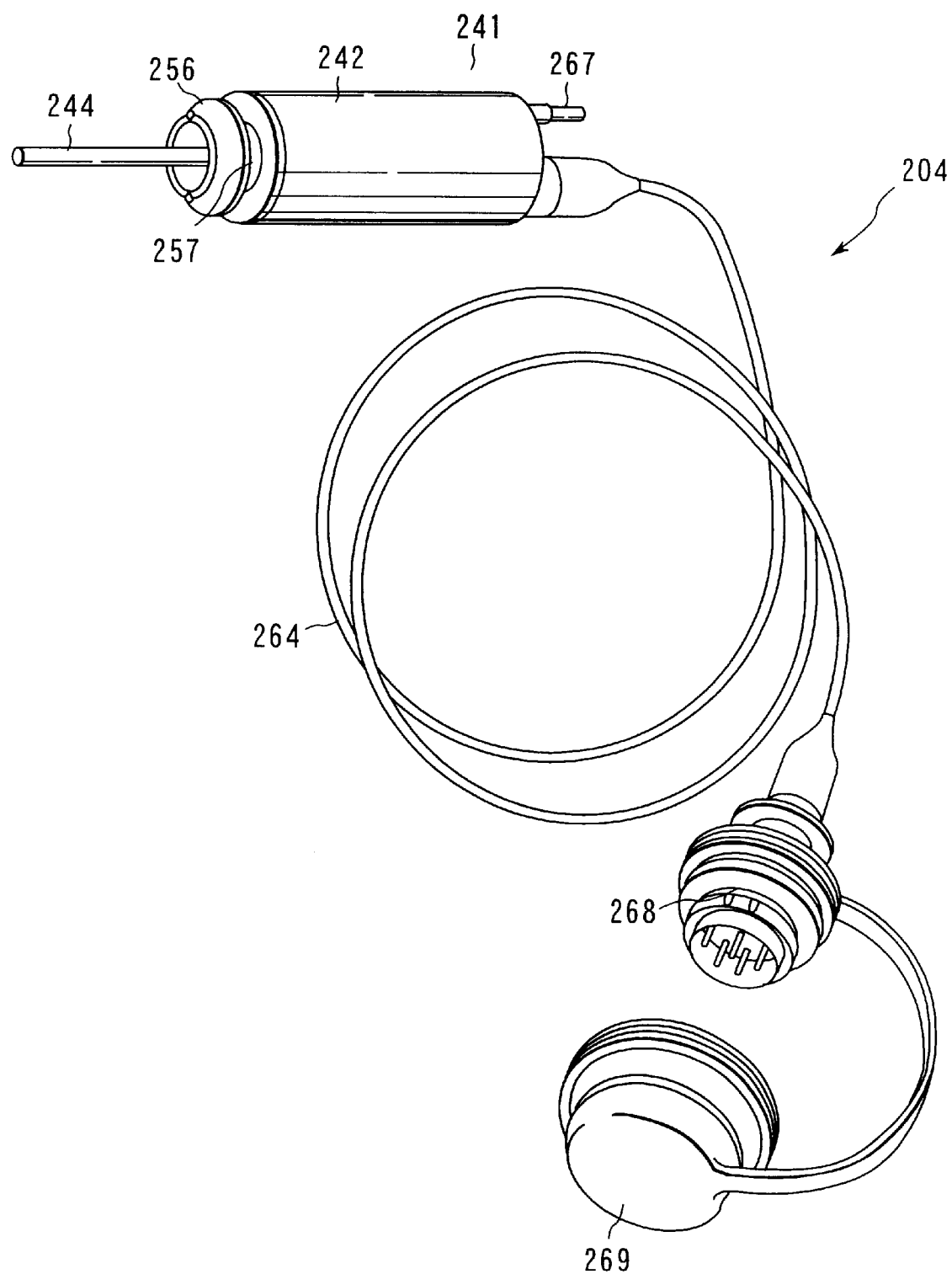
FIG. 23 is a perspective view of a vibrator unit of the ultrasonic coagulating/cutting apparatus of the sixth embodiment.

As shown in FIG. 23, the hand piece cord 264 is elongated and flexible. A hand piece plug 268 is provided on the extended distal end of the hand piece cord 264. A detachable waterproof cap 269 is attached to the hand piece plug 268. In cleaning the vibrator unit 204, a region near a terminal portion of the hand piece plug 268 is covered by means of the waterproof cap 269.

The probe unit 203 is formed in the manner shown in FIGS. 28A to 30H. More specifically, the probe unit 203 includes a vibration transmitting member 271 for transmitting ultrasonic vibration and an operation drive shaft 272 that is located substantially parallel to the same. The vibration transmitting member 271, which has a high acoustic effect, is formed of a titanium or aluminum material that is highly adaptive to living organisms.

The vibration transmitting member 271 is formed of two bodies, a distal-end-side portion 271a and a rear-end-side portion 271b, which are fixedly coupled to each other by screwing and adhesive bonding. As shown in FIG. 29B, an external thread portion 273 is formed on the rear end portion of the vibration transmitting member 271. The external thread portion 273 can be screwed into an internal thread portion 245 that is formed on the distal end of the horn 244. The external thread portion 273 can be firmly coupled by being screwed into a position such that a stepped end face 274 at the rear end of the vibration transmitting member 271 abuts against the distal end face of the horn 244.

Spanner catch faces 275 are formed on the peripheral surface of the rear end portion of the vibration transmitting member 271. An opening portion of a spanner (mentioned later) can be engagedly anchored to the spanner catch faces 275.

Figure 30A:
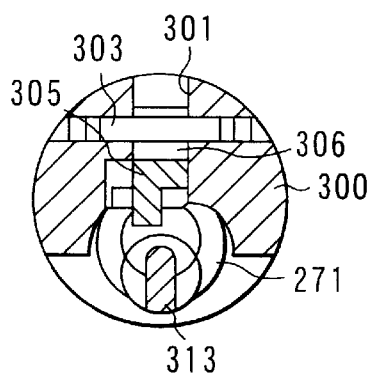
FIG. 30A is a sectional view taken along line 30A—30A of FIG. 28A.
Figure 30B:
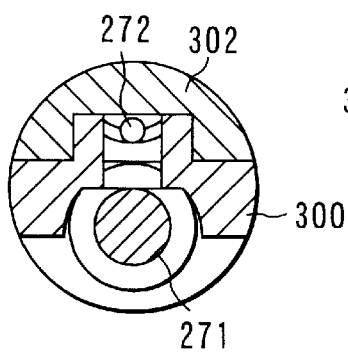
FIG. 30B is a sectional view taken along line 30B—30B of FIG. 28A.
Figure 30C:
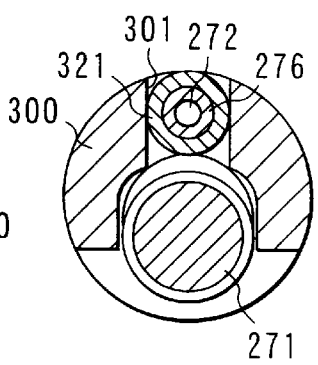
FIG. 30C is a sectional view taken along line 30C—30C of FIG. 28A.
Figure 30D:
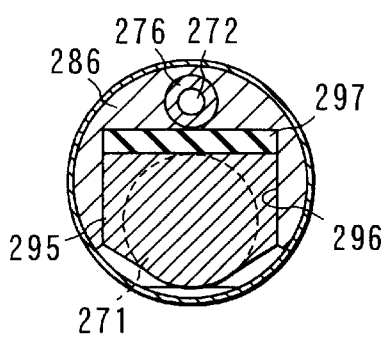
FIG. 30D is a sectional view taken along line 30D—30D of FIG. 28A.

The operation drive shaft 272 is a wire-shaped member formed of stainless steel (SUS) or some other material that is relatively stiff and has spring elasticity. Further, a thin-walled metallic pipe 276 is fitted on the operation drive shaft 272. The pipe 276 is fitted ranging from the proximal end of the operation drive shaft 272 to a middle portion short of the distal end. The pipe 276 is bonded to the peripheral surface of the operation drive shaft 272. As shown in FIGS. 28B and 30F, a small notch 277 is formed in a suitable portion of the pipe 276. The pipe 276 and the shaft 272 are bonded with an adhesive agent that is introduced through the opening of the notch 277.

As shown in FIG. 29B, the rotor 278 is fixedly attached to the rear end of the operation drive shaft 272. The rotor 278 is formed in the shape of a cylindrical rotating body having a central axis in alignment with the central axis of the vibration transmitting member 271.

Two collars 281 are provided on the outer periphery of the rotor 278, and an annular groove 282 for engagement is formed between these two collars 281. The engaging portion 221 of the fixing screw member 219, which is attached to the rear handle 214, a movable handle of the handle unit 202, is fitted in the annular groove 282 for engagement.

O-rings 283 and 284 are fitted individually on front and rear peripheral surface portions of the annular groove 282 for engagement. When the units 202, 203 and 204 are assembled, a front-end-side peripheral portion 285 of the rotor 278 is fitted into a fitting hole portion 280 of the handle unit 202, and a rear-end-side peripheral portion 287 of the rotor 278 is fitted into the bore 258 of the stopper receiving member 256 in the bore of the operating section body 212.

Further, the stopper piece 229 can engage the circumferential groove 257 of the stopper receiving member 256 on the side of the vibrator unit 204. Thereupon, the vibrator unit 204 is allowed to rotate integrally with the probe unit 203. Further, by handle operation by means of the handle unit 202, the operation drive shaft 272 of the probe unit 203 can be moved integrally with the rotor 278 in the longitudinal direction with respect to the vibrator unit 204 and the vibration transmitting member 2071, stationary members.

As shown in FIG. 29A, the vibration transmitting member 271 and the operation drive shaft 272 are coupled to each other by means of a plurality of spacers 286. Each attached spacer 286 is situated corresponding to a node of vibration of the vibration transmitting member 271.

The spacer 286 is provided with a fitting groove 287 in which an intermediate portion of the vibration transmitting member 271 is slidably fitted and a support hole 288 that penetrates the operation drive shaft 272 having the pipe 276 thereon. These spacers 286 serve to keep the vibration transmitting member 271 and the operation drive shaft 272 parallel to each other with a given space between them.

Further, the pipe 276 that is fitted on the operation drive shaft 272 is provided with retaining rings 289 that are put on the pipe 276 so as to be situated individually before and behind their corresponding spacers 286, among all other spacers 286 except the foremost one, in order to prevent the spacers 286 from moving back and forth. Each retaining ring 289 is fixed to the outer periphery of the pipe 276 by adhesive bonding. The retaining ring 289 is formed having a slit 290 into which the adhesive agent is to be poured.

The foremost spacer 286 is located in the position of a node of ultrasonic vibration that is nearest to the far end of a probe 313, which will be mentioned later. The foremost spacer 286 is put on the outer periphery of the pipe 276 on the operation drive shaft 272 so as to be movable in the axial direction of the pipe. The foremost spacer 286 may be fixed by being bonded to the outer periphery of the pipe 276.

Figure 30E:
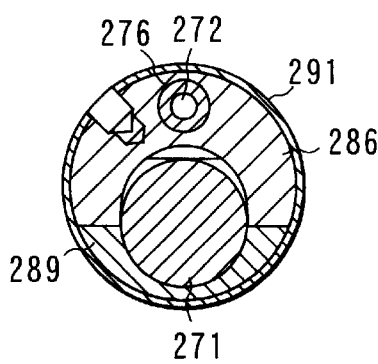
FIG. 30E is a sectional view taken along line 30E—30E of FIG. 28A.
Figure 30F:
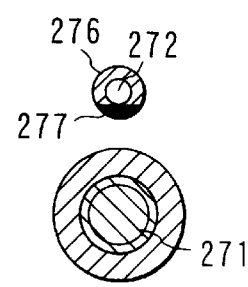
FIG. 30F is a sectional view taken along line 30F—30F of FIG. 28B.
Figure 30G:
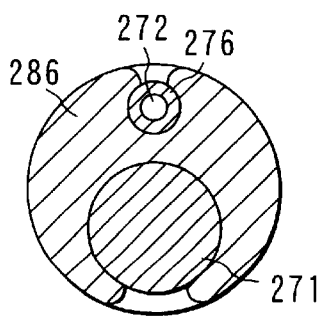
FIG. 30G is a sectional view taken along line 30G—30G of FIG. 29A.
Figure 30H:
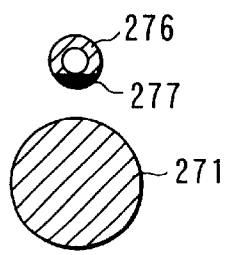
FIG. 30H is a sectional view taken along line 30H—30H of FIG. 29A.

As shown in FIG. 30E, moreover, the spacer 286 is provided with a support member 289. A retaining ring 291 is fitted on the spacer 286 and the support member 289 to couple the two, and is integrally fixed by adhesive bonding. More specifically, that portion of the vibration transmitting member 271 which corresponds to a flange 295 (mentioned later) is held between the spacer 286 and the support member 289 from above and below. In this state, the retaining ring 291 is fitted on and fastened to the spacer 286 and the support member 289, and the spacer 286 and the retaining ring 291 are bonded together. The support member 289 is a member that is included in the spacer 286, and these two members may alternatively be fixed by adhesive bonding.

As shown in FIG. 30D, the vibration transmitting member 271 is formed having the rotation restraining flange 295 in a position corresponding to the foremost spacer 286. The profile of the rotation restraining flange 295 is a substantially rectangular irregular shape. The inner surface portion of the foremost spacer 286 is formed with an inlaying groove 296 that has the same shape as the rotation restraining flange 295. The rotation restraining flange 295 is engagedly fitted into the inlaying groove 296 of the foremost spacer 286, whereby the spacer 286 can be restrained from rocking around the axis of the vibration transmitting member 271.

Further, a cushion member 297 of a vibration absorbing material, e.g., rubber, is fitted in the inlaying groove 296 of the spacer 286 on the side of the operation drive shaft 272. The cushion member 297 is located between the rotation restraining flange 295 and the spacer 286.

The foremost spacer 286 doubles as a support portion for a jaw retaining member 300 that extends forward from its position. The spacer 286 and the jaw retaining member 300 are formed integrally with each other. Thus, the jaw retaining member 300 is restrained from moving in the axial direction of the vibration transmitting member 271 and from rocking around the axis of the member 271.

Further, the so-called stationary blade 313 having an elongated profile is formed on the distal end portion of the vibration transmitting member 271 by directly using the vibration transmitting member 271. The peripheral surface portion of the distal end of this probe 313 is rounded.

Figure 31:
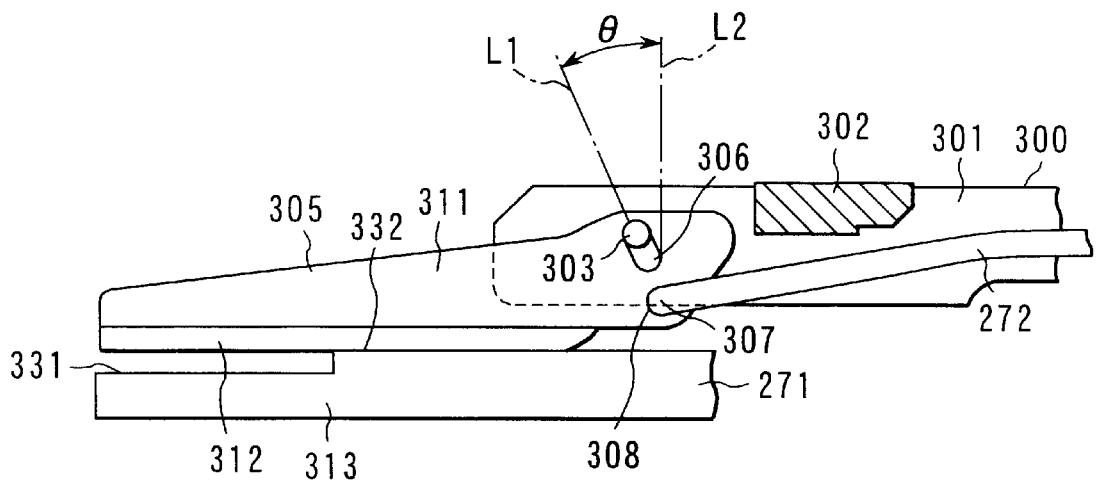
FIG. 31 is a view illustrating a distal treatment portion of the probe unit of the sixth embodiment.

As shown in FIG. 31, moreover, the front end of the jaw retaining member 300 extends to a position short of the distal end of the vibration transmitting member 271. A jaw 305 (mentioned later) can be coupled to the distal end portion of the jaw retaining member 300.

Further, the jaw retaining member 300 is formed having a slit 301 that extends from its proximal end portion to the distal end, as shown in FIG. 30C. A reinforcing bridge 302 for coupling the left- and right-hand portions of the slit 301 is provided at the distal end portion of the jaw retaining member 300 (see FIG. 30B).

At the distal end portion of the jaw retaining member 300, a pivot 303 is located bridging the left- and right-hand side portions of the slit 301 on the distal end side of the reinforcing bridge 302. The jaw 305, which constitutes a so-called movable blade that faces the stationary probe 313, is pivotally mounted on the pivot 303. As shown in FIG. 31, the jaw 305 is composed of a base 311 and a contact member 312, which are integrally with each other. The base 311 is formed of a metallic material, while the contact member 312 is formed of, for example, Teflon (trademark of tetrafluoroethylene resin produced by E. I. Du Pont de Nemours & Co.).

Figure 28A:
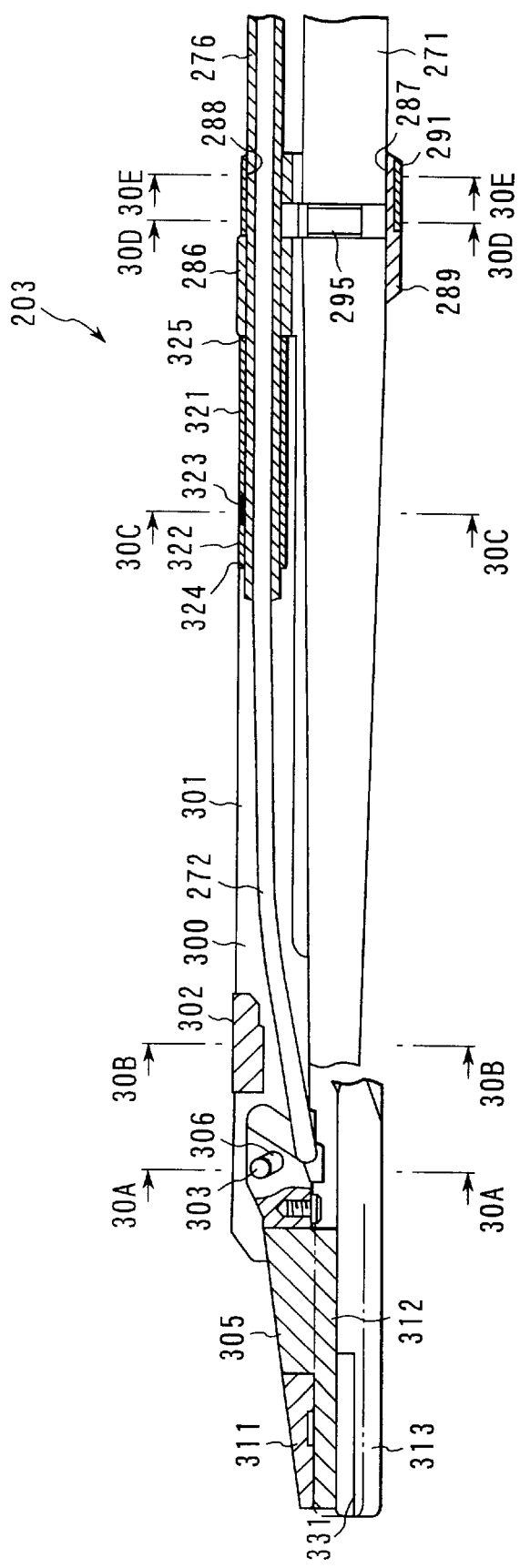
FIG. 28A is a profile of a distal-end-side portion of the probe unit of the sixth embodiment.
Figure 28B:
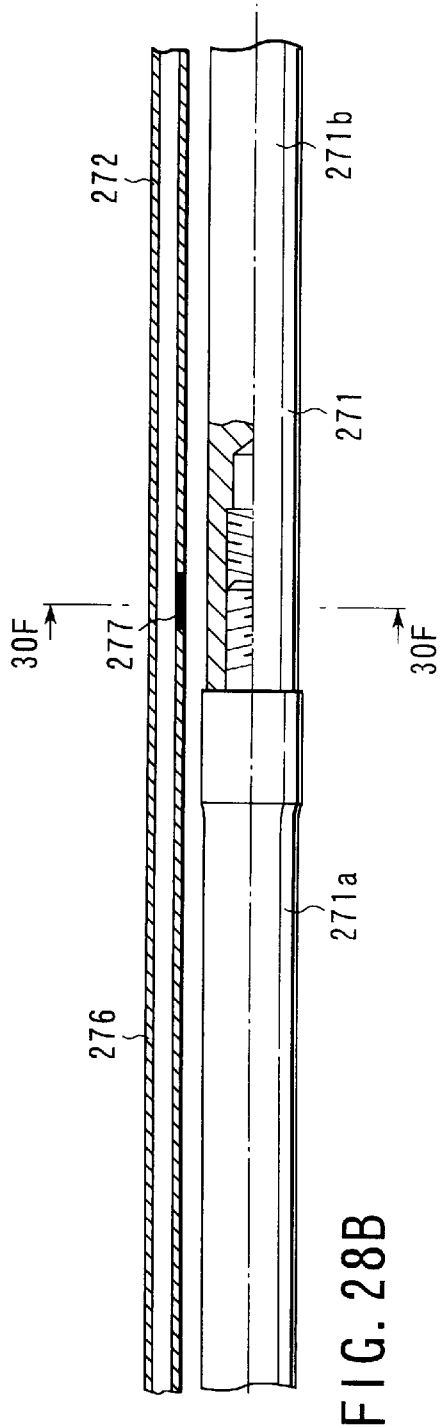
FIG. 28B is a profile of an intermediate portion of the probe unit of the sixth embodiment.

At the distal end portion of the jaw retaining member 300, moreover, a bearing connecting hole 306 of the jaw 305, which is formed of an oblique slot, as shown in FIG. 28A, is formed in each of left- and right-hand side portions of the slit 301. The pivot 303 is fitted in the connecting hole 306.

As shown in FIG. 31, furthermore, the distal end of the operation drive shaft 272 is coupled to that part of the proximal end portion of the jaw 305 which is situated under the connecting hole 306. The distal end portion of the operation drive shaft 272 is bent substantially at right angles, and its bent portion 307 is fitted into and rockably coupled to a hole 308 in the jaw 305 from the side face of the jaw 305.

The length (width) of the bent portion 307 is a little shorter than the with of the slit 301 shown in FIG. 30A, and the bent portion 307 is provided so that it is always situated in the slit 301. If the bent portion 307 is broken at the base, therefore, it can be held in the hole 308 of the jaw 305, and its fragments never drop into the body cavity or the like.

The jaw 305 can be rocked opposite the probe 313 by pushing or pulling the operation drive shaft 272. Thus, the jaw 305 and the probe 313 constitute a closable ultrasonic treatment unit that can grasp an organism tissue. FIG. 28A shows a state in which the jaw 305 is closed by pulling the operation drive shaft 272. In this state, the contact member 312 of the jaw 305 is entirely in contact with the top surface of the probe 313.

Figures 32A, 32B:
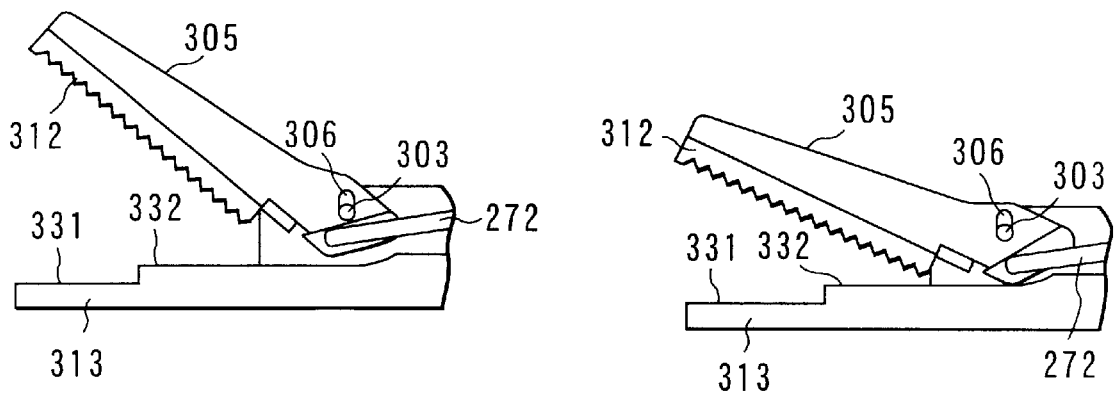
FIG. 32A is a profile of a principal part showing the distal treatment portion of the probe unit of the sixth embodiment open in its maximum opening position.
FIG. 32B is a profile of the principal part showing the distal treatment portion of the probe unit of the sixth embodiment open in its medium opening position.
Figure 32C:
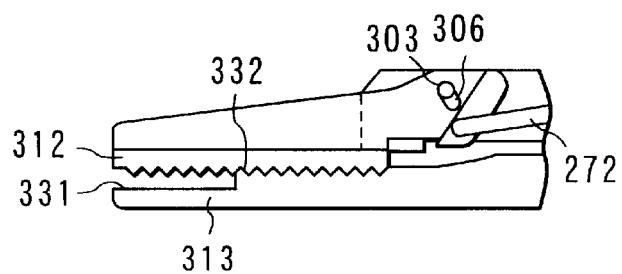
FIG. 32C is a profile of the principal part showing the distal treatment portion of the probe unit of the sixth embodiment closed.

The connecting hole 306 of the jaw 305 is in the form of a slot. The width of the connecting hole 306 is adjusted to a size such that pivot 303 fitted in the connecting hole 306 is movable. As shown in FIG. 31, moreover, the longitudinal direction (L1) of the connecting hole 306 is inclined at an angle θ to a line L2 that is normal to the grip face of the probe 313. If the longitudinal direction L1 of the connecting hole 306 is oblique in this manner, the engagement of the jaw 305 with the probe 313 is improved. Thus, the pivot 303 is relatively movable in the connecting hole 306 of the jaw 305, as shown in FIGS. 32A to 32C, so that the process of operation during which the jaw 105 uniformly engages the probe 313 to grasp the organism tissue lengthens, and closing impact for seizure becomes generally uniform.

In the case of this embodiment, the angle θ of inclination of the connecting hole 306 is adjusted to a value greater than 0° and smaller than 90°. Preferably, the angle θ should be at 45° or less. If the angle θ is adjusted to 12°±10°, in particular, the grip force is substantially uniform on the distal end side of the jaw 305 and on the hand side.

The relation between the pivot 303 and the connecting hole 306 for supporting the jaw 305 may be changed so that the pivot 303 and the connecting hole 306 are provided or formed on the sides of the jaw 305 and the jaw retaining member 300, respectively. The same effects as aforesaid can be obtained also in this case.

Further, a stopper pipe 321 is fitted on the middle portion of the operation drive shaft 272 that is inserted in the slit 301 of the jaw retaining member 300. An internal thread is formed on the inner peripheral surface of the stopper pipe 321, and is attached in threaded engagement with an external thread formed on the outer periphery of the pipe 276 that is put on the operation drive shaft 272. With use of the attachment means based on this threaded engagement, the position of the stopper pipe 321 can be finely adjusted in the process of manufacture.

Further, a tubular nut 322 is screwed on the external thread portion on the outer periphery of the pipe 276, whereby the stopper pipe 321 is fixed in a double-nut fashion. Formed on the respective outer peripheral surfaces of the stopper pipe 321 and the nut 322 are knurls as skid-proof means for rotating operation. Furthermore, the stopper pipe 321 and the nut 322 are bonded to the pipe 276 on which they are screwed. The stopper pipe 321 and the nut 322 are formed having a slit 324 into which an adhesive agent is to be poured.

When the operation drive shaft 272 is pulled in to close the jaw 305, the rear end of the stopper pipe 321 abuts against a stopper receiving member 325 that is formed of the rear end face of the slit 301 on the stationary member side, thereby preventing further pulling to restrict the manipulated variable of the jaw 305. Thus, the jaw retaining member 300 is formed having a stopper mechanism for regulating the manipulated variable of the jaw 305 as the jaw 305 is closed by pulling the operation drive shaft 272.

Since the stopper pipe 321 is attached to the operation drive shaft 272 by screwing, the position of the stopper pipe 321 relative to the operation drive shaft 272 can be adjusted for accurate attachment so that component errors can be eliminated as those elements are joined together.

As shown in FIG. 31, moreover, the probe 313 of the distal treatment portion of the probe unit 203 in the ultrasonic coagulating/cutting apparatus 201 of the present embodiment is provided with a recess (non-contact portion) 331 cut in its surface opposite to the jaw 305 and a contact portion 332 to be in contact with the jaw 305. The recess 331 is located at the extreme end portion of the probe 313, while the contact portion 332 is located behind the recess 331. The recess 331 of the probe 313 is formed by cutting during the manufacture of the probe 313.

Further, the recess 331 of the probe 313 is kept untouched by the jaw 305 when the jaw 305 is closed or rocked toward the probe 313, and functions as a portion for coagulating a to-be-treated region of the organism tissue held between the probe 313 and the jaw 305. The contact portion 332 of the probe 313 moves to a position where it touches the jaw 305 when the jaw 305 is rocked toward the probe 313, and functions as a portion for excising (or incising) the organism tissue held between the probe 313 and the jaw 305.

The following is a description of the operation of the arrangement described above. In operating the ultrasonic coagulating/cutting apparatus 201 of the present embodiment, the jaw 305 of the distal treatment portion can be opened or closed by grasping the handles 213 and 214 of the handle unit 202 with one hand and rocking the rear handle 214. When the rear handle 214 is rocked, the jaw 305 rocks with respect to the fixedly located probe 313 so that the organism tissue is held between them or opens so that an internal organ can be separated or excluded between them.

In conducting ultrasonic treatment, moreover, the apparatus is guided into the abdomen by utilizing a trocar or the like, and the organism tissue of an affected part is held between the probe 313 and the jaw 305 of the distal treatment portion. As this is done, the grip force to grasp the organism tissue is relatively small at the recess 331 at the extreme end portion of the probe 313, while the grip force for the organism tissue is great at the contact portion 332 behind the recess 331.

In this state, ultrasonic vibration is applied to the probe 313. As this is done, the organism tissue held between the probe 313 and the jaw 305 is coagulated at the recess 331 of the probe 313. At the contact portion 332 of the probe 313, moreover, the organism tissue held between the probe 313 and the jaw 305 coagulates as it is excised (or incised).

Accordingly, the above-described arrangement provides the following effects. More specifically, in the ultrasonic coagulating/cutting apparatus 201 of the present embodiment, that surface of the probe 313 which faces the jaw 305 is provided with the notched recess 331 and the contact portion 332 that is in contact with the jaw 305. Thus, when the jaw 305 is closed or rocked toward the probe 313, the organism tissue can be coagulated at the non-contact portion between the jaw 305 and the recess 331, and the organism tissue held between the probe 313 and the jaw 305 can be coagulated as it is excised (or incised) at the contact portion 332. Thus, the ultrasonic coagulating/cutting apparatus 201 can efficiently coagulate and excise an organism tissue at the same time.

In the case where an tubular tissue in the body, such as a blood vessel, the large intestine, the small intestine, or a bile duct, is cut, moreover, vascular or intestinal inosculation, a treatment for inosculating cut end portions of the tubular tissue, is carried out after the tubular tissue is cut. In general, in conducting this treatment, anastomotic openings of the blood vessel are extroverted, and the anastomotic openings are manually sutured throughout the circumference with a needle and thread in a manner such that the respective internal membranes of the pieces to be joined are in contact with each other. In carrying out the internal treatment for, for example, vascular inosculation by using the ultrasonic coagulating/cutting apparatus 201 of the present embodiment, instead of the manual suture with the needle and thread, a blood vessel H1 is cut, a peripheral edge region H3 of each anastomotic opening H2 of the blood vessel H1 is then extroverted substantially in the form of a flange, and the respective peripheral edge regions H3 of two anastomotic openings H2 of the cut blood vessel H1 are joined throughout the circumference so that the respective internal membranes of the anastomotic openings H2 are in conjunction with each other, as shown in FIG. 33A. Thereupon, a ring-shaped junction H4 is formed joining the respective peripheral edge regions H3 of the two anastomotic openings H2 of the cut blood vessel H1.

Subsequently, the ring-shaped junction H4 of the cut blood vessel H1 are partially held between the probe 313 and the jaw 305 of the ultrasonic coagulating/cutting apparatus 201 of the present embodiment. In this state, ultrasonic vibration is applied to the probe 313. As this is done, the junction H4 of the blood vessel H1 is coagulated at the recess 331 of the probe 313, and trimming is carried out such that the junction H4 of the blood vessel H1 is coagulated as it is excised (or incised) at the contact portion 332. Thus, the coagulation of the junction H4 of the blood vessel H1 and the trimming process for excising unnecessary portions around the junction H4 can be carried out simultaneously.

This ultrasonic treatment is conducted in a plurality of positions along the circumference of the junction H4. When the ultrasonic treatment is finished in all the positions, the inosculation of the junction H4 of the blood vessel H1 terminates, as shown in FIG. 33B.

Figure 47:
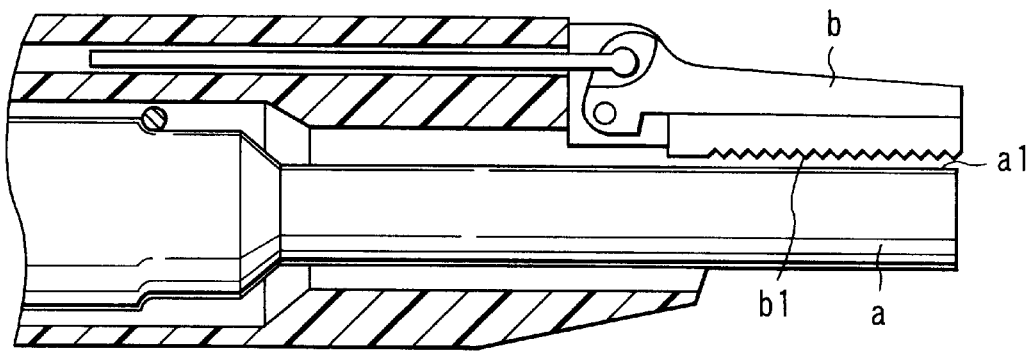
FIG. 47 is a profile of a distal treatment portion of an ultrasonic coagulating/cutting apparatus showing a prior art example.
Figure 48:
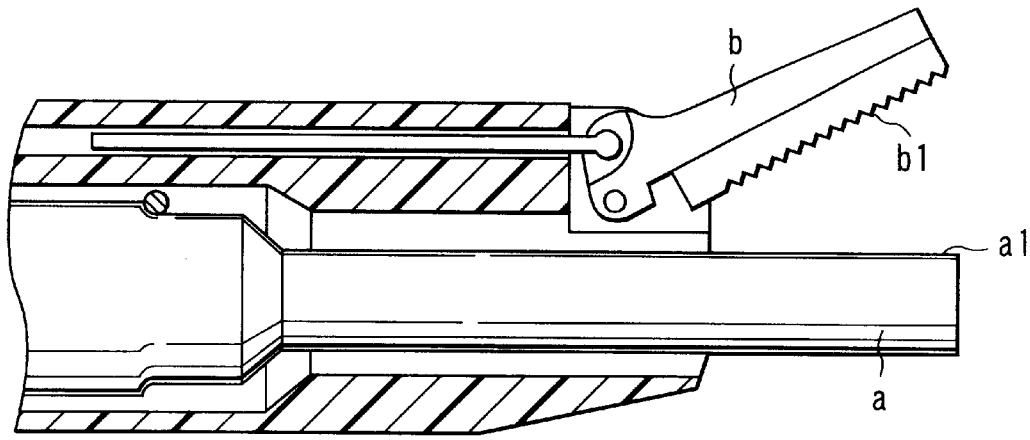
FIG. 48 is a profile showing an open state of a jaw of the ultrasonic coagulating/cutting apparatus of FIG. 47.
Figure 49:
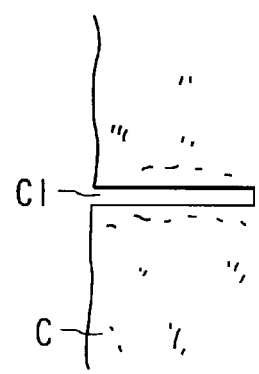
FIG. 49 is a plan view showing a cut portion of an organism tissue cut by means of the ultrasonic coagulating/cutting apparatus of FIG. 47.

FIGS. 47 and 48 show a conventional ultrasonic coagulating/cutting apparatus. In the conventional ultrasonic coagulating/cutting apparatus, as shown in FIGS. 47 and 48, organism tissue grip faces a1 and b1 of a blade a and a jaw b are set substantially uniformly in a line. In an organism tissue coagulating/cutting treatment, a cut portion c1 having substantially the same shape as the organism tissue grip faces a1 and b1 of the blade a and the jaw b is formed in an organism tissue c, as shown in FIG. 49.

In conducting ultrasonic treatment by using the conventional ultrasonic coagulating/cutting apparatus, therefore, trimming is carried out in a manner such that the unnecessary portions around the junction are excised after a plurality of portions along the circumferences of the peripheral edge regions of the anastomotic openings are coagulated and joined together. Thus, the coagulation and excision of the organism tissue can be carried out individually during one cycle of treatment such as vascular inosculation.

In the ultrasonic coagulating/cutting apparatus of the conventional arrangement described above, however, the blade and the jaw are set for either coagulation or excision as they are used, so that it is hard to coagulate and excise the organism tissue efficiently at the same time with use of only one ultrasonic coagulating/cutting apparatus.

In the case where the ultrasonic coagulating/cutting apparatus 201 of the present embodiment is used to carry out the treatment for vascular inosculation, on the other hand, trimming of extra portions and inosculation can be effected simultaneously, so that the treatment for vascular inosculation can be conducted efficiently.

FIG. 34 shows a seventh embodiment of the present invention. The present embodiment is obtained by modifying the arrangement of the distal treatment portion of the probe unit 203 of the ultrasonic coagulating/cutting apparatus 201 of the sixth embodiment (see FIGS. 21 to 33B) in the following manner. For other parts, the present embodiment is constructed in the same manner as the ultrasonic coagulating/cutting apparatus 201 of the sixth embodiment.

Like numerals are used to designate like portions that are shared with the ultrasonic coagulating/cutting apparatus 201 of the sixth embodiment, and a description of those portions is omitted.

In the sixth embodiment, the probe 313 is provided with the recess 331 and the contact portion 332. According to the present embodiment, however, a notched recess (non-contact portion) 341 is formed in the distal end portion of that surface of a contact member 312 of a jaw 305 which faces a probe 313, and a contact portion 342 to be in contact with the probe 313 is formed behind the recess 341. The recess 341 of the jaw 305 is kept untouched by the probe 313 when the jaw 305 is closed or rocked toward the probe 313, and functions as a portion for coagulating a to-be-treated region of the organism tissue held between the probe 313 and the jaw 305. The contact portion 342 of the jaw 305 moves to a position where it touches the probe 313 when the jaw 305 is rocked toward the probe 313, and functions as a portion for excising (or incising) the organism tissue held between the probe 313 and the jaw 305.

When the organism tissue of an affected part is held between the probe 313 and the jaw 305 of the distal treatment portion according to the present embodiment, therefore, the grip force to hold the organism tissue is relatively small at the recess 341 at the extreme end portion of the jaw 305, while the grip force for the organism tissue is great at the contact portion 342 behind the recess 341. If ultrasonic vibration is applied to the probe 313 in this state, therefore, the organism tissue held between the probe 313 and the jaw 305 is coagulated at the recess 341 of the jaw 305, and the organism tissue held between the probe 313 and the jaw 305 is coagulated as it is excised (or incised) at the contact portion 342 of the jaw 305. Thus, the present embodiment can also provide the same effects of the sixth embodiment.

FIG. 35 shows an eighth embodiment of the present invention. In the present embodiment, as in the ultrasonic coagulating/cutting apparatus 201 of the sixth embodiment (see FIGS. 21 to 33B), a probe 313 is provided with a recess 331 and a contact portion 332. As in the seventh embodiment (see FIG. 34), moreover, a notched recess 341 is formed in the distal end portion of that surface of a contact member 312 of a jaw 305 which faces the probe 313, and a contact portion 342 to be in contact with the probe 313 is formed behind the recess 341.

When the organism tissue of an affected part is held between the probe 313 and the jaw 305 of the distal treatment portion according to the present embodiment, therefore, the grip force to hold the organism tissue is relatively small in a region between the recess 341 at the extreme end portion of the jaw 305 and the recess 331 of the probe 313, while the grip force for the organism tissue is great at the contact portions 342 and 332 behind the recesses 341 and 331. If ultrasonic vibration is applied to the probe 313 in this state, therefore, the organism tissue held between the probe 313 and the jaw 305 is coagulated at the portion between the recess 341 of the jaw 305 and the recess 331 of the probe 313, and the organism tissue held between the probe 313 and the jaw 305 is coagulated as it is excised (or incised) at the portion between the contact portion 342 of the jaw 305 and the contact portion 332 of the probe 313. Thus, the present embodiment can also provide the same effects of the sixth embodiment.

Figure 36:
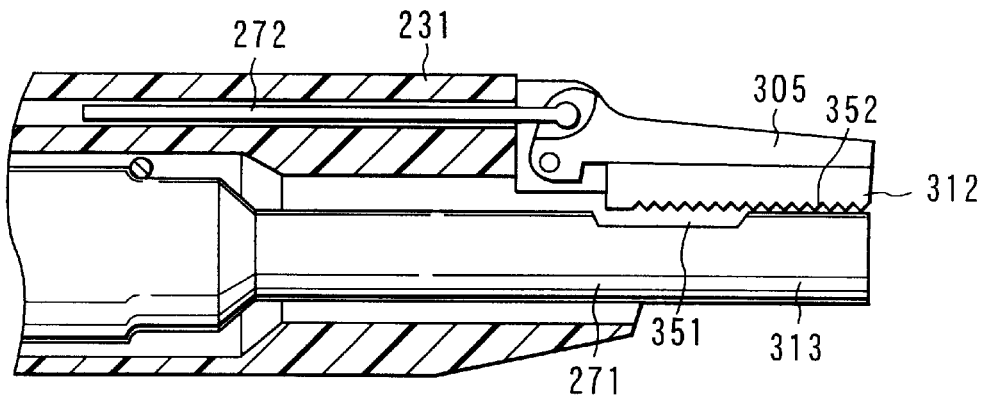
FIG. 36 is a profile of a distal treatment portion showing an arrangement of the principal part of an ultrasonic coagulating/cutting apparatus of a ninth embodiment of the present invention.

FIG. 36 shows a ninth embodiment of the present invention. The present embodiment is obtained by modifying the arrangement of the distal treatment portion of the probe unit 203 of the ultrasonic coagulating/cutting apparatus 201 of the sixth embodiment (see FIGS. 21 to 33B) in the following manner.

More specifically, in the present embodiment, a notched recess (non-contact portion) 351 is formed on the rear side of that surface of a probe 313 of the distal treatment portion of a probe unit 203 which faces a jaw 305, and a contact portion 352 to be in contact with the jaw 305 is formed in front of the recess 351. The recess 351 of the jaw 305 is kept untouched by the probe 313 when the jaw 305 is closed or rocked toward the probe 313, and functions as a portion for coagulating a to-be-treated region of the organism tissue held between the probe 313 and the jaw 305. The contact portion 352 of the jaw 305 moves to a position where it touches the probe 313 when the jaw 305 is rocked toward the probe 313, and functions as a portion for excising (or incising) the organism tissue held between the probe 313 and the jaw 305. The recess 351 of the probe 313 is formed by cutting during the manufacture of the probe 313.

When the organism tissue of an affected part is held between the probe 313 and the jaw 305 of the distal treatment portion according to the present embodiment, therefore, the grip force to hold the organism tissue is relatively small at a portion corresponding to the recess 351 of the probe 313, while the grip force for the organism tissue is great at the contact portion 352 in front of the recess 351. If ultrasonic vibration is applied to the probe 313 in this state, therefore, the organism tissue held between the probe 313 and the jaw 305 is coagulated at the recess 351 of the probe 313, and the organism tissue held between the probe 313 and the jaw 305 is coagulated as it is excised (or incised) at the contact portion 352 of the probe 313. Thus, the present embodiment can also provide the same effects of the sixth embodiment.

Figure 37:
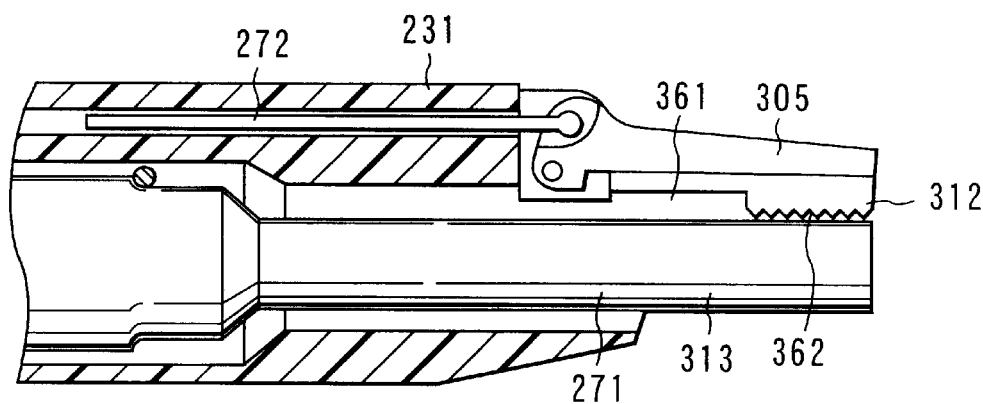
FIG. 37 is a profile of a distal treatment portion showing an arrangement of the principal part of an ultrasonic coagulating/cutting apparatus of a tenth embodiment of the present invention.

FIG. 37 shows a tenth embodiment of the present invention. The present embodiment is obtained by modifying the arrangement of the distal treatment portion of the probe unit 203 of the ultrasonic coagulating/cutting apparatus 201 of the sixth embodiment (see FIGS. 21 to 33B) in the following manner.

More specifically, in the present embodiment, a notched recess (non-contact portion) 361 is formed on the rear side of that surface of a contact member 312 of a jaw 305 of the distal treatment portion of a probe unit 203 which faces a probe 313, and a contact portion 362 to be in contact with the probe 313 is formed in front of the recess 361. The recess 361 of the jaw 305 is kept untouched by the probe 313 when the jaw 305 is closed or rocked toward the probe 313, and functions as a portion for coagulating a to-be-treated region of the organism tissue held between the probe 313 and the jaw 305. The contact portion 362 of the jaw 305 moves to a position where it touches the probe 313 when the jaw 305 is rocked toward the probe 313, and functions as a portion for excising (or incising) the organism tissue held between the probe 313 and the jaw 305.

When the organism tissue of an affected part is held between the probe 313 and the jaw 305 of the distal treatment portion according to the present embodiment, therefore, the grip force to hold the organism tissue is relatively small at the recess 361 of the jaw 305, while the grip force for the organism tissue is great at the contact portion 362 in front of the recess 361. If ultrasonic vibration is applied to the probe 313 in this state, therefore, the organism tissue held between the probe 313 and the jaw 305 is coagulated at the recess 361 of the jaw 305, and the organism tissue held between the probe 313 and the jaw 305 is coagulated as it is excised (or incised) at the contact portion 362 of the jaw 305. Thus, the present embodiment can also provide the same effects of the sixth embodiment.

Figure 38:
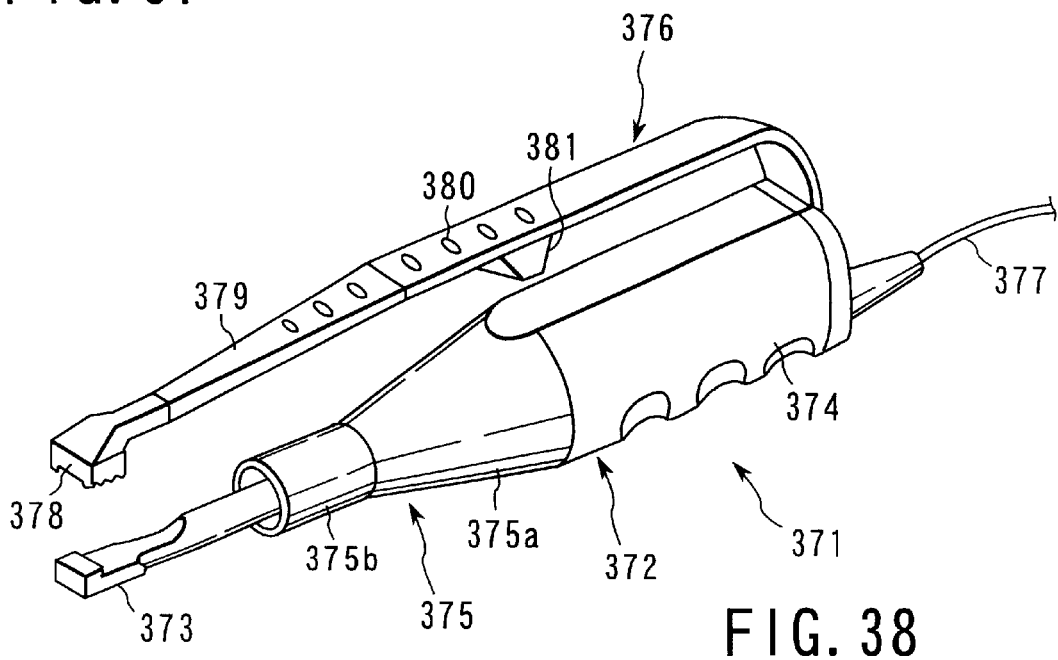
FIG. 38 is a general perspective view of an ultrasonic coagulating/cutting apparatus of an eleventh embodiment of the present invention.
Figure 39A:
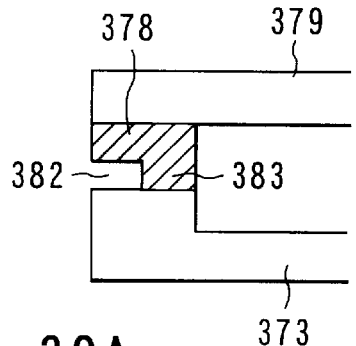
FIG. 39A is a side view showing an arrangement of the principal part of the ultrasonic coagulating/cutting apparatus of the eleventh embodiment.

FIGS. 38 and 39A show an eleventh embodiment of the present invention. As shown in FIG. 38, the present embodiment is provided with a hand piece 371 of an ultrasonic coagulating/cutting apparatus that is substantially in the form of tweezers.

The hand piece 371 of the present embodiment is provided with a grip portion 372. An ultrasonic vibrator 243 (see FIGS. 27A and 27B) for generating ultrasonic vibration is located in the grip portion 372. The proximal end portion of a horn 244 is coupled to the vibrator 243. A probe unit 373 is provided on the distal end portion of the horn 244. The ultrasonic vibration from the vibrator 243 can be transmitted to the probe unit 373 in a manner such that its amplitude is enhanced by means of the horn 244.

Further, the grip portion 372 is provided with a substantially cylindrical vibrator cover 374 that covers the vibrator 243 and a casing 375 that covers the horn 244 and the probe unit 373. The casing 375 is provided with a tapered horn cover portion 375a and a small-diameter portion 375b that is coupled to the distal end portion of the horn cover portion 375a. The proximal end portion of the horn cover portion 375a of the casing 375 is coupled to a distal end opening of the vibrator cover 374. The distal end portion of the probe unit 373 is kept projecting forward from a distal end opening of the small-diameter portion 375b of the casing 375.

The proximal end portion of the vibrator cover 374 is fixedly fitted with the proximal end portion of a substantially L-shaped connecting portion (operating means constituting portion) 376 and coupled with one end portion of a connecting cord 377. The other end portion of the connecting cord 377 is coupled to the body of the ultrasonic coagulating/cutting apparatus (not shown).

Further, the connecting portion 376 is provided with a jaw 378 separately opposed to the distal end portion of the probe unit 373 and an arm portion 379 that extends from the jaw 378 to the hand side. Skid-proof ribs 380 are provided on the surface of the arm portion 379. A stopper 381 protrudes inward from the inner surface side of the arm portion 379. As the arm portion 379 of the connecting portion 376 is operated, jaw 378 can be moved toward or away from the distal end portion of the probe unit 373 (or closed or opened). The jaw 378 is movable between a closed position where it holds the organism tissue between itself and the probe unit 373 and an open position where it separates from the probe unit 373 to release the organism tissue.

As shown in FIG. 39A, moreover, the jaw 378 is provided with a recess (non-contact portion) 382 cut in its surface opposite to the probe unit 373 and a contact portion 383 to be in contact with the probe unit 373. The recess 382 is located at the extreme end portion of the jaw 378, while the contact portion 383 is located behind the recess 382. The recess 382 of the probe unit 373 is formed by cutting during the manufacture of the probe unit 373.

Further, the recess 382 of the jaw 378 is kept untouched by the probe unit 373 when the jaw 378 is closed or rocked toward the probe unit 373, and functions as a portion for coagulating a to-be-treated region of the organism tissue held between the probe unit 373 and the jaw 378. The contact portion 383 of the jaw 378 moves to a position where it touches the probe unit 373 when the jaw 378 is rocked toward the probe unit 373, and functions as a portion for excising (or incising) the organism tissue held between the probe unit 373 and the jaw 378.

The following is a description of the operation of the arrangement described above. In operating the ultrasonic coagulating/cutting apparatus of the present embodiment, the organism tissue is inserted between the probe unit 373 at the distal end portion of the hand piece 371 and the jaw 378. Thereafter, the jaw 378 at the distal end portion of the arm portion 379 is moved toward the probe unit 373 by gripping the arm portion 379 of the connecting portion 376, vibrator cover 374, and casing 375 together, whereupon the organism tissue is held between the probe unit 373 and the jaw 378. As this is done, the grip force to hold the organism tissue is relatively small at the recess 382 at the extreme end portion of the jaw 378, while the grip force for the organism tissue is great at the contact portion 383 behind the recess 382.

In this state, ultrasonic vibration is applied to the probe unit 373. As this is done, the organism tissue held between the probe unit 373 and the jaw 378 is coagulated at the recess 382 of the jaw 378. At the contact portion 383 of the probe unit 373, moreover, the organism tissue held between the probe unit 373 and the jaw 378 coagulates as it is excised (or incised).

When the organism tissue of an affected part is held between the probe unit 373 and the jaw 378 of the distal treatment portion according to the present embodiment, therefore, the grip force to hold the organism tissue is relatively small at the recess 382 at the extreme end portion of the jaw 378, while the grip force for the organism tissue is great at the contact portion 383 behind the recess 382. If ultrasonic vibration is applied to the probe unit 373 in this state, therefore, the organism tissue held between the probe unit 373 and the jaw 378 is coagulated at the recess 382 of the jaw 378, and the organism tissue held between the probe unit 373 and the jaw 378 is coagulated as it is excised (or incised) at the contact portion 383 of the jaw 378. Thus, the present embodiment can also provide the same effects of the sixth embodiment.

Figure 39B:
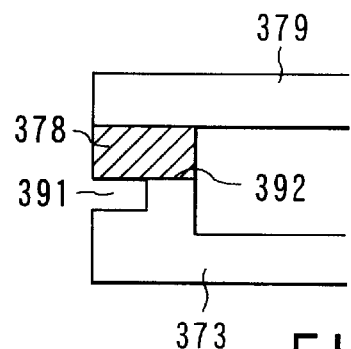
FIG. 39B is a side view of the principal part showing a modification of the ultrasonic coagulating/cutting apparatus of the eleventh embodiment.

FIG. 39B shows a modification of the eleventh embodiment. In the present modification, a recess 391 is formed in the distal end portion of the probe unit 373 in the hand piece 371 of the ultrasonic coagulating/cutting apparatus of the eleventh embodiment (see FIGS. 38 and 39A), and a contact portion 392 to be in contact with the jaw 378 is formed in a region behind the recess 391.

Further, the recess 391 of the probe unit 373 is kept untouched by the jaw 378 when the jaw 378 is closed or rocked toward the probe unit 373, and functions as a portion for coagulating a to-be-treated region of the organism tissue held between the probe unit 373 and the jaw 378. The contact portion 392 of the probe unit 373 moves to a position where it touches the jaw 378 when the jaw 378 is rocked toward the probe unit 373, and functions as a portion for excising (or incising) the organism tissue held between the probe unit 373 and the jaw 378.

When the organism tissue of an affected part is held between the probe unit 373 and the jaw 378 of the distal treatment portion according to the present embodiment, therefore, the grip force to hold the organism tissue is relatively small at the recess 391 at the extreme end portion of the probe unit 373, while the grip force for the organism tissue is great at the contact portion 392 behind the recess 391. If ultrasonic vibration is applied to the probe unit 373 in this state, therefore, the organism tissue held between the probe unit 373 and the jaw 378 is coagulated at the recess 391 of the probe unit 373, and the organism tissue held between the probe unit 373 and the jaw 378 is coagulated as it is excised (or incised) at the contact portion 392 of the probe unit 373. Thus, the present embodiment can also provide the same effects of the eleventh embodiment.

FIGS. 40 to 42C show a twelfth embodiment of the present invention. The present embodiment is obtained by modifying the arrangement of the distal treatment portion of the probe unit 203 of the ultrasonic coagulating/cutting apparatus 201 of the sixth embodiment (see FIGS. 21 to 33B) in the following manner.

Figure 40:
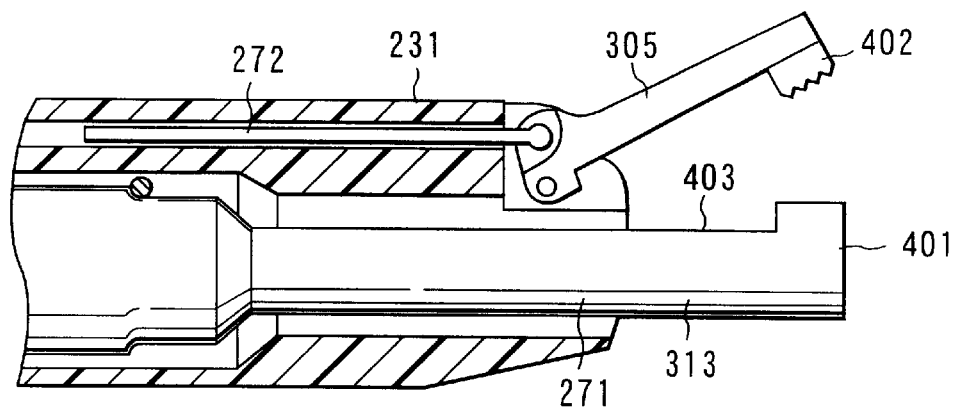
FIG. 40 is a profile of a distal treatment portion showing an arrangement of the principal part of an ultrasonic coagulating/cutting apparatus of a twelfth embodiment of the present invention.
Figure 41A:
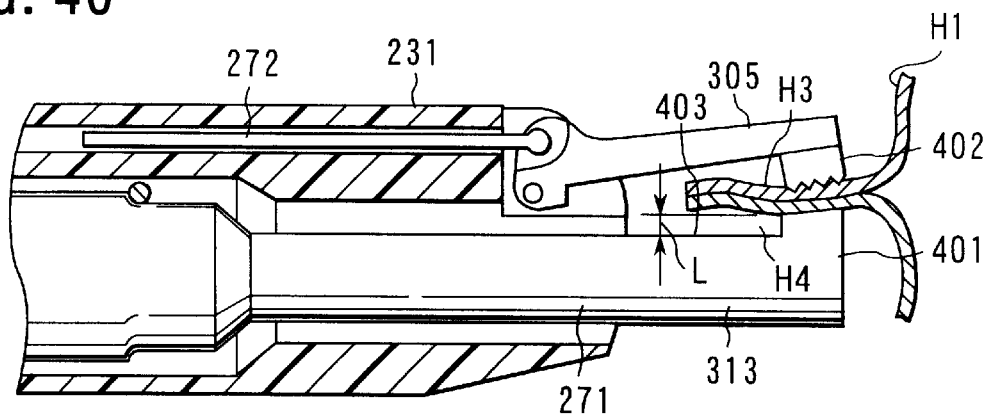
FIG. 41A is a profile of the principal part showing an operating state of the ultrasonic coagulating/cutting apparatus of the twelfth embodiment.

More specifically, a projection 401 protrudes toward a jaw 305 from the distal end portion of a probe 313 of the distal treatment portion of a probe unit 203 of a ultrasonic coagulating/cutting apparatus 201 of the present embodiment, as shown in FIG. 40. Corresponding to the projection 401 of the probe 313 in position, moreover, a similar projection 402 protrudes from the distal end portion of the jaw 305. Thus, when the jaw 305 is closed or rocked toward the probe 313, a to-be-treated region of the organism tissue can be held between the projection 401 of the probe 313 and the projection 402 of the jaw 305, as shown in FIG. 41A. A non-contact portion 403 that cannot be touched by the organism tissue is formed in any other part of the probe 313 than the projection 401.

In operating the ultrasonic coagulating/cutting apparatus 201 of the present embodiment, the to-be-treated region of the organism tissue is held between the projection 401 of the probe 313 and the projection 402 of the jaw 305, as shown in FIG. 41A, when the jaw 305 is closed or rocked toward the probe 313. As this is done, all the area of the non-contact portion 403 except the projection 401 of the probe 313 is kept with a space of a length L shown in FIG. 41A without touching the organism tissue.

Figure 41B:
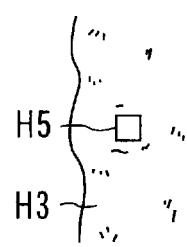
FIG. 41B is a plan view showing a cut portion formed in an organism tissue.

If ultrasonic vibration is applied to the probe 313 in this state, the to-be-treated region of the organism tissue held between the projection 401 of the probe 313 and the projection 402 of the jaw 305 is subjected to ultrasonic treatment, such as coagulation or incision. In the ultrasonic treatment by means of the ultrasonic coagulating/cutting apparatus 201 of the present embodiment, therefore, a peripheral edge region H3 of each anastomotic opening H2 of a blood vessel H1, for example, is locally subjected to coagulation, incision, or other treatment, whereby a local punched ultrasonic treatment portion H5 can be formed, as shown in FIG. 41B.

Accordingly, the above-described arrangement provides the following effects. More specifically, according to the present embodiment, the projection 401 is formed protruding from the distal end portion of the probe 313 toward the jaw 305, and the similar projection 402 is formed protruding from the distal end portion of the jaw 305, corresponding to the projection 401 of the probe 313 in position, so that the to-be-treated region of the organism tissue can be held between the projection 401 of the probe 313 and the projection 402 of the jaw 305, as shown in FIG. 41A, when the jaw 305 is closed or rocked toward the probe 313. Thus, a narrow range of the to-be-treated region of the organism tissue, such as the local punched ultrasonic treatment portion H5 shown in FIG. 41B, can be coagulated (or cut) pointedly, so that pinpoint contact bonding, such as vascular inosculation or vascular suture, can be effected.

Figure 42A:
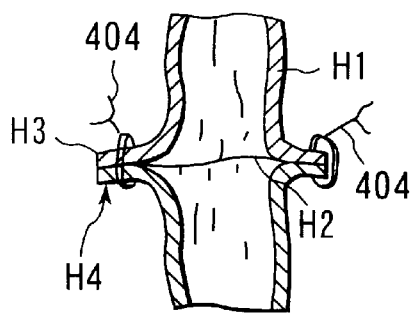
FIG. 42A is a profile of a principal part showing a state in which a ring-shaped junction formed by joining the respective peripheral edge regions of anastomotic openings of a blood vessel is tacked with thread during operation for vascular inosculation using the ultrasonic coagulating/cutting apparatus of the twelfth embodiment.
Figure 42B:
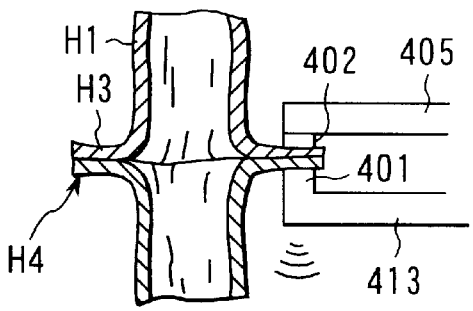
FIG. 42B is a profile of the principal part showing operation for forming a local punched ultrasonic treatment portion in the ring-shaped junction obtained by joining the respective peripheral edge regions of the anastomotic openings by means of the ultrasonic coagulating/cutting apparatus.
Figure 42C:
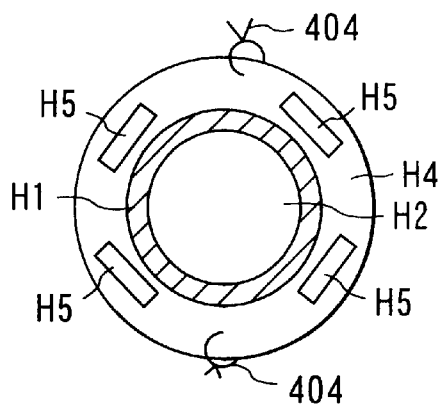
FIG. 42C is a profile of the principal part showing an inosculated portion of the blood vessel having undergone the operation for vascular inosculation using the ultrasonic coagulating/cutting apparatus.

FIGS. 42A to 42C show steps of procedure for carrying out vascular inosculation by using the ultrasonic coagulating/cutting apparatus 201 of the present embodiment. First, a ring-shaped junction H4 that is formed by joining the respective peripheral edge regions H3 of the anastomotic openings H2 of the blood vessel H1 is tacked with thread 404. As this is done, the thread 404 is tacked to two diametrically opposite points on the circumference of the junction H4.

Subsequently, by using the ultrasonic coagulating/cutting apparatus 201 of the present embodiment, the local punched ultrasonic treatment portion (coagulated portion) H5 is formed in the ring-shaped junction H4 that is obtained by joining the respective peripheral edge regions H3 of the anastomotic openings H2, as shown in FIG. 42B. FIG. 42C shows an anastomotic portion of the blood vessel H1 obtained when operation for vascular inosculation by means of the ultrasonic coagulating/cutting apparatus 201 of the present embodiment is finished.

Figure 43:
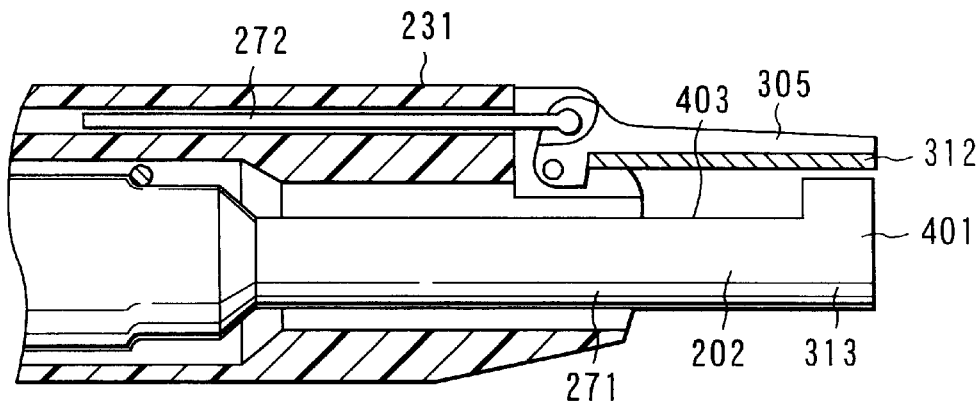
FIG. 43 is a profile of a profile of a distal treatment portion showing an arrangement of the principal part of an ultrasonic coagulating/cutting apparatus of a thirteenth embodiment of the present invention.

FIG. 43 shows a thirteenth embodiment of the present invention. The present embodiment is obtained by modifying the arrangement of the distal treatment portion of the probe unit 203 of the ultrasonic coagulating/cutting apparatus 201 of the twelfth embodiment (see FIGS. 40 to 42C) in the following manner.

More specifically, in the present embodiment, the projection 402 at the distal end portion of the jaw 305 is omitted, and a planar contact member 312 is attached to that surface of the jaw 305 which faces a probe 313. In the present embodiment, moreover, a projection 401 protrudes from the distal end portion of the probe 313 only.

Thus, in the present embodiment, as in the twelfth embodiment, all the area of a non-contact portion 403 except the projection 401 of the probe 313 is kept with a space of a length L without touching the organism tissue. As in the case of the twelfth embodiment, therefore, a narrow range of the to-be-treated region of the organism tissue, such as the local punched ultrasonic treatment portion H5 shown in FIG. 41B, can be coagulated (or cut) pointedly. Accordingly, pinpoint contact bonding, such as vascular inosculation or vascular suture, can be effected in the same manner as in the twelfth embodiment.

Figure 44:
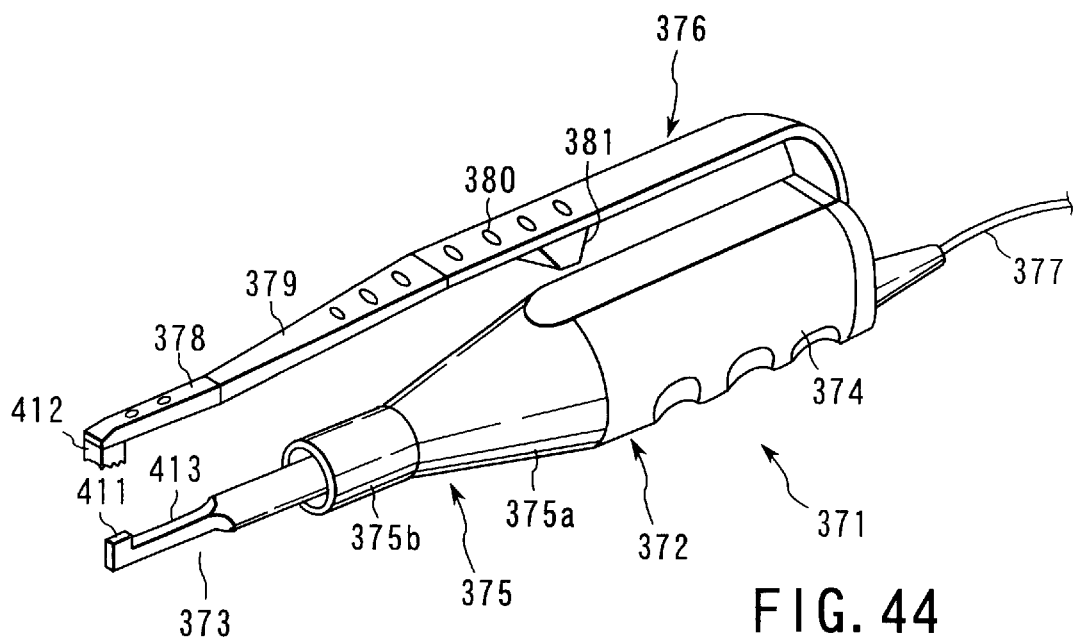
FIG. 44 is a perspective view showing an ultrasonic coagulating/cutting apparatus of a fourteenth embodiment of the present invention.

FIG. 44 shows a fourteenth embodiment of the present invention. The present embodiment is obtained by modifying the arrangement of the hand piece 371 of the substantially tweezers-shaped ultrasonic coagulating/cutting apparatus of the eleventh embodiment (see FIGS. 38 and 39A) in the following manner.

More specifically, in the present embodiment, a projection 411 protrudes from the distal end portion of a probe unit 373 toward a jaw 378. Corresponding to the projection 411 of the probe unit 373 in position, moreover, a similar projection 412 protrudes from the distal end portion of the jaw 378. Thus, when the jaw 378 is closed or rocked toward the probe unit 373, a to-be-treated region of the organism tissue can be held between the projection 411 of the probe unit 373 and the projection 412 of the jaw 378. A non-contact portion 413 that cannot be touched by the organism tissue is formed in any other part of the probe unit 373 than the projection 411.

Thus, in the present embodiment, as in the twelfth embodiment (see FIGS. 40 to 42C), all the area of the non-contact portion 413 except the projection 411 of the probe unit 373 is kept untouched by the organism tissue. As in the case of the twelfth embodiment, therefore, a narrow range of the to-be-treated region of the organism tissue, such as the local punched ultrasonic treatment portion H5 shown in FIG. 41B, can be coagulated (or cut) pointedly. Accordingly, pinpoint contact bonding, such as vascular inosculation or vascular suture, can be effected in the same manner as in the twelfth embodiment.

Figures 45A, 45B:
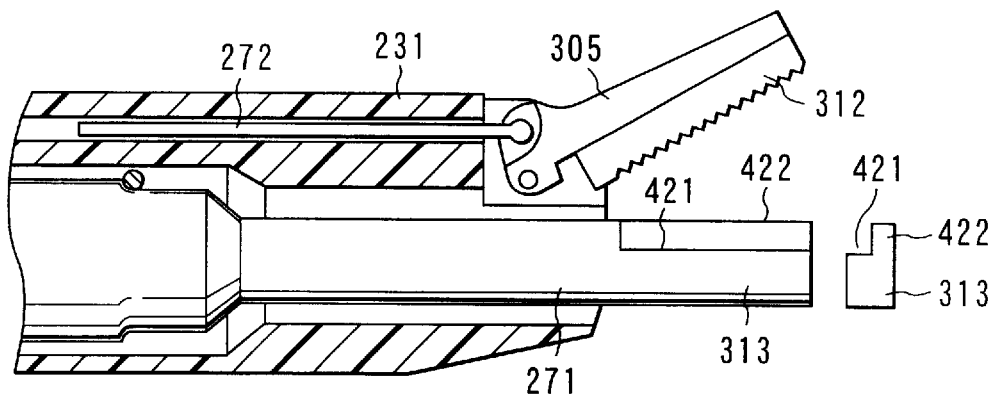
FIG. 45A is a profile of a distal treatment portion showing an arrangement of the principal part of an ultrasonic coagulating/cutting apparatus of a fifteenth embodiment of the present invention.
FIG. 45B is a front view of a probe.
Figure 46:
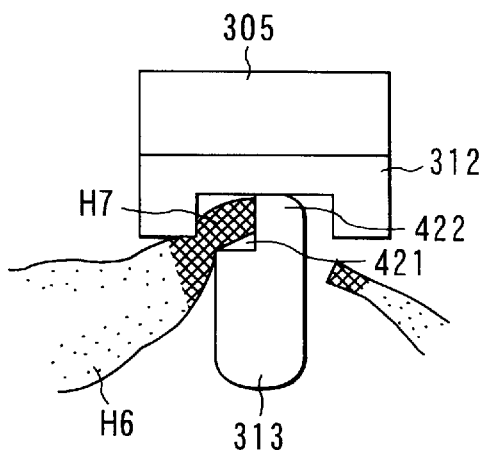
FIG. 46 is a front view of the distal treatment portion showing a state for ultrasonic coagulating/cutting treatment by means of the ultrasonic coagulating/cutting apparatus of the fifteenth embodiment.

FIGS. 45A, 45B and 46 show a fifteenth embodiment of the present invention. The present embodiment is obtained by modifying the arrangement of the distal treatment portion of the probe unit 203 of the ultrasonic coagulating/cutting apparatus 201 of the sixth embodiment (see FIGS. 21 to 33B) in the following manner.

More specifically, in the present embodiment, a notched recess (non-contact portion) 421 is formed in one side portion of that surface of a probe 313 of the distal treatment portion of a probe unit 203 which faces a jaw 305, and a contact portion 422 to be in contact with the jaw 305 is formed on the other side portion (beside the recess 421). The recess 421 of the probe 313 is kept untouched by the jaw 305 when the jaw 305 is closed or rocked toward the probe 313, and functions as a portion for coagulating a to-be-treated region of the organism tissue held between the probe 313 and the jaw 305. The contact portion 422 of the probe 313 touches the jaw 305 when the jaw 305 is rocked toward the probe 313, and functions as a portion for excising (or incising) the organism tissue held between the probe 313 and the jaw 305.

When an organism tissue H6 of an affected part is held between the probe 313 and the jaw 305 of the distal treatment portion according to the present embodiment, as shown in FIG. 46, therefore, the grip force to hold the organism tissue H6 is relatively small at the recess 421 in the one side portion of the probe 313, while the grip force for the organism tissue H6 is great at the contact portion 422 beside the recess 421. If ultrasonic vibration is applied to the probe 313 in this state, therefore, the organism tissue H6 held between the probe 313 and the jaw 305 is coagulated to form a coagulated portion H7 at the recess 421 of the probe 313, and the organism tissue H6 held between the probe 313 and the jaw 305 is coagulated as it is excised (or incised) at the contact portion 422 of the probe 313. Thus, the present embodiment can also provide the same effects of the sixth embodiment. According to the present embodiment, moreover, trimming can be effected such that a part of the organism tissue H6 is securely coagulated at the recess 421 in the one side portion of the probe 313 and unnecessary portions are excised, as shown in FIG. 46.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic coagulating/cutting apparatus comprising;
   an ultrasonic vibrator for generating ultrasonic vibration;
   a vibration transmitting member connected to said ultrasonic vibrator and capable of transmitting the ultrasonic vibration to a treatment portion for treating an organism tissue;
   a probe located on a distal end portion of said vibration transmitting member;
   a jaw supported opposite to the probe for open-close motion and capable of holding the organism tissue in conjunction with said probe;
   an operating member that opens and closes said jaw; and
   a non-contact portion located at least at a part of a surface of one of said jaw and said probe which faces the other of said jaw and said probe, said non-contact portion being capable of coagulating a to-be-treated region held between said probe and said jaw when said jaw is closed or rocked toward said probe.

2. An ultrasonic coagulating/cutting apparatus according to claim 1, wherein said non-contact portion is formed by a step portion of said probe.

3. An ultrasonic coagulating/cutting apparatus according to claim 1, wherein said non-contact portion is formed by a step portion of said jaw.

4. An ultrasonic coagulating/cutting apparatus according to claim 1, wherein said non-contact portion is formed by step portions of said jaw and said probe.

5. An ultrasonic coagulating/cutting apparatus according to claim 1, wherein said non-contact portion is located on a distal end side of said one of said jaw and said probe with respect to a contact portion at which said jaw and said probe touch and hold the organism tissue.

6. An ultrasonic coagulating/cutting apparatus according to claim 1, wherein a contact portion at which said jaw and said probe touch and hold the organism tissue is located on a distal end side of said one of said jaw and said probe with respect to said non-contact portion.

7. An ultrasonic coagulating/cutting apparatus according to claim 1, wherein a contact portion at which said jaw and the probe touch and hold the organism tissue is formed of a soft member.

8. An ultrasonic coagulating/cutting apparatus according to claim 1, wherein a contact portion at which said jaw and the probe touch and hold the organism tissue has surface irregularity.

9. An ultrasonic coagulating/cutting apparatus comprising:
  an ultrasonic vibrator for generating ultrasonic vibration;
  a vibration transmitting member connected to said ultrasonic vibrator and capable of transmitting the ultrasonic vibration to a treatment portion for treating an organism tissue;
  a probe located on a distal end portion of said vibration transmitting member;
  a jaw supported opposite to the probe for open-close motion and capable of holding the organism tissue in conjunction with said probe;
  an operating member that opens and closes said jaw; and
  a projection located on an extreme end portion of said probe, said projection serving to nip the organism tissue in conjunction with the jaw opposite thereto.

10. An ultrasonic coagulating/cutting apparatus according to claim 9, wherein said jaw is also provided with a projection, and the projection of said jaw faces the projection of said probe.

11. An ultrasonic coagulating/cutting apparatus according to claim 10, wherein steps are formed individually between said projections and respective other portions of said jaw and said probe.

12. An ultrasonic coagulating/cutting apparatus according to claim 9, wherein a step is formed between said projection and another portion of said probe.

13. An ultrasonic coagulating/cutting apparatus according to claim 9, wherein said projection is located on a proximal end side of said probe in a region where said jaw and said probe face each other.

14. An ultrasonic coagulating/cutting apparatus according to claim 9, wherein said projection is located on a distal end side of said probe in a region where said jaw and said probe face each other.

15. An ultrasonic coagulating/cutting apparatus according to claim 9, wherein said projection is formed of a soft member.

16. An ultrasonic coagulating/cutting apparatus according to claim 9, wherein a surface of said projection has irregularity.

17. A medical tool comprising:
  a treatment main body;
  an insertion portion provided at the treatment main body and insertable into a subject;
  a supporting shaft provided in the insertion portion;
  a jaw supported by the supporting shaft and rotatable around the supporting shaft;
  a driving shaft connected to the jaw for transmitting a driving power for rotating the jaw;
  a first handle connected to the treatment main body;
  a second handle which is connected to the driving shaft and which is movable relative to the first handle to perform opening and closing operations, thereby driving the driving shaft to rotate the jaw;
  first and second finger grips provided at the first and second handles, respectively, for moving the second handle relative to the first handle such that the first and second handles perform the opening and closing operations; and
  a projection portion at one of the first and second finger grips such that the projection is brought into contact with the other of the first and second finger grips when the second handle is moved relative to the first handle to perform the closing operation;
  wherein a projection amount of the projection is adjustable to change a maximum closing position of the jaw which is closed by the closing operation of the second handle relative to the first handle.

18. A medical tool according to claim 17, wherein the projection projects only to a space between the first and second finger grips.

19. A medical tool according to claim 17, wherein the maximum closing position is adjustable to a position in which the jaw and a probe are not in contact with each other.

20. An ultrasonic coagulating/cutting apparatus comprising:
  a treatment member including (i) a main body, (ii) an insertion portion provided at the main body and insertable into a subject, (iii) an ultrasonic vibrator supported by the main body for generating ultrasonic vibration, (iv) a vibration transmitting member provided inside the insertion portion and connected to the ultrasonic vibrator for transmitting the ultrasonic vibration to a treatment portion for treating an organism tissue, (v) a probe provided at a distal and portion of the vibration transmitting member, (vi) an openable and closable jaw supported opposite to the probe for holding the organism tissue in conjunction with the probe, and (vii) an openable and closable operating member provided at the main body for opening and closing the jaw;
  a stopper provided at the treatment member for stopping movement of the operating member, said stopper being movable relative to the treatment member by an external operation; and
  a stopper fixing member provided at the treatment member for engaging with the stopper and fixing the stopper in a position selected from a plurality of switchable positions including first and second positions, said first position being determined as a cutting position where the organism tissue held by the jaw and the probe is cut, and said second position being determined as a coagulating position where the jaw is stopped before reaching the cutting position.

21. An ultrasonic coagulating/cutting apparatus according to claim 20, wherein at least one of the first and second positions is a position in which the probe and the jaw are not in contact with each other.

22. A medical tool comprising:

a treatment member including (i) a treatment main body, (ii) an insertion portion provided at the treatment main body and insertable into a subject, (iii) a supporting shaft provided in the insertion portion, (iv) a jaw supported by the supporting shaft and rotatable around the supporting shaft, (v) a driving shaft connected to the jaw for transmitting a driving power for rotating the jaw, (vi) a first handle connected to the treatment main body, and (vii) a second handle which is connected to the driving shaft and which is movable relative to the first handle to perform opening and closing operations, thereby driving the driving shaft to rotate the jaw;

a stopper provided at the treatment member for stopping movement of the second handle relative to the first handle and driving of the driving shaft, said stopper being movable relative to the treatment member by an external operation; and a stopper fixing member provided at the treatment member for engaging with the stopper and fixing the stopper in a position selected from a plurality of switchable positions including first and second positions, said first position being determined as a cutting position where an organism tissue held by the jaw and a probe is cut, and said second position being determined as a coagulating position where the jaw is stopped before reaching the cutting position.

23. An ultrasonic coagulating/cutting apparatus according to claim 22, wherein at least one of the first and second positions is a position in which the probe and the jaw are not in contact with each other.

24. An ultrasonic coagulating/cutting apparatus comprising:

a treatment member including (i) a main body, (ii) an insertion portion provided at the main body and insertable into a subject, (iii) an ultrasonic vibrator supported by the main body for generating ultrasonic vibration, (iv) a vibration transmitting member provided inside the insertion portion and connected to the ultrasonic vibrator for transmitting the ultrasonic vibration to a treatment portion for treating an organism tissue, (v) a probe provided at a distal end portion of the vibration transmitting member, (vi) an openable and closable jaw supported opposite to the probe for holding the organism tissue in conjunction with the probe, and (vii) an openable and closable operating member provided at the main body for opening and closing the jaw;

stopping means for stopping movement of the operating member, said stopping means being movable relative to the treatment member by an external operation; and fixing means for engaging with the stopping means and fixing the stopping means in a position selected from a plurality of switchable positions including first and second positions, said first position being determined as a cutting position where the organism tissue held by the jaw and the probe is cut, and said second position being determined as a coagulating position where the jaw is stopped before reaching the cutting position.

25. A medical tool comprising:

a treatment member including (i) a treatment main body, (ii) an insertion portion provided at the treatment main body and insertable into a subject, (iii) a supporting shaft provided in the insertion portion, (iv) a jaw supported by the supporting shaft and rotatable around the supporting shaft, (v) a driving shaft connected to the jaw for transmitting a driving power for rotating the jaw, (vi) a first handle connected to the treatment main body, and (vii) a second handle which is connected to the driving shaft and which is movable relative to the first handle to perform opening and closing operations, thereby driving the driving shaft to rotate the jaw;

stopping means for stopping movement of the second handle relative to the first handle and driving of the driving shaft, said stopping means being movable relative to the treatment member by an external operation; and fixing means for engaging with the stopping means and fixing the stopping means in a position selected from a plurality of switchable positions including first and second positions, said first position being determined as a cutting position where an organism tissue held by the jaw and a probe is cut, and said second position being determined as a coagulating position where the jaw is stopped before reaching the cutting position.

* * * * *